United States Patent
Kong et al.

(10) Patent No.: US 12,054,524 B2
(45) Date of Patent: Aug. 6, 2024

(54) **RECOMBINANT EXPRESSION VECTOR FOR HIGH EXPRESSION OF BRAZZEIN IN *SACCHAROMYCES CEREVISIAE* AND METHOD FOR MASS-PRODUCTION OF BRAZZEIN USING THE SAME**

(71) Applicant: CHUNG-ANG UNIVERSITY INDUSTRY-ACADEMIC COOPERATION FOUNDATION, Seoul (KR)

(72) Inventors: Kwang Hoon Kong, Incheon (KR); Han Seul Kim, Seoul (KR); Si Wook Jang, Seoul (KR); Gi Hyeon Chae, Seoul (KR)

(73) Assignee: CHUNG-ANG UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 17/692,508

(22) Filed: Mar. 11, 2022

(65) Prior Publication Data
US 2022/0289799 A1      Sep. 15, 2022

(30) Foreign Application Priority Data

Mar. 12, 2021  (KR) .................. 10-2021-0032835

(51) Int. Cl.
*C07K 14/425*  (2006.01)
*C12N 15/81*   (2006.01)

(52) U.S. Cl.
CPC .......... *C07K 14/425* (2013.01); *C12N 15/81* (2013.01); *C12N 2800/102* (2013.01); *C12N 2830/002* (2013.01); *C12N 2830/704* (2013.01)

(58) Field of Classification Search
CPC .......... C12N 15/81; C12N 2800/102; C12N 2830/002; C12N 2830/704; C12N 15/70; C07K 14/425; C07K 14/43; A23K 20/147; A23L 27/31; A61K 8/645
See application file for complete search history.

(56) References Cited

U.S. PATENT DOCUMENTS

2010/0076176 A1* 3/2010 Miles ............... C07K 14/43
                                                  435/254.2
2012/0322129 A1* 12/2012 Choi ............... C12N 9/0006
                                                  435/167

FOREIGN PATENT DOCUMENTS

| KR | 20110097043 |   | 8/2011 |
|----|-------------|---|--------|
| KR | 101356914   |   | 1/2014 |
| TW | 201125977 A | * | 8/2011 |

OTHER PUBLICATIONS

Partow, Siavash, et al. "Characterization of different promoters for designing a new expression vector in *Saccharomyces cerevisiae*." Yeast 27.11 (2010): 955-964 (Year: 2010).*
Jo, Hyun-Joo, Jin-Seok Noh, and Kwang-Hoon Kong. "Efficient secretory expression of the sweet-tasting protein brazzein in the yeast Kluyveromyces lactis." Protein expression and purification 90.2 (2013): 84-89 (Year: 2013).*
Yoshiyuki, Hayama, et al. "Extremely simple, rapid and highly efficient transformation method for the yeast *Saccharomyces cerevisiae* using glutathione and early log phase cells." Journal of bioscience and bioengineering 94.2 (2002): 166-171 (Year: 2002).*
Van't Klooster, Joury S., et al. "Periprotein lipidomes of *Saccharomyces cerevisiae* provide a flexible environment for conformational changes of membrane proteins." Elife 9 (2020): e57003 (Year: 2020).*
Eykamp, William. "Microfiltration and ultrafiltration." Membrane science and technology. vol. 2. Elsevier, 1995. 1-43 (Year: 1995).*
Dong, Bingxue, et al. "A rapid and simple method for screening large numbers of recombinant DNA clones." Journal of Rapid Methods & Automation in Microbiology 15.3 (2007): 244-252 (Year: 2007).*
TW-201125977-A, English Translation (Year: 2011).*
Kong, Kwang Hoon, The biochemical property research and high efficiency production method development of the high degree of sweetness protein brazzein, the final report, Jul. 2018 publication and Sep. 19, 2020 disclosure, 97 pages.
Muhammad Tehseen et al., "Functional coupling of a nematode chemoreceptor to the yeast pheromone response pathway", PLoS One 9(11): e111429, 2014, 21 pages.

* cited by examiner

Primary Examiner — Nancy J Leith
Assistant Examiner — Kyle T Rega
(74) Attorney, Agent, or Firm — Riverside Law LLP

(57) ABSTRACT

The present inventors confirmed that when a brazzein expression recombinant vector for high expression of brazzein in *Saccharomyces cerevisiae* was prepared and a *S. cerevisiae* strain Y2805 was transformed with the recombinant vector, the expression level of brazzein was particularly high, thereby completing an optimal expression system for mass-producing brazzein. Further, when the brazzein expression system is cultured under the optimal culture conditions according to the present invention, the amount of brazzein produced is further increased, the purification process is simple, and costs are reduced. Therefore, it is expected that the brazzein expression system according to the present invention can be widely used for mass-producing and commercializing brazzein, which is a sweet protein.

7 Claims, 18 Drawing Sheets
Specification includes a Sequence Listing.

Wild-type brazzein

| Saccharomyces cerevisiae | GAT | AAG | TGT | AAG | AAG | GTT | TAC | GAA | AAT | TAC | CCA | GTT | TCT | AAG | TGT | CAA | TTG |
|---|---|---|---|---|---|---|---|---|---|---|---|---|---|---|---|---|---|
| WT-Brazzein | D | K | C | K | K | V | Y | E | N | Y | P | V | S | K | C | Q | L |

| Saccharomyces cerevisiae | GCT | AAC | CAA | TGT | AAT | TAC | GAT | TGT | AAG | TTG | GAT | AAG | CAT | GCT | AGA | TCT | GGT |
|---|---|---|---|---|---|---|---|---|---|---|---|---|---|---|---|---|---|
| WT-Brazzein | A | N | Q | C | N | Y | D | C | K | L | D | K | H | A | R | S | G |

| Saccharomyces cerevisiae | TGT | TTT | TAC | GAT | GAA | AAG | AGA | AAC | TTG | CAA | TGT | ATT | TGT | GAT | TAC | TGT | GAA | TAC |
|---|---|---|---|---|---|---|---|---|---|---|---|---|---|---|---|---|---|---|
| WT-Brazzein | C | F | Y | D | E | K | R | N | L | Q | C | I | C | D | Y | C | E | Y |

Brazzein variant(H31R_E36D_E41A_K5R)

| Saccharomyces cerevisiae | GAT | AAG | TGT | AAG | AGA | GTT | TAC | GAA | AAT | TAC | CCA | GTT | TCT | AAG | TGT | CAA | TTG |
|---|---|---|---|---|---|---|---|---|---|---|---|---|---|---|---|---|---|
| 3M_K5R_Brazzein | D | K | C | K | R | V | Y | E | N | Y | P | V | S | K | C | Q | L |

| Saccharomyces cerevisiae | GCT | AAC | CAA | TGT | AAT | TAC | GAT | TGT | AAG | TTG | GAT | AAG | CAT | GCT | AGA | TCT | GGT |
|---|---|---|---|---|---|---|---|---|---|---|---|---|---|---|---|---|---|
| 3M_K5R_Brazzein | A | N | Q | C | N | Y | D | C | K | L | D | K | R | A | R | S | G |

| Saccharomyces cerevisiae | TGT | TTT | TAC | GAT | GAA | AAG | AGA | AAC | TTG | CAA | TGT | ATT | TGT | GAT | TAC | TGT | GAA | TAC |
|---|---|---|---|---|---|---|---|---|---|---|---|---|---|---|---|---|---|---|
| 3M_K5R_Brazzein | C | F | Y | D | D | K | R | N | L | Q | C | I | C | D | Y | C | E | Y |

FIG. 1

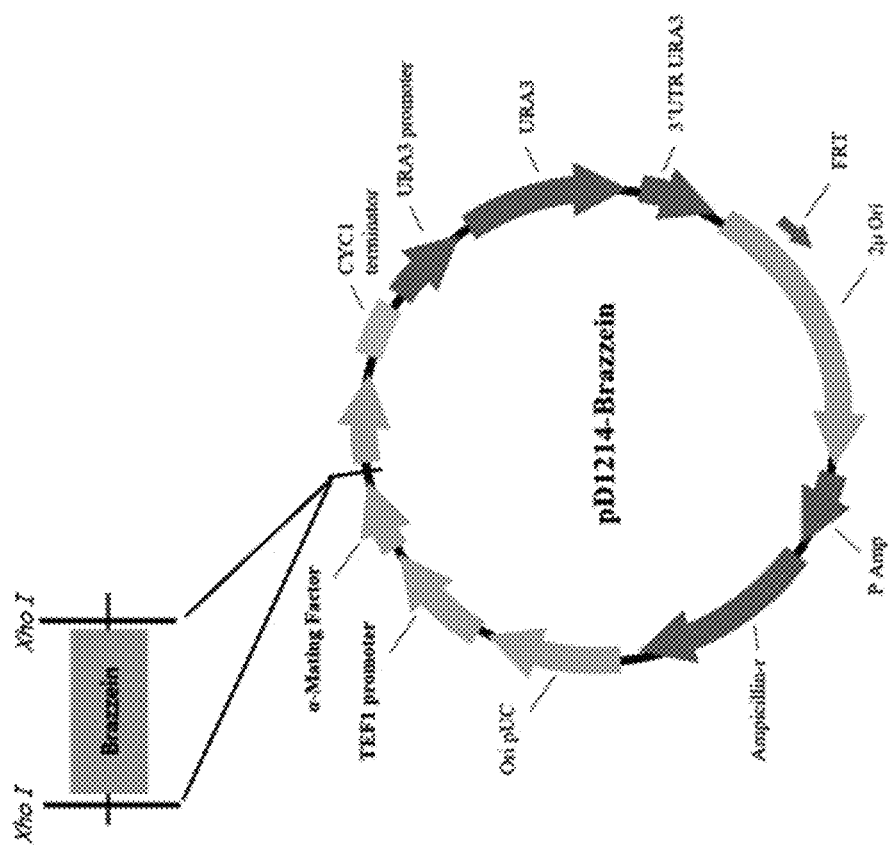
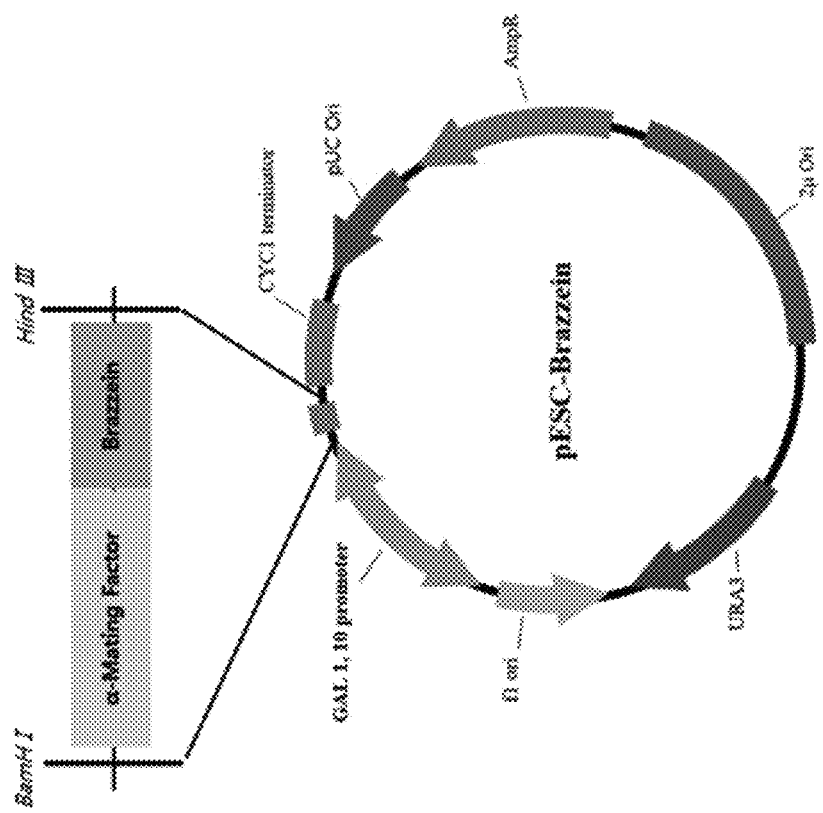
FIG. 2

FIG. 3

Biomolecular Chemistry Lab's Table for Evaluation of Brazzein Sweetness Test

Date:      Name:

Ⓐ

| 1 | 2 | 3 | 4 | 5 | 6 |
|---|---|---|---|---|---|
| 7 | 8 | 9 | 10 | 11 | 12 |

Ⓑ

| 1 | 2 | 3 | 4 | 5 | 6 |
|---|---|---|---|---|---|
| 7 | 8 | 9 | 10 | 11 | 12 |

Ⓒ

| 1 | 2 | 3 | 4 | 5 | 6 |
|---|---|---|---|---|---|
| 7 | 8 | 9 | 10 | 11 | 12 |

Before taking the test
(1) Before the test, the panelists rinse their mouths with prepared water.
(2) Check the number of samples that correspond to the concentration of each type, in which the panelists taste and feel sweetness from No. 1 by 500 μl.
(3) After sampling the taste of each number, the panelists spit out the sample, rinse their mouths with water several times, and then prepares for the next test.
(4) After one type of test is completed, the panelists rinse their mouths and then wait a while to perform a test for the next sample.

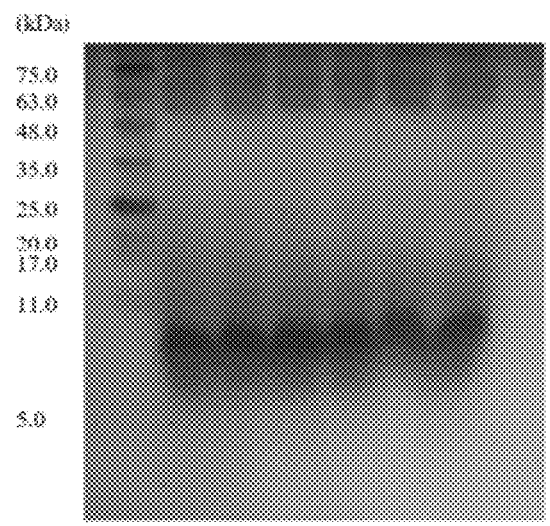
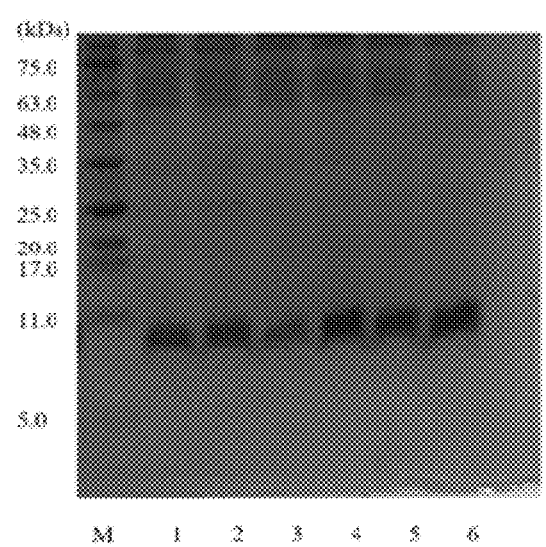
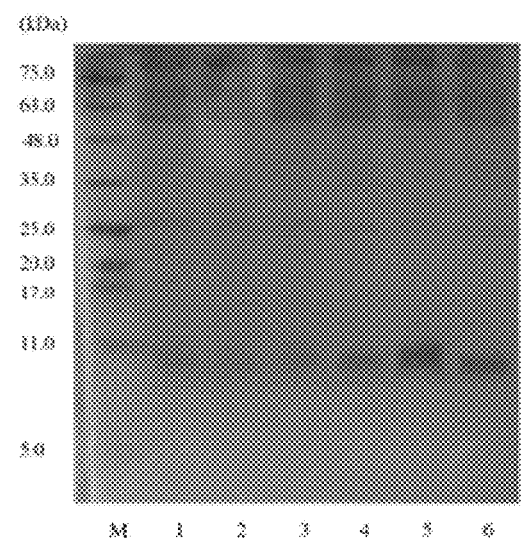
FIG. 5

RECOMBINANT EXPRESSION VECTOR FOR HIGH EXPRESSION OF BRAZZEIN IN *SACCHAROMYCES CEREVISIAE* AND METHOD FOR MASS-PRODUCTION OF BRAZZEIN USING THE SAME

CROSS-REFERENCE TO RELATED APPLICATION

This application claims priority to and the benefit of Korean Patent Application No. 10-2021-0032835, filed on Mar. 12, 2021, the disclosure of which is incorporated herein by reference in its entirety.

REFERENCE TO A "SEQUENCE LISTING," A TABLE, OR A COMPUTER PROGRAM LISTING APPENDIX

The present application hereby incorporates by reference the entire contents of the sequence listing text document named "206132-0127-00US_Replacement_Sequence_Listing.txt". The ASCII text file containing the Sequence Listing of the present application was created on Aug. 24, 2023 and is 39,182 bytes in size.

BACKGROUND

1. Field of the Invention

The present invention relates to a recombinant vector for expressing brazzein to mass-produce brazzein in *Saccharomyces cerevisiae*, and the like.

2. Discussion of Related Art

Brazzein is a natural protein first discovered in pulp tissue of the fruit of Oubli (*Pentadiplandra braazzena* Baillon), which is a tropical fruit native to West Africa, by the Hellekant group of the Department of Animal Science, University of Wisconsin, Madison, USA in 1994 (Ming & Hellekant, 1994). Brazzein is a monomer consisting of 54 amino acid residues, has the smallest molecular weight of 6.5 kDa among sweet proteins, and not only exhibits the most similar sweetness to sugar among sweet proteins, but also has a sugar content that is about 2000-fold and 9500-fold higher than the sweetness of a 2% sugar solution on a molecular weight basis and on a molar basis, respectively. Brazzein has one α-helix and three β-sheets, and includes eight cysteine residues therein. An NMR spectroscopy analysis revealed a higher order structure in which there is no mercapto group (sulfhydryl) and three β-sheets are linked to one another by a hydrogen bond and four disulfide bonds (Caldwell et al., 1998).

Brazzein is present in major and minor forms. The major form has pyro-glutamic acid (pGlu) at the N-terminus and consists of 54 amino acids, and thus accounts for 80% of the wild type, and the minor form consists of 53 amino acids having no pGlu at the N-terminus and accounts for 20% of the wild type. The minor form exhibits a sweetness that is 2-fold higher than the major form. In addition, since indigenous peoples of West Africa have been consuming brazzein for hundreds of years through the fruits of *Pentadiplandra brazzzeana* Baillon, brazzein is considered safe as a food additive.

Brazzein having the characteristics described above has much higher potential and utility as a food additive than other sweet proteins. However, since *Pentadiplandra braazzena* Baillon is a tropical plant that is difficult to cultivate in its natural environment, the commercial potential thereof is very low. Therefore, as an alternative to brazzein produced from natural sources, there have been attempts to produce recombinant brazzein in a variety of strains. However, an effective expression system capable of mass-producing brazzein with high purity and high yield has not yet been discovered.

RELATED ART DOCUMENT

Patent Document (Patent 1) Korean Patent No. 10-1356914

SUMMARY OF THE INVENTION

The present invention has been made in an effort to solve the aforementioned problem, and the present inventors confirmed an expression vector for the high expression of brazzein in a *Saccharomyces* strain and a method for mass-producing brazzein using the same, thereby completing the present invention.

Therefore, an object of the present invention is to provide a recombinant vector for expressing brazzein in *Saccharomyces cerevisiae*, including a pESC-URA vector into which a brazzein encoding gene and an α-mating factor encoding gene are inserted.

Another object of the present invention is to provide a *Saccharomyces cerevisiae* strain for expressing brazzein, which is transformed with the recombinant vector for expressing brazzein.

Still another object of the present invention is to provide a method for mass-producing brazzein, the method including: (1) transforming a *Saccharomyces cerevisiae* strain with the vector of the present invention; (2) culturing the strain transformed in Step (1); (3) obtaining a culture of the transformed strain cultured in Step (2): and (4) purifying brazzein from the culture of Step (3).

However, the technical problems which the present invention intends to solve are not limited to the technical problems that have been mentioned above, and other technical problems which have not been mentioned will be clearly understood by a person with ordinary skill in the art to which the present invention pertains from the following description.

The present invention provides a recombinant vector for expressing brazzein in *Saccharomyces cerevisiae*, including a pESC-URA vector into which a brazzein encoding gene and an α-mating factor encoding gene are inserted.

In an exemplary embodiment, the brazzein encoding gene may include a nucleotide sequence represented by SEQ ID NO: 2, but is not limited thereto.

In another exemplary embodiment, the α-mating factor encoding gene may include a nucleotide sequence represented by SEQ ID NO: 5, but is not limited thereto.

In still another exemplary embodiment, the brazzein encoding gene may be linked to the α-mating factor encoding gene, and an α-mating cleavage site may be present between the brazzein encoding gene and the α-mating factor encoding gene, but is not limited thereto.

In yet another exemplary embodiment, the pESC-URA vector may include a nucleotide sequence represented by SEQ ID NO: 8, but is not limited thereto.

In yet another exemplary embodiment, the recombinant vector may include a nucleotide sequence represented by SEQ ID NO: 7 or 10, but is not limited thereto.

Further, the present invention provides a *Saccharomyces cerevisiae* strain for expressing brazzein, which is transformed with the recombinant vector for expressing brazzein.

In an exemplary embodiment, the *Saccharomyces cerevisiae* strain may be INVSc1, Y2805, or BY4741, but is not limited thereto.

In addition, the present invention provides a culture of a *Saccharomyces cerevisiae* strain for expressing brazzein, which is transformed with the recombinant vector for expressing brazzein according to the present invention.

Furthermore, the present invention provides a method for mass-producing brazzein, the method including:
(1) transforming a *Saccharomyces cerevisiae* strain with the vector of the present invention;
(2) culturing the strain transformed in Step (1);
(3) obtaining a culture of the transformed strain cultured in Step (2); and (4) purifying brazzein from the culture of Step (3).

In an exemplary embodiment, the culturing in Step (2) may satisfy one or more of the following conditions, but is not limited thereto:
(a) the copy number of a recombinant vector for expressing brazzein introduced into the *Saccharomyces cerevisiae* strain is 5 to 60;
(b) the culturing is performed in a complex medium or a defined medium;
(c) the culturing is performed at a pH of 4.5 to 6.5;
(d) the culturing is performed at 20° ° C. to 35° C.; or
(e) the culturing is performed for 6 to 120 hours.

In another exemplary embodiment, when the culturing in Step (2) is performed in a defined medium, the culturing in Step (2) may further satisfy one or more of the following conditions, but is not limited thereto:
(a) the molar ratio of a carbon source (C)/a nitrogen source (N) in the defined medium is 0.1 to 10;
(b) the culturing is performed at a pH of 5 to 8, and the pH is adjusted with acetic acid or a buffer solution;
(c) the defined medium further includes a trace metal at a concentration of 1 to 4 (w/w) %; or
(d) the defined medium further includes a vitamin at a concentration of 1 to 4 (w/w) %.

In another exemplary embodiment, the culturing step in Step (2) includes: culturing a transformed strain by streaking the transformed strain on a solid medium; preparing a pre-culture solution by collecting colonies formed on the solid medium and pre-culturing the colonies in a liquid medium; and culturing the resulting solution by inoculating the pre-culture solution into a main culture solution, and wherein the inoculation concentration of the pre-culture solution may be 1 to 5 (v/v) % of the main culture solution, wherein the OD$_{600}$ of the main culture solution into which the pre-culture solution is inoculated may be 0.05 to 0.25, but is not limited thereto.

In still another exemplary embodiment, the culturing step in Step (2) includes adding an inducer in order to induce the transformed strain to express brazzein, wherein the inducer is selected from glucose, galactose, or a combination thereof, wherein the inducer may be added at a concentration of 1 to 2 (w/w) % of the total medium, but is not limited thereto.

In yet another exemplary embodiment, the adding of the inducer may satisfy one or more of the following conditions, but is not limited thereto:
(a) a ratio of glucose/galactose is 0.1 to 2; or
(b) the inducer is added at a log phase or stationary phase.

In yet another exemplary embodiment, the purifying step in Step (4) may be purifying brazzein by ultrafiltration, but is not limited thereto.

Further, the present invention provides a composition for mass-producing brazzein, including a *Saccharomyces cerevisiae* strain for expressing brazzein, which is transformed with the recombinant vector for expressing brazzein, a culture thereof, or a mixture thereof.

In addition, the present invention provides a food composition including a *Saccharomyces cerevisiae* strain for expressing brazzein, which is transformed with the recombinant vector for expressing brazzein, a culture thereof, or a mixture thereof.

Furthermore, the present invention provides a health functional food including a *Saccharomyces cerevisiae* strain for expressing brazzein, which is transformed with the recombinant vector for expressing brazzein, a culture thereof, or a mixture thereof.

Further, the present invention provides a cosmetic composition including a *Saccharomyces cerevisiae* strain for expressing brazzein, which is transformed with the recombinant vector for expressing brazzein, a culture thereof, or a mixture thereof.

In addition, the present invention provides a feed additive including a *Saccharomyces cerevisiae* strain for expressing brazzein, which is transformed with the recombinant vector for expressing brazzein, a culture thereof, or a mixture thereof.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 1 illustrates amino acid sequences of wild-type brazzein (top) and brazzein (bottom) optimized for expression in a *Saccharomyces cerevisiae* strain:

FIG. 2 illustrates structures of a pESC vector (pESC-Brazzein) into which a brazzein encoding gene, and the like are inserted and a pD1214 vector (pD1214-Brazzein) into which a brazzein encoding gene, and the like are inserted:

FIG. 3 illustrates an evaluation table for testing the sweetness of recombinant brazzein according to the present invention:

FIG. 5 is a result of comparing the expression levels of brazzein according to glucose concentration (w/w) %: galactose concentration (w/w) % relative to the total medium when INVSc1, Y2805, or BY4741 strain is transformed with a pD1214-Brazzein vector, and then cultured by adding inducers (glucose and galactose) thereto. Column M, BlUelf prestained protein ladder; Column 1, 1:0 (glucose (w/w) %: galactose (w/w) %, hereinafter, the same); Column 2, 1:1; Column 3, 1:2; Column 4, 2:0; Column 5, 2:1; Column 6, 2:2:

DETAILED DESCRIPTION OF EXEMPLARY EMBODIMENTS

Figure 4:
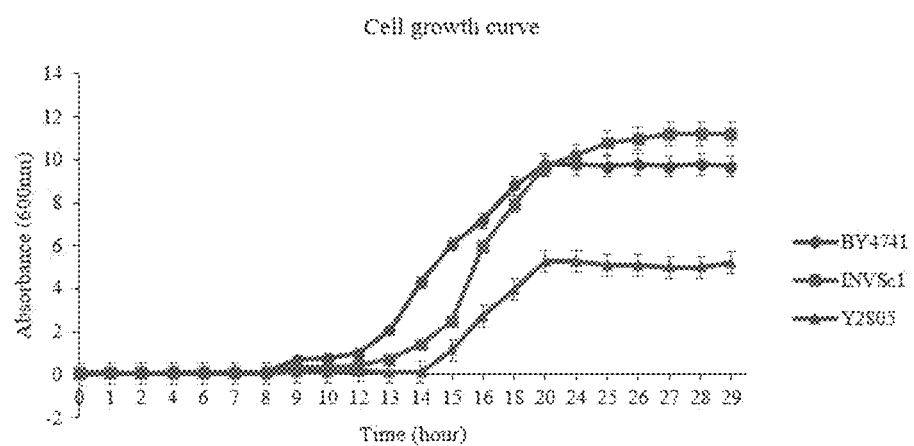
FIG. 4 illustrates a growth curve of INVSc1, Y2805, and BY4741 strains, which are transformed with the recombinant vector for expressing brazzein according to the present invention and cultured at 30° C.

The present invention provides a recombinant vector for expressing brazzein in *Saccharomyces cerevisiae*, including a pESC-URA vector into which a brazzein encoding gene and an α-mating factor encoding gene are inserted.

As used herein, "brazzein" refers to a sweet-tasting protein (protein sweeteners or sweet protein) which produces sweetness. In the present invention, brazzein may include both brazzein in the major form and brazzein in the minor form. Specifically, in the present invention, "brazzein" may include an amino acid sequence represented by SEQ ID NO: 3, and preferably, may consist of an amino acid sequence represented by SEQ ID NO: 3.

"Brazzein encoding gene" refers to a polynucleotide encoding brazzein, and any polynucleotide may be included without limitation as long as it is a polynucleotide encoding brazzein including an amino acid sequence represented by SEQ ID NO: 3.

For example, the brazzein encoding gene may include a brazzein DNA sequence of *Pentadiplandra brazzeana* Baillon, and specifically, may include a nucleotide sequence represented by SEQ ID NO: 1.

However, preferably, the brazzein encoding gene may be a gene modified so as to have a codon optimized for expression in a transformed strain. For example, the brazzein encoding gene may be a gene modified so as to have a codon optimized for expression in a *Saccharomyces cerevisiae*. Therefore, in the present invention, the brazzein encoding gene may include a nucleotide sequence represented by SEQ ID NO: 2, and most preferably, may be encoded by SEQ ID NO: 2, but may be encoded by a nucleotide sequence having a sequence homology of 80% or more, more preferably 90% or more, and even more preferably 95% or more to the nucleotide sequence of SEQ ID NO: 2.

Throughout the present specification, a gene including a nucleotide sequence represented by a specific sequence number may include a nucleotide sequence represented by the corresponding sequence number, and a variant nucleotide sequence in which functional equivalents thereof, for example, some nucleotide sequences are modified by deletion, substitution, or insertion, but expression products can perform functionally the same action. Specifically, a gene including a nucleotide sequence represented by a specific sequence number may include a nucleotide sequence having a sequence homology of 70% or more, more preferably 80% or more, even more preferably 90% or more, and most preferably 95% or more to the nucleotide sequence represented by the corresponding sequence number. For example, the gene may include a nucleotide sequence having a sequence homology of 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. The "sequence homology %" to a polynucleotide is confirmed by comparing a comparison region with an optimally aligned sequence, and a portion of the polynucleotide sequence in the comparison region may include an addition or deletion (that is, a gap) compared to the reference sequence (without addition or deletion) for the optimal alignment of the two sequences.

The "α-mating factor" refers to a signal sequence that enables newly expressed proteins to be secreted outside of cells. Specifically, in the present invention, the "α-mating factor" may include an amino acid sequence represented by SEQ ID NO: 6, and preferably, may consist of an amino acid sequence represented by SEQ ID NO: 6.

The "α-mating factor encoding gene" refers to a gene encoding the α-mating factor, and may include a polynucleotide encoding an α-mating factor including an amino acid sequence represented by SEQ ID NO: 6.

For example, the α-mating factor encoding gene may include a nucleotide sequence encoding α-mating factor of *Saccharomyces cerevisiae*, α-mating factor of *Kluyveromyces lactis*, a KT signal sequence [Tokunaga et al., Yeast, 13: 699-706, 1997), or a pre-SUC2 signal sequence of *Saccharomyces cerevisiae* (Bergkamp et al., Curr Genet, 21:365-370]. Preferably, the α-mating factor encoding gene may include a nucleotide sequence represented by SEQ ID NO: 4.

However, preferably, the α-mating factor encoding gene may be a variant gene modified so as to have a codon optimized for expression in a transformed strain. For example, the α-mating factor encoding gene may be a gene modified so as to have a codon optimized for expression in a *Saccharomyces cerevisiae* strain. Therefore, in the present invention, the α-mating factor encoding gene may include a nucleotide sequence represented by SEQ ID NO: 5, and most preferably, may be encoded by SEQ ID NO: 5, but may be encoded by a nucleotide sequence having a sequence homology of 80% or more, more preferably 90% or more, and even more preferably 95% or more to the nucleotide sequence of SEQ ID NO: 5.

As used herein, the term "polynucleotide" refers to an oligomer or polymer containing two or more linked nucleotides or nucleotide derivatives generally bound to each other via a phosphodiester bond, including deoxyribonucleic acid (DNA) and ribonucleic acid (RNA). The polynucleotide also includes DNA and RNA derivatives including, for example, a nucleotide analog or a backbone bond other than a phosphodiester bond, for example, a phosphotriester bond, a phosphoramidate bond, a phophorothioate bond, a thioester bond, or a peptide bond (peptide nucleic acid). The polynucleotide includes single-stranded and/or double-stranded polynucleotides, for example, deoxyribonucleic acid (DNA) and ribonucleic acid (RNA) as well as analogs of either RNA or DNA.

In the present invention, the brazzein encoding gene may be linked to the α-mating factor encoding gene. For example, the brazzein encoding gene may be linked to the downstream of the α-mating factor encoding gene. Further, in the α-mating factor encoding gene present upstream of the brazzein encoding gene, an α-mating cleavage site may be present. This means a position where brazzein is separated from the α-mating factor encoding gene by a proteolytic enzyme or the like when brazzein is secreted and expressed extracellularly after protein expression.

As used herein, the "vector" for expressing brazzein is a vector capable of appropriately expressing a target protein or target RNA in appropriate cells, and refers to a gene construct including an essential regulatory element operatively linked so as to express a gene insert (for example, a brazzein encoding gene or an α-mating factor encoding gene, and the like). Once transformed into a suitable host, the vector may be replicated and function independently of the host genome, or may be integrated into the genome itself in some cases. Since the plasmid is currently the most commonly used type of vector, the terms plasmid and vector may sometimes be used interchangeably. However, the present invention includes other forms of known vectors having functions equivalent to those known in the art or have become known.

A suitable expression vector may include an expression regulatory element such as a promoter, an operator, an initiation codon, a termination codon, a polyadenylated signal, and an enhancer, and may be variously prepared depending on the purpose. In addition, a vector may include a selection marker for selecting transformed host cells and, a replicable expression vector may include an origin of replication. The vector includes a plasmid vector, a cosmid vector, a bacteriophage vector, a viral vector, and the like, but is not limited thereto. Preferably, the vector may be a vector suitable for expression in yeasts. For example, the vector may be a pESC vector or a pD1214 vector, but is not limited thereto. Preferably, the vector may be a pESC-URA vector or a pD1214-FAks vector. More preferably, the vector may be a pESC-URA vector including a nucleotide sequence represented by SEQ ID NO: 8 or a pD1214-FAks vector including a nucleotide sequence represented by SEQ ID NO: 9. In the present specification, a recombinant vector including a pESC vector into which a brazzein encoding sequence is inserted may be referred to as "pESC-Brazzein", and a recombinant vector including a pD1214 vector into which a brazzein encoding sequence is inserted may be referred to as "pD1214-Brazzein". In the present invention, the recombinant vector for expressing brazzein may include a promoter in which the brazzein encoding gene and the α-mating factor encoding gene are operatively linked. As used herein, the "promoter" refers to a DNA base sequence site that regulates the expression of an operatively linked gene, and includes a constitutive promoter and an inducible promoter. For example, the promoter may be a LAC promoter, GAL promoter, KIADH4 promoter, PGK1 promoter, maltase/maltose permease bi-directional promoter, or the like, but is not limited thereto. Preferably, the promoter may be a GAL promoter, and more preferably, may be GAL1 and/or GAL10. In the present specification, being "operatively linked" means that a specific nucleic acid fragment is linked to other nucleic acid fragments, and thus the function or expression thereof is affected by the other nucleic acid fragments.

In an exemplary embodiment, the recombinant vector for expressing brazzein may include a genetic map of pESC-Brazzein or pD1214-Brazzein represented in FIG. 2.

In the present invention, the recombinant vector for expressing brazzein may include a nucleotide sequence represented by SEQ ID NO: 7 or 10.

The recombinant vector for expressing brazzein according to the present invention is particularly optimized for the expression of brazzein in *Saccharomyces cerevisiae*, but the type of strain which may be transformed with the vector is not limited.

Furthermore, the present invention provides a strain for expressing brazzein, which is transformed with the recombinant vector for expressing brazzein according to the present invention.

In the present specification, the "transformation" means that by introducing DNA into a host, DNA is integrated into a host chromosome as a factor outside the host chromosome, and thus replication is possible. The host cell or strain which may be transformed with the recombinant vector for expressing brazzein according to the present invention may include both prokaryotic cells and eukaryotic cells, but may be, preferably, yeast, a unicellular eukaryotic microorganism. Specifically, the strain may be *Saccharomyces cerevisiae, Kluyveromyces lactis*, or *Pichia pastoris*, or *Lactococcus lactis*, but is not limited thereto. Particularly preferably, the strain may be *Saccharomyces cerevisiae*. More preferably, the strain may be INVSc1, Y2805, or BY4741.

The transformation in the present invention includes any method for introducing a polynucleotide into a cell, and may be performed by selecting a technique suitable for a host cell from standard techniques known in the art. For example, the transformation method includes an electric shock gene transfer method (electroporation), a protoplast fusion method, a calcium phosphate ($CaPO_4$) precipitation method, a calcium chloride ($CaCl_2$)) precipitation method, stirring using silicon carbide fiber, *Agrobacterium*-mediated transformation, polyethylene glycol (PEG), dextran sulfate, Lipofectamine, particle bombardment, and the like, but is not limited thereto.

Furthermore, the present invention provides a culture of a strain transformed with the recombinant vector for expressing brazzein according to the present invention. As used herein, the "culture" refers to a material including a culture solution and/or cultured cells. The "culture solution" refers to a cell culture solution remaining after culturing cells and removing the cells. The culture solution includes brazzein which is secreted and expressed by the transformed strain according to the present invention.

Further, the present invention provides a method for mass-producing brazzein, the method including: (1) transforming a *Saccharomyces cerevisiae* strain with the vector of the present invention; (2) culturing the strain transformed in Step (1); (3) obtaining a culture of the transformed strain cultured in Step (2); and (4) purifying brazzein from the culture of Step (3).

When the transformed strain is cultured, brazzein linked to an α-mating signal sequence is expressed by a vector for expressing brazzein introduced into the strain, and in this case, the expression of brazzein may be promoted by an inducer that promotes the expression of an inducible promoter. Brazzein linked to the α-mating signal sequence migrates to the endoplasmic reticulum, and the α-mating signal sequence may be cleaved from brazzein by a proteolytic enzyme such as signal peptidase or Kex peptidase.

The present inventors optimized the culture conditions such that brazzein can be expressed with optimal efficiency in the *Saccharomyces cerevisiae* strain transformed with the recombinant vector for expressing brazzein.

First, the present inventors optimized the copy number of the recombinant vector for expressing brazzein introduced into the *Saccharomyces cerevisiae* strain. As used herein, the "copy number" refers to the number of vector molecules present in a single cell in a transformed host cell. In the present invention, the copy number of the recombinant vector for expressing brazzein injected into the strain may be 5 to 60. Preferably, the copy number may be 30 to 60. More preferably, the copy number may be 40 to 60, or 40 to 50.

Further, the culturing in Step (2) may be performed in an appropriate medium, and the medium includes a complex medium and a defined medium. For example, the medium may be YPD (1% yeast extract, 2% peptone, 2% glucose) or YNB (0.67% yeast nitrogen base w/o amino acid and ammonium sulfate, 0.2% glucose). Preferably, the transformed strain may be cultured in a defined medium.

In addition, the present inventors optimized pH conditions of the culturing. In the present invention, the culturing may be performed at a pH of 4.5 to 6.5. Preferably, the culturing may be performed at a pH of 5 to 6.5. More preferably, the culturing may be performed at a pH of 5.5 to 6.5.

Furthermore, the present inventors optimized temperature conditions of the culturing. In the present invention, the culturing may be performed at 20 to 35° C. Preferably, the culturing may be performed at 23 to 35° C. or 25 to 33° C. More preferably, the culturing may be performed at 27 to 33° C., and most preferably at 27 to 30° C.

Further, the present inventors optimized the culture time. In the present invention, the culturing may be performed for 6 to 120 hours. Preferably, the culturing may be performed for 48 to 96 hours. More preferably, the culturing may be performed for 60 to 80 hours, and most preferably for 70 to 75 hours.

In addition, the present inventors optimized the molar ratio of a carbon source (C)/a nitrogen source (N) in a defined medium when the culturing is performed in the defined medium. In the present invention, when the culturing is performed in a defined medium, the molar ratio of a carbon source (C)/a nitrogen source (N) may be 0.1 to 10. Preferably, the molar ratio of C/N may be 2 to 8. More preferably, the C/N molar ratio may be 4 to 8, most preferably 5 to 7.

Furthermore, the present inventors optimized the pH of a defined medium when culturing is performed in the defined medium. In the present invention, when the culturing is performed in a defined medium, the culturing may be performed at an initial pH of 4.5 to 6.5. Preferably, the culturing may be performed at an initial pH of 5 to 6.5. More preferably, the culturing may be performed at an initial pH of 5.5 to 6.5. Preferably, the pH may be adjusted by acetic acid.

Alternatively, in the present invention, when the culturing is performed in a defined medium, the culturing may be performed at a pH of 5 to 8. Preferably, the culturing may be performed at a pH of 5.5 to 7. More preferably, the culturing may be performed at a pH of 5.5 to 6.5. More preferably, the pH may be adjusted by a buffer solution, and may be adjusted preferably by potassium phosphate.

Furthermore, in the present invention, when the culturing is performed in a defined medium, the defined medium may further include a trace metal at a concentration of 1 to 4 (w/w) %. Specifically, the defined medium may further include a trace metal of 5 to 30 mg/L×Trace metal, preferably, may further include a trace metal of 10 to 25 mg/L×Trace metal, and more preferably, may further include a trace metal of 15 to 25 mg/L×Trace metal. Most preferably, the defined medium further includes a trace metal of 20 mg/L×Trace metal.

Further, in the present invention, when the culturing is performed in a defined medium, the defined medium may further include a vitamin at a concentration of 1 to 4 (w/w) %. Specifically, the defined medium may further include a vitamin of 5 to 40 mg/L×vitamin, and preferably, may further include a vitamin of 20 to 40 mg/L×vitamin. More preferably, the defined medium may further include a vitamin of 25 to 35 mg/L×vitamin. Most preferably, the defined medium may further include a vitamin of 30 mg/L×vitamin.

In addition, in the present invention, the culturing step in Step (2) may include: culturing a transformed strain by streaking the transformed strain on a solid medium; preparing a pre-culture solution by collecting colonies formed on the solid medium and pre-culturing the colonies in a liquid medium; and culturing the resulting solution by inoculating the pre-culture solution into a main culture solution. In this case, the inoculation concentration of the pre-culture solution may be 1 to 5 (v/v) % of the main culture solution. Preferably, the inoculation concentration of the pre-culture solution may be 2 to 4 (v/v) % of the main culture solution. More preferably, the inoculation concentration of the pre-culture solution may be 2.5 to 3.5 (v/v) % of the main culture solution. Furthermore, the $OD_{600}$ of a main culture solution into which the pre-culture solution is inoculated may be 0.05 to 0.25. Preferably, the $OD_{600}$ of a main culture solution into which the pre-culture solution is inoculated may be 0.05 to 0.2. More preferably, the $OD_{600}$ of a main culture solution into which the pre-culture solution is inoculated may be 0.1 to 0.2. Further, in the present invention, the culturing step in Step (2) may include adding an inducer in order to induce the transformed strain to express brazzein. Preferably, the inducer may be glucose, galactose, or a combination thereof. In addition, the inducer may be added at a concentration of 1 to 2 (w/w) % of the total medium.

In this case, when the recombinant vector for expressing brazzein includes a pD1214-FAKS vector, the ratio of glucose:galactose to be added to the medium may be 1 to 2:0 to 2. Alternatively, when the recombinant vector for expressing brazzein is a pESC-URA vector, the ratio of glucose:galactose to be added to the medium may be 0 to 2:1 to 2. Preferably, the ratio of glucose:galactose to be added to the medium may be 0.5 to 1.5:1.5 to 2. More preferably, the ratio of glucose:galactose to be added to the medium may be 1:2. In other words, when the recombinant vector for expressing brazzein is a pESC-URA vector, the ratio of glucose/galactose to be added to the medium may be 0.1 to 2, preferably, the ratio of glucose/galactose may be 0.1 to 1, and more preferably, the ratio of glucose/galactose may be 0.2 to 0.7.

Furthermore, in the present invention, the inducer may be added at the lag phase, log phase, or stationary phase. The "lag phase" generally refers to a time period when a strain is inoculated into a culture solution, and then acclimatized, the "log phase" generally refers to a time period when a strain most actively grows and divides, and the "stationary phase" generally refers to a time period when the growth of a strain is stopped. Preferably, the inducer may be added at the log phase or stationary phase, and may be added most preferably at the log phase.

For a method for isolating the brazzein according to the present invention from a culture of the transformed strain, the brazzein can be isolated by various isolation and purification methods used in the art. That is, brazzein may be isolated by applying techniques such as salting out (ammonium sulfate precipitation and sodium phosphate precipitation), solvent precipitation (protein fraction precipitation using acetone, ethanol, and the like), dialysis, gel filtration, ion exchange chromatography, reverse phase column chromatography and affinity chromatography alone or in combination, and in addition, any protein purification method known in the art can be applied without limitation.

For example, in the present invention, the purifying step in Step (4) may be purifying brazzein by cation exchange resin chromatography. Alternatively, the purifying step in Step (4) may be purifying brazzein by cation exchange resin chromatography after adjusting the pH of the culture solution of the transformed strain. The cation exchange resin chromatography may be CM-Sepharose chromatography.

However, preferably, the purifying step in Step (4) may be purifying brazzein by ultrafiltration. That is, the method for purifying brazzein according to the present invention can also purify brazzein using protein purification methods such as cation chromatography such as CM Sepharose chromatography, anion chromatography, hydrophobic chromatography, or gel filtration, and preferably, may be characterized by purifying brazzein more simply by ultrafiltration. Therefore, the method for mass-producing brazzein according to the present invention can economically and efficiently mass-produce and purify brazzein because high-cost CM Sepharose chromatography is not required in the purification process.

Further, in the present invention, in the purifying of brazzein, a desalting process may be performed before brazzein is purified by ultrafiltration, and when a culture subjected to the desalting process is purified by ultrafiltration, brazzein having higher purity and yield may be obtained.

In addition, the present invention provides a composition for mass-producing brazzein, a food composition, a health functional food, a cosmetic composition and/or a feed additive, including the *Saccharomyces cerevisiae* strain for expressing brazzein according to the present invention, a culture thereof, or a mixture thereof.

The *Saccharomyces cerevisiae* strain for expressing brazzein according to the present invention, a culture thereof, or a mixture thereof according to the present invention may be used by adding the *Saccharomyces cerevisiae* strain for expressing brazzein according to the present invention, a culture thereof, or a mixture thereof as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the *Saccharomyces cerevisiae* strain for expressing brazzein according to the present invention, a culture thereof, or a mixture thereof of the present invention is added in an amount of 15 wt % or less, preferably 10 wt % or less based on the raw materials. However, for long-term intake for the purpose of health and hygiene or for the purpose of health control, the amount may be less than the above-mentioned range, and the vesicles have no problem in terms of stability, so the active ingredient may be used in an amount more than the above-mentioned range.

The type of food is not particularly limited. Examples of food to which the material may be added include meats, sausage, bread, chocolate, candies, snacks, confectioneries, pizza, instant noodles, other noodles, gums, dairy products including ice creams, various soups, beverages, tea, drinks, alcoholic beverages, vitamin complexes, and the like, and include all health functional foods in a typical sense.

The health beverage composition according to the present invention may contain various flavors or natural carbohydrates, and the like as additional ingredients as in a typical beverage. The above-described natural carbohydrates may be monosaccharides such as glucose and fructose, disaccharides such as maltose and sucrose, polysaccharides such as dextrin and cyclodextrin, and sugar alcohols such as xylitol, sorbitol, and erythritol. As a sweetener, it is possible to use a natural sweetener such as thaumatin and stevia extract, a synthetic sweetener such as saccharin and aspartame, and the like. The proportion of the natural carbohydrates is generally about 0.01 to 0.20 g, or about 0.04 to 0.10 g per 100 ml of the composition of the present invention.

In addition to the aforementioned ingredients, the composition of the present invention may contain various nutrients, vitamins, electrolytes, flavors, colorants, pectic acids and salts thereof, alginic acid and salts thereof, organic acids, protective colloid thickeners, pH adjusters, stabilizers, preservatives, glycerin, alcohols, carbonating agents used in carbonated drinks, and the like. In addition, the composition of the present invention may contain flesh for preparing natural fruit juice, fruit juice drinks, and vegetable drinks. These ingredients may be used either alone or in combinations thereof. The proportion of these additives is not significantly important, but is generally selected within a range of 0.01 to 0.20 part by weight per 100 parts by weight of the composition of the present invention.

As used herein, the "health functional food" is the same term as a food for special health use (FoSHU), and refers to a food having high medical and medicinal effects processed to exhibit biological regulation functions with efficiency, in addition to nutritional supply, and the food may be prepared in various forms such as tablets, capsules, powders, granules, liquids and pills.

The health functional food can be prepared by a method typically used in the art, and may be prepared by adding raw materials and components typically added in the art during preparation. Furthermore, the health functional food has an advantage of having no side effects which may occur when the drug is collected for a long period of time because food is used as a raw material unlike general drugs, and may be excellent in portability.

A formulation for the cosmetic composition according to the present invention may include a skin lotion, a skin softener, a skin toner, an astringent, a lotion, a milk lotion, a moisturizing lotion, a nourishing lotion, a massage cream, a nourishing cream, a mist, a moisturizing cream, a hand cream, a hand lotion, a foundation, an essence, a nourishing essence, a pack, soap, a cleansing foam, a cleansing lotion, a cleansing cream, a cleansing oil, a cleansing balm, a body lotion or a body cleanser.

A cosmetic composition of the present invention may further include a composition selected from the group consisting of water-soluble vitamins, oil-soluble vitamins, polymer peptides, polymeric polysaccharides, and sphingolipids.

The water-soluble vitamin may be any substance that is blendable with cosmetics, but examples thereof include vitamin B1, vitamin B2, vitamin B6, pyridoxine, pyridoxine hydrochloride, vitamin B12, pantothenic acid, nicotinic acid, nicotinic acid amide, folic acid, vitamin C, vitamin H, and the like, and salts thereof (thiamine hydrochloride, sodium ascorbate, and the like) or derivatives thereof (sodium ascorbic acid-2-phosphate, magnesium ascorbic acid-2-phosphate, and the like) are also included in water-soluble vitamins that may be used in the present invention. These water-soluble vitamins may be obtained by a conventional method such as microbial transformation, purification from a microbial culture, an enzyme method, or a chemical synthesis method.

The oil-soluble vitamins may be any substance that is blendable with cosmetics, but examples thereof include vitamin A, carotene, vitamin D2, vitamin D3, vitamin E (dl-$\alpha$-tocopherol, d-$\alpha$-tocopherol), or the like, and derivatives thereof (e.g., ascorbyl palmitate, ascorbyl stearate, ascorbyl dipalmitate, dl-$\alpha$-tocopherol acetate, dl-$\alpha$-tocopherol nicotinate, vitamin E, DL-pantothenyl alcohol, D-pantothenyl alcohol, pantothenyl ethylether) may also be included in the oil-soluble vitamins used in the present invention. These oil-soluble vitamins may be obtained by a conventional method such as microbial transformation, purification from a microbial culture, or enzymatic or chemical synthesis.

The polymer peptides may be any substance that is blendable with cosmetics, but examples thereof may include collagen, hydrolyzed collagen, gelatin, elastin, hydrolyzed elastin, and keratin. The polymer peptides may be purified and obtained by any conventional method such as purification from a microbial culture, an enzyme method, or a chemical synthesis method, or may generally be used by being purified from natural substances such as the dermis of a pig, a cow, or the like and silk fiber of silkworms.

The polymeric polysaccharides may be any substance that is blendable with cosmetics, and examples thereof may include hydroxyethyl cellulose, xanthan gum, sodium hyaluronate, and chondroitin sulfate or salts thereof (sodium salts). For example, chondroitin sulfate or salts thereof may generally be purified from mammals or fish and used.

The sphingolipids may be any substance that is blendable with cosmetics, and examples thereof may include ceramide, phytosphingosine, and sphingoglycolipid. The sphingolipids may be purified, by a conventional method, from mammals, fish, shellfish, yeast, or plants, or may be obtained by a chemical synthesis method.

The cosmetic composition of the present invention may include, as necessary, other ingredients mixed in conventional cosmetics along with the above essential ingredients.

Examples of additional ingredients to be mixed may include lipid components, a humectant, an emollient, a surfactant, organic and inorganic pigments, organic powder, a UV absorbent, a preservative, a sanitizer, an antioxidant, a plant extract, a pH adjuster, alcohol, pigments, flavors, a blood circulation promoter, a cooling agent, an anti-diaphoretic, and purified water.

The lipid components may include, for example, ester lipids, hydrocarbon lipids, silicone lipids, fluorine lipids, animal fats, vegetable oil, or the like.

The ester lipids may include, for example, glyceryl tri 2-ethylhexanoate, cetyl 2-ethylhexanoate, isopropyl myristate, butyl myristate, isopropyl palmitate, ethyl stearate, octyl palmitate, isocetyl isostearate, butyl stearate, ethyl linolate, isopropyl linolate, ethyl oleate, isocetyl myristate, isostearyl myristate, isostearyl palmitate, octyldodecyl myristate, isocetyl isostearate, diethyl sebacate, diisopropyl adipate, isoalkyl neopentanate, tri(capryl, capric acid)glyceryl, trimethylolpropane tri 2-ethylhexanoate, trimethylolpropane triisostearate, pentaerythritol tetra 2-ethylhexanoate, cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl palmitate, octyl stearate, isocetyl stearate, isodecyl oleate, octyldodecyl oleate, octyldodecyl linolate, isopropyl isostearate, cetostearyl 2-ethylhexanoate, stearyl 2-ethylhexanoate, hexyl isostearate, ethyleneglycol dioctanoate, ethyleneglycol dioleate, propyleneglycol dicaprinate, propyleneglycol di(caprylate, caprinate), propyleneglycol dicaprylate, neopentylglycol dicaprinate, neopentylglycol dioctanoate, glyceryl tricaprylate, glyceryl triundecylate, glyceryl triisopalmitate, glyceryl triisostearate, octyldodecyl neopentanoate, isostearyl octanoate, octyl isononanoate, hexyldecyl neodecanoate, octyldodecyl neodecanoate, isocetyl isostearate, isostearyl isostearate, octyldecyl isostearate, polyglycerin ester oleate, polyglycerin ester isostearate, triisocetyl citrate, triisoalkyl citrate, triisooctyl citrate, lauryl lactate, myristyl lactate, cetyl lactate, octyldecyl lactate, triethyl citrate, acetyltriethyl citrate, acetyltributyl citrate, trioctyl citrate, diisostearyl malate, 2-ethylhexyl hydroxystearate, di 2-ethylhexyl succinate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoyl hydroxystearate, stearoyl 12-stearoyl hydroxystearate, isostearyl 12-stearoyl hydroxystearate, and the like.

The hydrocarbon lipids may include, for example, squalene, liquid paraffin, alpha-olefin oligomers, isoparaffin, ceresine, paraffin, liquid isoparaffin, polybutene, microcrystalline wax, Vaseline, and the like.

The silicone lipids may include, for example, polymethyl silicon, methylphenyl silicon, methyl cyclopolysiloxane, octamethyl polysiloxane, decamethyl polysiloxane, dodecamethyl cyclosiloxane, dimethylsiloxane/methylcetyloxysiloxane copolymers, dimethylsiloxane/methylstearoxysiloxane copolymers, alkyl-modified silicon oil, amino-modified silicon oil, and the like.

The fluorine lipids may include perfluoropolyether and the like.

The animal or vegetable oil may include avocado oil, almond oil, olive oil, sesame oil, rice bran oil, safflower oil, soybean oil, corn oil, rape flower oil, apricot kernel oil, palm kernel oil, palm oil, castor oil, sunflower oil, grape seed oil, cotton seed oil, coconut oil, tallow nut oil, wheat germ oil, rice germ oil, Shea butter, evening primrose oil, macadamia nut oil, meadow foam seed oil, yolk oil, beef tallow, hemp seed oil, mink oil, orange roughy oil, jojoba oil, candelilla wax, carnauba wax, liquid lanolin, dehydrated castor oil, and the like.

The humectant may include water-soluble low molecular humectants, oil-soluble molecular humectants, water-soluble polymers, oil-soluble polymers, and the like.

The water-soluble low molecular humectants may include serine, glutamine, sorbitol, mannitol, pyrrolidone-sodium carboxylate, glycerin, propylene glycol, 1,3-butylene glycol, ethylene glycol, polyethylene glycol B (degree of polymerization: n=2 or higher), polypropylene glycol (degree of polymerization: n=2 or higher), polyglycerin B (degree of polymerization: n=2 or higher), lactic acid, lactates, and the like.

The oil-soluble low molecular humectants may include cholesterol, cholesterol ester, and the like.

The water-soluble polymers may include carboxyvinyl polymers, polyasparaginic acid salts, tragacanth, xanthan gum, methyl cellulose, hydroxymethyl cellulose, hydroxylethyl cellulose, hydroxypropyl cellulose, carboxymethyl cellulose, water-soluble chitin, chitosan, dextrin, and the like.

The oil-soluble polymers may include, for example, polyvinyl pyrrolidone/eicosen copolymers, polyvinyl pyrrolidone/hexadecene copolymers, nitrocellulose, dextrin fatty acid ester, silicone polymers, and the like.

The emollients may include, for example, long chain cholesterylester acyl glutamate, cholesteryl hydroxystearate, 12-hydroxystearic acid, stearic acid, rosin acid, lanolin fatty acid cholesteryl ester, and the like.

The surfactants may include, for example, non-ionic surfactants, anionic surfactants, cationic surfactants, amphoteric surfactants, and the like.

The non-ionic surfactants may include self-emulsion type glycerin monostearate, propyleneglycol fatty acid ester, glycerin fatty acid ester, polyglycerin fatty acid ester, sorbitan fatty acid ester, polyoxyethylene (POE) sorbitan fatty acid ester, POE sorbit fatty acid ester, POE glycerin fatty acid ester, POE alkylethers, POE fatty acid ester, POE dehydrated castor oil, POE castor oil, polyoxyethylene/polyoxypropylene (POE/POP) copolymers, POE/POP alkylethers, polyether-modified silicone, alkanolamide laurate, alkylamine oxide, hydrated soy phospholipids, and the like.

The anionic surfactants may include fatty acid soap, α-acylsulfonate, alkyl sulfonates, alkylallyl sulfonates, alkylnaphthalene sulfonates, alkyl sulfates, POE alkylether sulfates, alkylamide sulfates, alkyl phosphates, POE alkyl phosphates, alkylamide phosphates, alkyloyl alkyltaurin salts, N-acylamino acid salts, POE alkylether carboxylates, alkyl sulfosuccinates, sodium alkyl sulfoacetates, acylated hydrolyzed collagen peptide salts, perfluoroalkyl ester phosphates, and the like.

The cationic surfactants may include, for example, alkyltrimethylammonium chloride, stearyltrimethylammonium chloride, steraryltrimethylammonium bromide, cetostearyl trimethylammonium chloride, distearyl dimethylammonium chloride, stearylaryl dimethylbenzylammonium chloride, behenyltrimethylammonium bromide, benzalkonium chloride, diethylaminoethylamide stearate, dimethylaminopropylamide stearate, quaternary ammonium salts of lanolin derivatives, and the like.

The amphoteric surfactants may include carboxybetaine, amidebetaine, sulfobetaine, hydroxysulfobetaine, amidesulfobetaine, phosphobetaine, aminocarboxylate, imidazoline derivatives, amideamine-based amphoteric surfactants, and the like.

The organic and inorganic pigments may include: inorganic pigments such as silicic acid, anhydrous silicic acid, magnesium silicate, talc, sericite, mica, kaolin, bengala, clay, bentonite, titanium dioxide-coated mica, bismuth oxychloride, zirconium oxide, magnesium oxide, zinc oxide, titanium oxide, aluminum oxide, calcium sulfate, barium sulfate, magnesium sulfate, calcium carbonate, magnesium carbonate, iron oxide, ultramarine, chromium oxide, chromium hydroxide, calamine, and combinations thereof: organic pigments such as polyamide, polyester, polypropylene, polystyrene, polyurethane, vinyl resin, urea resin, phenol resin, fluorine resin, silicon resin, acryl resin, melamine resin, epoxy resin, polycarbonate resin, divinyl benzene/ styrene copolymers, silk powder, cellulose, CI pigment yellow, and CI pigment orange: and composite pigments of inorganic and organic pigments.

The organic powder may include: metallic soap such as calcium stearate; metal salts of alkyl phosphoric acid such as zinc sodium cetylate, zinc laurylate, and calcium laurylate; polymetallic salts of acylamino acid such as calcium N-lauroyl-beta-alanine, zinc N-lauroyl-beta-alanine, and calcium N-lauroylglycine; polymetallic salts of amide sulfonates such as calcium N-lauroyl-taurine and calcium N-palmitoyl-taurine; N-acyl alkaline amino acids such as N-epsilon-lauroyl-L-lysine, N-epsilon-palmitoyl lysine, N-α-palmitoylol nitin, N-α-lauroyl arginine, and N-α-dehydrated tallow fatty acid acyl arginine; N-acyl polypeptides such as N-lauroyl glycylglycine; α-amino fatty acids such as α-aminocaprylic acid and α-aminolauric acid; polyethylene; polypropylene; nylon; polymethylmethacrylate; polystyrene; divinylbenzene/styrene copolymers; ethylene tetrafluoride; and the like.

The UV absorbents may include para-aminobenzoic acid, ethyl para-aminobenzoate, amyl para-aminobenzoate, octyl para-aminobenzoate, ethyleneglycol salicylate, phenyl salicylate, octyl salcylate, benzyl salicylate, butylphenyl salicylate, homomentyl salicylate, benzyl cinnamate, paramethoxycinnamic acid-2-ethoxylethyl, octyl paramethoxycinnamate, mono-2-ethylhexaneglyceryl diparamethoxycinnamate, isopropyl paramethoxycinnamate, diisopropyl/ diisopropyl cinnamic acid ester mixtures, urocanic acid, ethyl urocanate, hydroxymethoxybenzophenone, hydroxymethoxybenzophenone sulfonic acid and salts thereof, dihydroxymethoxy benzophenone, sodium dihydroxymethoxy benzophenone disulfonate, dihydroxy benzophenone, tetrahydroxy benzophenone, 4-tert-butyl-4'-methoxydibenzoylmethane, 2,4,6-trianilino-p-(carbo-2'-ethylhexyl-1'-oxy)-1,3,5-triazine, 2-(2-hydroxy-5-methylphenyl)benzotriazole, and the like.

The sanitizers may include hinokitiol, trichloric acid, trichlorohydroxydiphenylether, chlorohexidine gluconate, phenoxyethanol, resorcine, isopropylmethylphenol, azulene, salicylic acid, zinc pyrithione, benzalkonium chloride, light sensitive element No. 301, sodium mononitroguaiacol, undecylenic acid, and the like.

The antioxidants may include butylhydroxyanisole, propyl gallate, elisorbic acid, and the like.

The pH adjusters may include citric acid, sodium citrate, malic acid, sodium malate, fumaric acid, sodium fumarate, succinic acid, sodium succinate, sodium hydroxide, sodium monohydrophosphate, and the like.

The alcohols may include higher alcohols such as cetyl alcohol.

In addition, additional ingredients to be mixed are not limited to the above examples, and any one of the above ingredients may be mixed within a range that does not adversely affect the objectives and effects of the present invention, but may range from 0.01 wt % to 5 wt % or 0.01 wt % to 3 wt % with respect to the total weight of the composition.

For lotion, paste, cream, or gel preparations of the present invention, as a carrier ingredient, animal fiber, vegetable fiber, wax, paraffin, starch, tragacanth, a cellulose derivative, polyethylene glycol, silicon, bentonite, silica, talc, zinc oxide, or the like may be used.

For powder or spray preparations of the present invention, lactose, talc, silica, aluminum hydroxide, calcium silicate, or polyamide powder may be used as a carrier ingredient. In particular, in the case of spray preparations, the composition may further include a propellant such as chlorofluorohydrocarbon, propane/butane, or dimethyl ether.

For solution or emulsion preparations of the present invention, a solvent, a solubilizing agent, or an emulsifying agent may be used as a carrier ingredient, and the carrier ingredient may be, for example, water, ethanol, isopropanol, ethyl carbonate, ethyl acetate, benzyl alcohol, benzyl benzoate, propylene glycol, 1,3-butyl glycol oil, a glycerol aliphatic ester, polyethylene glycol, or a sorbitan fatty acid ester.

For suspension preparations of the present invention, as a carrier ingredient, a liquid diluent such as water, ethanol, or propylene glycol, a suspending agent such as ethoxylated isostearyl alcohol, polyoxyethylene sorbitol ester, or polyoxyethylene sorbitan ester, micro-crystalline cellulose, aluminum methahydroxide, bentonite, agar, tragacanth, or the like may be used.

For surfactant-containing cleansing preparations of the present invention, as a carrier ingredient, an aliphatic alcohol sulfate, an aliphatic alcohol ether sulfate, a sulfosuccinate monoester, isethionate, imidazolinium derivatives, methyltaurate, sarcosinate, fatty acid amide ether sulfate, alkylamidobetaine, an aliphatic alcohol, a fatty acid glyceride, a fatty acid diethanol amide, vegetable oil, a lanolin derivative, an ethoxylated glycerol fatty acid ester, or the like may be used.

The health functional food has an advantage of having a better effect by being ingested in the form of an inner beauty food. The inner beauty food is a food called 'edible cosmetic or beauty food', and refers to a food that changes the constitution of the skin to be healthy by absorbing various components that are good for the skin into the body, and an inner beauty food that suits each individual may be selected and ingested in consideration of skin conditions and lifestyles as when a cosmetic that suits the skin type is chosen. For example, when a cosmetic including the cosmetic composition is used in a mixture with an inner beauty food including the *Saccharomyces cerevisiae* strain for expressing brazzein, a culture thereof, or a mixture thereof, the effect is remarkably enhanced compared to using only a cosmetic or a medicament, so that it is possible to have an advantage capable of observing a more effective skin-beautifying effect.

As used herein, the "feed" may refer to any natural or artificial diet, one-meal, and the like, or a component of the one-meal for an animal to eat, ingest, and digest, or suitable for that. The type of feed described above is not particularly limited, and a feed typically used in the art may be used. The feed composition may include a feed additive. As used herein, the "feed additive" corresponds to a supplementary material under the Control of Livestock and Fish Feed Act, and may include a probiotic agent. Non-limiting examples of the feed include vegetable feeds such as cereals, roots and fruits, food processing by-products, algae, fibers, pharmaceutical by-products, fats and oils, starches, gourds or grain by-products: and animal feeds such as proteins, inorganic substances, minerals, single cell proteins, animal plankton or foods. These feeds may be used alone or in mixtures of two or more thereof.

Hereinafter, preferred examples for helping the understanding of the present invention will be suggested. However, the following examples are provided only to more easily understand the present invention, and the contents of the present invention are not limited by the following examples.

[Apparatuses and Reagents]
1. Apparatuses

The VB-125A60 autoclave and VB-700H1 clean bench from VISIONBIOTECH (Incheon, Korea) were used as a clean bench for handling high-pressure sterilization and bacteria, a shaking incubator from Vision Scientific Co., Ltd. (Gyeonggi, Korea) was used in order to culture bacteria, and Micro-12, Smart-R17, Supra R30 from Hanil Scientific Inc. were used as centrifuges for collecting bacterial cells. VCX 400 from Sonics & Materials Inc. (Danbury, USA) was used as a sonicator for pulverizing bacterial cells, and KMC-1300V from Vision Scientific Co., Ltd. (Gyeonggi, Korea) was used as a vortex mixer.

Orion Star A211 from Thermo Scientific (Pittsburgh, PA, USA) was used as a pH meter, MS300 Hotplate & Magnetic Stirrer from MTOPS (Misung Scientific Co., Ltd.) was used as a stirrer, and U-2000 UV/VIS Spectrophotometer from Hitachi, Ltd. (Tokyo, Japan) was used for protein quantification. Pump P-1 from Pharmacia Biotech Inc. (Uppsala, Sweden) was used as a peristatic pump for protein quantification, and Fraction Collector FRAC-100 was used as a fraction collector. TFD5505 Freeze Dryer and DF8503S Ultra Low Temperature Freezer from Ilshin Lab Co. (Gyeonggi, Korea) were used as a freeze dryer and an ultra-low temperature freezer. The NA-1010 Protein Electrophoresis device from EIDO Co., Ltd. (Tokyo, Japan) was used as a protein electrophoresis apparatus.

QuantStudio 3 from Thermo (Waltham, USA) was used as a real-time polymerase chain reaction (qRT-PCR) apparatus. Cosmo Genetech Co., Ltd. (Seoul, Korea) and Bionics Co., Ltd. (Seoul, Korea) were commissioned to perform DNA synthesis, and Bionics Co., Ltd. (Seoul, Korea) was commissioned to perform base sequence analysis.

2. Reagents

Products from Difco Laboratories Inc. (Sparks, USA) were purchased and used as a bacto yeast extract, bacto tryptone, bacto agar, and bacto peptone for strain culture, and 'yeast nitrogen base without amino acids and ammonium sulfate' for a selection medium after transformation was purchased from Difco Laboratories Inc. (Sparks, MD).

A product from Cosmo Genetech Co., Ltd. (Seoul, Korea) was used as a plasmid miniprep kit for DNA purification, and a product from Bionics Co., Ltd. (Seoul, Korea) was used as a total DNA extract kit. In addition, products from Sigma Chemical Co. (St. Louis, USA) were used as agarose, N,N,N'N'-tetramethylethylenediamine (TEMED), sodium lauryl sulfate (SDS), and glycerol, and products from Bio-Rad Laboratories, Inc. (Hercules, USA) were used as a 30% acryl amide solution, a polypeptide protein marker, and Coomassie brilliant blue R-250. Products from Kanto Chemical Co. (Tokyo, Japan) were used as potassium phosphate (monobasic) and potassium phosphate (dibasic). SYBR® Green Real-Time PCR Master Mix from Thermo Fisher Scientific Inc. (Waltham, MA USA) was used as SYBR used for Real-time PCR.

A product from GE Healthcare (Buckinghamshire, UK) was used as a CM Sepharose resin during protein purification. A product from Pierce Chemical Co. (Rockford, IL, USA) was used as a BSA protein assay kit for BCA quantification. As other reagents for making buffers and all reagents used, extra pure-grade and guaranteed-grade reagents were used.

3. Expression Vectors and Strains

One shot TOP10 E. coli with high efficiency of multiple replication plasmids was purchased from Invitrogen™ (California, USA) as a strain for vector replication.

The present inventors constructed a total of six types of expression systems by transforming three strains for expression with two types of expression vectors consisting of a yeast episomal plasmid in order to increase the expression level of recombinant brazzein. Three types, INVSc1, Y2805, and BY4741 used for food and mass production, were used as strains (Table 1), and pESC-URA including a GAL promoter and pD1214-FAKs including a TEF promoter were used as vectors (Table 2). All S. cerevisiae INVSc1, Y2805, and BY4741 strains are uracil auxotrophic mutants (ura3-52, ura340). An expression vector was constructed using BamH I and Hind III restriction enzymes in the vector pESC-URA and using XhoI as a restriction enzyme in the vector pD1214-FAKS to insert genes of wild type brazzein and variant 3M-K5R. TOP10 was used as an E. coli host cell for plasmid construction and amplification.

Furthermore, in order to compare the copy numbers of the transformants using quantitative RT-PCR, a host cell in which the URA3 gene was inserted into genomic DNA with one-copy number was used (Yoo, Sohn, Jeong, & Kang, 2020).

TABLE 1

S. cerevisiae strains used in the present invention

| Strain | Relevant genotype | Source |
|---|---|---|
| INVSc1 | MATα his3-Δ1 leu2 trp1-289 ura3-52 | Invitrogen |
| Y2805 | MATα pep::HIS3 prb-Δ1.6R can1 his3-20 ura3-52 | (Choi, Sohn, & Rhee, 1994) |
| BY4741 | MATα his3Δ1 leu2Δ0 met15Δ0 ura3Δ0 | ATCC201388 |
| Scmet4Δ::ScMET4 | MATα ura3-52 leu2-3, 112 his4-34 met4::MET4$^{HA}$ LEU2 URA3 | (Yoo et al., 2020) |

TABLE 2

Vectors used in the present invention

| Plasmid | Relevant genotype | Sources |
|---|---|---|
| pD1214-FAks | SS-Alphafactor(full, KEX, STE) URA3 PTEF | ATUM(Newark, California, USA) |
| pESC-URA | E. coli-S. cerevisiae shuttle vector; URA3 PGAL1 PGAL10 Ap$^r$ | Stratagene, La Jolla, CA, USA |

Ap$^r$, ampicillin resistance

4. Media

An LB (1% tryptone, 0.5% yeast extract, 1% NaCl) medium was used for E. coli culture, and a concentration of 50 mg/L was used when ampicillin was used.

A complex medium YPD (1% yeast extract, 2% peptone, 2% glucose) or a synthetic medium YNB (0.67% yeast nitrogen base w/o amino acid and ammonium sulfate, 0.2% glucose) was used for yeast culture.

An LB amp plate (1.5% agar and 50 mg/L ampicillin in LB medium) was used for E. coli transformation, and a YNB plate (1.5% agar in YNB medium) was used for yeast transformation.

[Experimental Examples]

Experimental Example 1. Design of expression vector and selection of expression strain 1-1. Design of Expression Vector Two types of expression vectors with different promoters were constructed in order to compare the expression levels of recombinant brazzein. In this case, a brazzein gene optimized for S. cerevisiae was prepared in order to increase the expression efficiency of recombinant brazzein in *S. cerevisiae*, so that DNA was synthesized in consideration of a codon usage suitable for *S. cerevisiae* within a range not changing the amino acid sequence based on a brazzein DNA sequence of *Pentadiplandra brazzeana* Baillon, and the DNA sequence was represented by SEQ ID NO: 2 (FIG. 1).

Further, recombinant brazzein was designed to be secreted and expressed outside the colony by linking the α-mating factor signal sequence to the brazzein sequence for efficient purification. Since the α-mating factor is not present in the pESC-URA vector, an α-mating factor sequence of pKLAC2 of *K. lactis* used in a prior study (Jo et al., 2013) was optimized with a codon corresponding to *S. cerevisiae*, synthesized by Bionics Co., Ltd. (Seoul, Korea) and brazzein was inserted downstream of the Kex cleavage site (left side in FIG. 2), and since the α-mating factor is present in the pD1214-FAKS expression vector, cleavage by the Xho I restriction enzyme was performed, and then a codon-optimized brazzein sequence was inserted thereinto (right side in FIG. 2). A DNA sequence of an α-mating factor signal sequence optimized for *S. cerevisiae* was represented by SEQ ID NO: 5, and an amino acid sequence was represented by SEQ ID NO: 6.

Consequently, a pESC-Brazzein plasmid (SEQ ID NO: 10) in which a recombinant brazzein gene and an α-mating factor were inserted into a pESC-URA vector and a pD1214-Brazzein plasmid (SEQ ID NO: 11) in which a recombinant brazzein gene and an α-mating factor were inserted into a pD1214-FAKs vector were prepared.

1-2. Transformation into *E. coli* TOP 10 for Expression Vector Amplification

In order to obtain a large amount of pD1214-FAKS-Brazzein and pESC-URA-Brazzein expression vectors into which the synthesized brazzein sequence was inserted, the vectors were transformed into *E. coli* TOP10 capable of highly efficient and stable replication. The method is as follows:

After TOP 10 bacteria were cultured at 37° C. in an LB liquid medium overnight, a 1/100 volume of the culture solution thereof was inoculated into a new LB liquid medium and cultured at 37° C. until 4-7×10 cells/ml. After the culture solution was cooled on ice for 10 to 15 minutes, bacteria were collected by centrifugation at 3,000 g for 15 minutes, and competent cells were prepared using 50 mM $CaCl_2$). 1 μl of the pD1214-FAKS and pESC-URA expression vectors was added thereto, a thermal shock was applied at 42° ° C. for 2 minutes, and the cells were allowed to have a recovery stage in a super optimal broth (S.O.C) medium (yeast extract 0.5%, 10 mM $MgCl_2$, 10 mM MgSO4, and 20 mM glucose), and then streaked on an LB solid medium containing 50 μl/ml ampicillin, and cultured at 37° ° C. for 12 hours. Single colonies were collected and cultured in an LB liquid medium containing the antibiotic ampicillin, and DNA was purified using a plasmid miniprep kit (Cosmo Genetech Co., Ltd., Korea).

1-3. Vector Transformation into *Saccharomyces cerevisiae* Strain

In order to transform *S. cerevisiae* strains INVSc1, Y2805, and BY474 with the expression vector previously constructed, competent cells were prepared. Transformation was performed by a method of using lithium acetate in yeast cells grown in a YPD medium to have an $OD_{600}$ of 0.7 (Gietz & Schiestl, 2007). Transformed cells were streaked on a solid medium of a synthetic complete medium (SC-Ura) (0.67 g/L yeast nitrogen base w/o amino acid and ammonium sulfate, 0.77 g/L of a complete supplement mixture, 5 g/L ammonium sulfate and 2% glucose) which does not contain uracil, which is an auxotrophic marker of the strain, and were cultured at 30° ° C. for 3 days.

Among the host strains of *S. cerevisiae*, BY4741, INVSc1 and Y2805, which are widely used in the food field, were used as the transformed yeast strains. In these strains, genes required for uracil synthesis are deleted or modified. However, since the expression vectors include the URA3 gene capable of synthesizing uracil, a transformant in which a target gene is inserted into a *S. cerevisiae* genome can be grown in a uracil deficient medium.

1-4. Total DNA Extraction from Transformed *S. cerevisiae*

10 to 20 colonies grown on a *S. cerevisiae* SC-Ura agar plate were selected and cultured at 30° ° C. in a YPD (1% yeast extract, 2% bacto peptone, 2% glucose) liquid medium for 16 to 18 hours. For long-term storage, samples in which each colony was liquid-cultured were made into a 20% glycerol stock state and stored frozen at −70° C. The samples were separately aliquoted by 1 ml and centrifuged to collect only the bacteria, the bacterial cells were pulverized with glass beads, and then total DNA was extracted using a total DNA kit.

1-5. Quantitative Real-Time PCR (qRT-PCR)

Yeast cells have different numbers of genes to be inserted depending on each cell and the transformation method when a desired gene is transformed. For example, in the case of YIp and YEp, up to 10 copy numbers and 50 to 100 copy numbers or more may be inserted, respectively (Gnugge & Rudolf, 2017). Therefore, quantitative real-time PCR was performed to determine the copy number of the brazzein gene inserted into the *S. cerevisiae* strain.

When total DNA is extracted from transformed bacteria, genomic DNA and plasmid DNA are present together. Since one gene for each of the marker gene URA3 and a desired gene brazzein sequence is inserted into each of the vectors inserted into the strain, a URA3 primer was used instead of a brazzein primer. Since the present inventors do not have cells that contain brazzein as one copy, the present inventors tried to quantify the copy number of the brazzein gene contained in the transformed yeast using Scmet4Δ::Sc-MET4, which has about one copy of the URA3 gene in the chromosome. In this case, an ACTI gene was used as a housekeeping gene. The sequences of the used primers are shown in Table 3.

TABLE 3

| Primer | sequence | Tm value |
|---|---|---|
| ScACT1 Forward (SEQ ID NO: 16) | 5'-ATT GCC GAA AGA ATG CAA AAG G-3' | 55.0 |
| ScACT1 Reverse (SEQ ID NO: 17) | 5'-GAA CCA CCA ATC CAG ACG GAG T-3' | 60.5 |
| ScURA3 Forward (SEQ ID NO: 18) | 5'-TCC ACC CAT GTC TCT TTG AGC A-3' | 58.9 |
| ScURA3 Reverse (SEQ ID NO: 19) | 5'-AGA ATT GTC ATG CAA GGG CTC C-3' | 59.4 |

Polymerase chain reaction (PCR) was performed under the following conditions (Table 4): performed at 95° C. for 10 seconds, at 52° C. for 15 seconds, and at 72° C. for 15 seconds, and performed on each PCR sample in triplicate. Melting point analysis was performed by increasing the temperature 0.5° C. every 5 seconds from 65° ° C. to 95° ° C. Since the Tm values of the primers used were ACTI forward primer 55° C., ACTI reverse primer 60.5° C., URA3 forward primer 58.9° C., and URA3 reverse primer 59.4° C., the melting point analysis was performed at an annealing temperature of 52° C. proceeded at 52° C., which is 2 to 3° C. lower than the lowest Tm value of 55° C.

TABLE 4

PCR conditions for qRT-PCR of brazzein gene

| Steps | Temperature | Time |
|---|---|---|
| Pre-incubation (for UDG) | 50° C. | 2 min |
| Initial denaturation | 95° C. | 10 min |
| Denaturation | 95° C. | 10 sec |
| Annealing | 52° C. | 15 sec |
| Elongation | 72° C. | 15 sec |
| Number of cycels | | 40 cycles |

An initial denaturation time of at least 10 minutes is required to completely activate a PCR DNA polymerase.

The total DNA concentration was quantified by UV and adjusted to the same level, but did not deviate from the 10 to 100 ng/μl concentration range where real-time PCR (RT-PCR) can be performed. A final volume of 15 μl was prepared by adding 7 μl of SYBR® Green Real-Time Master Mix, 1 μl of each of the forward primer and the reverse primer, 5 μl of distilled water and 1 μl of total DNA to a PCR tube. The PCR reaction was performed with Bio-Rad CFX 96 Real Time PCR. A comparative CT (AA CT) method was used in order to analyze the relative expression level of the gene (Livak & Schmittgen, 2001).

1-6. Confirmation of Bacterial Cell Concentration and Plasmid Stability

Plasmid stability, which indicates how much the inserted plasmid drops out by culture, was confirmed using two methods of a method of measuring the number of colonies by respectively sub-culturing the inserted plasmid on YPD and SD-Ura solid media; and a method of quantifying the dropout rate of the plasmid by analysis by qRT-PCR.

In the case of the confirmation method by subculture, after the transformed bacterial cells were inoculated into YPD, a small amount of the culture solution collected every 24 hours was aliquoted, and then diluted at an appropriate ratio to adjust the bacterial cell concentration, the absorbance ($OD_{600}$) at 600 nm was measured using a spectrophotometer, and after the culture solution was streaked, the number of colonies formed after 3 days was measured. As the method using qRT-PCR, the same method as in Experimental Example 1-5 was used.

1-7. Selection of Expression Vector and Strain

The present inventors prepared expression systems of pD1214-Brazzein/INVSc1, pESC-Brazzein/INVSc1, pD1214-Brazzein/Y2805, pESC-Brazzein/Y2805, pD1214-Brazzein/BY4741, and pESC-Brazzein/BY4741 by transforming three types of strains with two expression vectors, pD1214-Brazzein which is a constitutive promoter and pESC-Brazzein which is an inducible promoter, and tried to select a combination of a vector and a strain showing the highest expression level in these expression systems. Since the cell density differs depending on the culture time for each strain, a growth curve was drawn, and then the state of each strain progressed similarly.

The vectors pD1214-FAKs and pESC-URA used in the present invention have different promoters. Specifically, in the case of pD1214-FAKs, a constitutive promoter in which gene expression occurs in proportion to the proliferation of bacterial cells, is used, and in the case of pESC-URA, an inducible promoter in which the gene is expressed by adding an inducer, is used. Therefore, the present inventors tried to select an optimal promoter which overexpresses, secretes, and produces brazzein by culturing recombinant yeast under different conditions of the carbon source of each medium and the inducer, and comparing the strength of each promoter.

After bacteria were collected by centrifuging the cultured culture solution at 8,000 g for 30 minutes, salts were removed by performing dialysis with distilled water for 1 to 2 hours in the initial stage, and then three times each for 8 hours, and the expression levels were compared by SDS-PAGE.

Experimental Example 2. Selection of Optimal Expression Conditions for Recombinant Brazzein in Complex Medium 2-1. Confirmation of Optimal Inoculation (Seeding) Concentration Cells for inoculation into an expression medium were streaked on a YPD solid medium (10 g/L yeast extract, 20 g/L peptone, 20 g/L glucose, 20 g/L agar) from a glycerol stock of S. cerevisiae cells in which a brazzein gene was transformed using a platinum wire, and were prepared by being cultured in an incubator at 30° ° C. for 72 hours. Then, cells grown on the solid medium were inoculated into 3 mL of YPD in a test tube using a platinum wire, and then cultured in a shaking incubator under conditions of 16 to 18 hours, 30° C., and 200 rpm until $OD_{600=5}$ to 6, and the main culture was performed by inoculating the cells according to the concentration of the pre-culture solution to be inoculated.

In order to investigate the effect of the concentration of the inoculum on the expression level, the expression level was measured by varying the inoculum concentration. A complex medium YPDG (10 g/L yeast extract, 20 g/L peptone, 10 g/L glucose, and 10 g/L galactose) was used as an expression medium, 50 mL (pH 5.0) of the YPDG was put into a 250 mL Erlenmeyer flask, and culture was performed under conditions of 30° ° C. and 200 rpm for 72 hours. The inoculum was administered to the main culture solution at the concentration of 1%, 2%, 3%, 4%, 5 (v/v) % of the main culture solution such that the final $OD_{600}$ was 0.05, 0.1, 0.15, 0.2, and 0.25. Culture was performed by adding an inducer, galactose, at the lag phase. After bacteria were collected by centrifuging the sample for which culture was completed at 8,000 g for 30 minutes, the supernatant was collected. Then, the expression level of brazzein in the sample was confirmed by SDS-PAGE using 16.5% Tris-Tricine gel.

2-2. Confirmation of Optimal Initial pH of Expression Medium

Cells for inoculation into an expression medium were streaked on a YPD solid medium from a glycerol stock of S. cerevisiae cells in which a brazzein gene was transformed using a platinum wire, and were cultured in an incubator at 30° C. for 72 hours. Then, cells grown on the solid medium were inoculated into 3 mL of YPD in a test tube using a platinum wire, and then cultured in a shaking incubator under conditions of 16 to 18 hours, 30° C., and 200 rpm until $OD_{600=5}$ to 6, and the main culture was performed by inoculating the cells into an expression medium at a concentration of 2%.

YPDG was used as the expression medium, and 50 mL of the YPDG was cultured in a shaking incubator under conditions of 72 hours, 30° C., and 200 rpm using a 250 mL Erlenmeyer flask. In order to select the optimal pH, a total of five culture conditions of pH 4.5, 5.0, 5.5, 6.0 and 6.5 were established by adjusting the pH with acetic acid. Culture was performed by adding an inducer, galactose, at the lag phase. A supernatant containing brazzein produced from transformed bacterial cells was collected by centrifuging the sample for which culture was completed at 8,000 g for 30 minutes. Then, a condition under which brazzein was maximally expressed was confirmed by subjecting the supernatant containing brazzein to electrophoresis by SDS-PAGE using 16.5% Tris-Tricine gel to confirm the expression level of brazzein.

2-3. Confirmation of Optimal Culture Temperature and Culture Time

YPDG was used as the expression medium, and 50 mL of the YPDG was cultured in a shaking incubator under conditions of pH 5.0 and 200 rpm using a 250 mL Erlenmeyer flask. Three temperature conditions of 23° C., 27° C., and 30° C. were investigated to select the optimal culture temperature, and a supernatant containing brazzein produced from transformed bacterial cells was collected by taking samples every 6, 12, 24, 48, 72, 96, and 120 hours from the start time of the culture and centrifuging the sample at 8,000 g for 30 minutes. Then, the time when brazzein was maximally expressed was confirmed by subjecting the supernatant containing brazzein to electrophoresis by SDS-PAGE using 16.5% Tris-Tricine gel to confirm the expression level of brazzein. Culture was performed by adding an inducer, galactose, at the lag phase.

2-4. Confirmation of Optimal Concentration and Addition Timing of Inducer

YPDG was used as the expression medium, and 50 mL of the YPDG was cultured in a shaking incubator under conditions of pH 5.0, 72 hours, 30° C., and 200 rpm using a 250 mL Erlenmeyer flask.

Specifically, the optimum concentration of the inducer was confirmed in the process of selecting the expression system. The expression level of brazzein was confirmed according to the concentration of the inducer by adding glucose and galactose to the basal YPDG medium at a concentration of 1 to 2 (w/w) % of the total medium. Particularly in the case of the TEF promoter, expression levels were compared after addition such that glucose (%): galactose (%)=1:0, 1:1, 1:2, 2:0, 2:1, and 2:2. In addition, in order to confirm the optimal addition timing of the inducer, culturing was performed by adding the inducer at the lag phase, log phase, or stationary phase. A supernatant containing brazzein produced from transformed bacterial cells was collected by centrifuging the sample for which culture was completed at 8,000 g for 30 minutes. Then, conditions under which brazzein was maximally expressed were confirmed from the supernatant containing brazzein by SDS-PAGE using 16.5% Tris-Tricine gel.

Experimental Example 3. Selection of Optimal Expression Conditions for Recombinant Brazzein in Defined Medium 3-1. Confirmation of Optimal Carbon Source (C)/Nitrogen Source (N) Molar Ratio of Expression Medium The composition of a defined medium was basically determined based on the cellular components. With reference to the results of a study on producing a recombinant protein by culturing a yeast strain in a defined medium, the medium concentration was determined.

Specifically, 20 g/L glucose, 1 g/L magnesium sulfate, 0.1 g/L sodium chloride, 0.2 g/L EDTA, 2.54 mg/L manganese chloride, 0.088 mg/L sodium molybdate, 1 mg/L zinc chloride, 129.4 mg/L calcium chloride, 222 mg/L iron(III) chloride, 2.84 mg/L copper(II) chloride, 0.6 mg/L calcium pantothenate, 0.6 mg/L thiamine, 0.6 mg/L inositol, 0.6 mg/L pyridoxine, 0.6 mg/L nicotinic acid, and 0.02 mg/L biotin were basically used as the composition of an expression medium using a defined medium, and the nitrogen source was ammonium sulfate, and was added by calculation according to the molar concentration ratio with the carbon source. Glucose and galactose were considered as materials calculated as carbon sources. 50 mL of the expression medium was cultured in a shaking incubator under conditions of pH 5.0, 72 hours, 30° ° C., and 200 rpm using a 250 mL Erlenmeyer flask.

In order to confirm the optimal C/N molar ratio in the expression medium, culture was performed according to the C/N molar ratio of 0.1, 0.3, 0.5, 0.75, 1, 2, 4, 6, 8 and 10. Culture was performed by adding an inducer, galactose, at the lag phase at a concentration of 2 g/L. A supernatant containing brazzein produced from transformed bacterial cells was collected by centrifuging the sample for which culture was completed at 8,000 g for 30 minutes. Then, the maximal expression level of brazzein was confirmed from the supernatant containing brazzein by SDS-PAGE using 16.5% Tris-Tricine gel.

Cells for inoculation into an expression medium were streaked on a YPD solid medium from a glycerol stock of *S. cerevisiae* cells in which a brazzein gene was transformed using a platinum wire, and were cultured in an incubator at 30° C. for 72 hours. Then, cells grown on the solid medium were inoculated into 3 mL of YPD in a test tube using a platinum wire, and then cultured in a shaking incubator under conditions of 18 hours, 30° C., and 200 rpm until $OD_{600=5\sim6}$, and after a pre-culture solution was inoculated such that the final $OD_{600}$ of a main culture solution became 0.1, the cells were centrifuged under conditions of 5,000 g, 10 minutes and 20° C. to remove complex medium components, and then inoculated by being resuspended in the expression medium.

3-2. Confirmation of Optimal pH of Expression Medium

The expression medium was prepared by adding 20 g/L glucose, 12.1 g/L ammonium sulfate, 1 g/L magnesium sulfate, 0.1 g/L sodium chloride, 0.2 g/L EDTA, 2.54 mg/L manganese chloride, 0.088 mg/L sodium molybdate, 1 mg/L zinc chloride, 129.4 mg/L calcium chloride, 222 mg/L iron(III) chloride, 2.84 mg/L copper(II) chloride, 0.6 mg/L calcium pantothenate, 0.6 mg/L thiamine, 0.6 mg/L inositol, 0.6 mg/L pyridoxine, 0.6 mg/L nicotinic acid, and 0.02 mg/L biotin. 50 mL of the expression medium was put into a 250 mL Erlenmeyer flask and culture was performed in a shaking incubator under conditions of 72 hours, 30° C., and 200 rpm.

In order to confirm the optimal pH of the expression medium, the pH conditions were largely divided into two methods: One method is performed by adjusting only the initial pH with acetic acid, and the other method is performed by minimizing the change in pH of the medium throughout the entire process using a potassium phosphate buffer solution.

The initial pH was adjusted to a total of five pH values from pH 4.5 to pH 6.5 using acetic acid for comparison, and the other method was performed after dividing into a total of 6 pH values from pH 5.0 to pH 8.0 using a potassium phosphate buffer solution. Culture was performed by adding an inducer, galactose, at the lag phase at a concentration of 2 g/L. A supernatant containing brazzein produced from transformed bacterial cells was collected by centrifuging the sample for which culture was completed at 8,000 g for 30 minutes. Then, the expression level of brazzein was confirmed from the supernatant containing brazzein by SDS-PAGE using 16.5% Tris-Tricine gel.

Cells for inoculation into an expression medium were streaked on a YPD solid medium from a glycerol stock of *S. cerevisiae* cells in which a brazzein gene was transformed using a platinum wire, and were cultured in an incubator at 30° C. for 72 hours. Then, cells grown on the solid medium were inoculated into 3 mL of YPD in a test tube using a platinum wire, and then cultured in a shaking incubator under conditions of 18 hours, 30° C., and 200 rpm until $OD_{600}$=5~6, and after a pre-culture solution was inoculated such that the final $OD_{600}$ of a main culture solution became 0.1, the cells were centrifuged under conditions of 5,000 g, 10 minutes and 20° C. to remove complex medium components, and then inoculated by being resuspended in the expression medium.

3-3. Confirmation of Optimal Trace Metal Concentration and Optimal Vitamin Concentration Optimal conditions associated with defined media, such as trace metals and vitamins were performed with reference to the results of prior studies. In the present study, experiments were performed by adding a trace metal and a vitamin at a concentration of 1%, 2%, or 4%, respectively, in order to determine an effect of the trace metal and the vitamin on the expression level of brazzein in the defined medium. A supernatant containing brazzein produced from transformed bacterial cells was collected by centrifuging the sample for which culture was completed at 8,000 g for 30 minutes. Then, conditions under which brazzein was maximally expressed were confirmed from the supernatant containing brazzein by SDS-PAGE using 16.5% Tris-Tricine gel. As a result, it was confirmed that the optimal concentration of the trace metal for expressing brazzein was 20 mg/L 100×trace metal, and the optimal concentration of the vitamin was 30 mg/mL 100×vitamin.

In the above study, cells for inoculation into an expression medium were streaked on a YPD solid medium from a glycerol stock of *S. cerevisiae* cells in which a brazzein gene was transformed using a platinum wire, and were cultured in an incubator at 30° ° C. for 72 hours. Then, cells grown on the solid medium were inoculated into 3 mL of YPD in a test tube using a platinum wire, and then cultured in a shaking incubator under conditions of 18 hours, 30° C., and 200 rpm until $OD_{600}$=5~6, and after a pre-culture solution was inoculated such that the final $OD_{600}$ of a main culture solution became 0.1, the cells were centrifuged under conditions of 5,000 g, 10 minutes and 20° C. to remove complex medium components, and then inoculated by being resuspended in the expression medium.

Experimental Example 4. Purification of Expressed Recombinant Brazzein 4-1. Confirmation of Amount of Brazzein that is not Secreted and Expressed in Bacterial Cells Since the brazzein expression vector according to the present invention contains an α-mating factor signal sequence in the gene sequence, the brazzein protein produced is secreted and expressed extracellularly. Nevertheless, the brazzein protein was extracted from the yeast cells to confirm whether there was any brazzein remaining in the cells without being secreted and expressed.

A method of pulverizing yeast cells using 200 mM NaOH (Kushnirov, 2000) and a method of pulverizing yeast cells using a sonicator were used as a method of pulverizing yeast cells, and after a protein in the cells was extracted, and then centrifuged at 8,000 g for 3 minutes using a centrifuge, the protein was 4-fold diluted, and then the amount of brazzein remaining in the cells was analyzed by performing SDS-PAGE.

As a result, it was confirmed that about 92% or more of brazzein was secreted and expressed in both the complex medium and the defined medium. That is, since most of the brazzein expressed by the strain was secreted into a culture solution, the purification of brazzein was carried out for the brazzein present in the culture solution in the following experimental process.

4-2. Purification of Brazzein Expressed in Complex Medium

After the culturing of the transformed strain was completed, the cells (pellet) were removed, and the remainder was centrifuged at 8,000 g and 4° C. for 30 minutes, and then purified with a cation exchange resin in order to obtain a supernatant. In this case, since the pI value of brazzein is 5.4, acetic acid was used in order to adjust the pH to 4, which is lower than the value. A column was filled with CM sepharose fast flow beads, and a brazzein culture solution was loaded onto the column equilibrated by flowing a buffer solution (50 mm NaOAc, pH 4) having a volume about 20-fold larger than the bead volume at a flow rate of 1 ml/min. After loading, washing was performed by flowing a washing buffer solution (0.05 M NaOAc, 50 mM NaCl, pH 4) until $OD_{280}$ was not changed, 5 ml of a fractionated elution was each obtained by exchanging the washing buffer solution with an elution buffer solution (50 mM NaOAc, 400 mM NaCl, pH 4). Then, for fractionation, salts included in the buffer solution were removed by dialyzing a brazzein elution section predicted by measuring $OD_{280}$ with secondary distilled water, and then the remainder was lyophilized.

4-3. Purification of Brazzein Expressed in Defined Medium

After the culturing of the transformed strain was completed, the culture medium was centrifuged at 8,000 g and 4° C. for 30 minutes, and then the cells (pellet) and the supernatant were separated. Subsequently, low molecular weight materials and salts in the medium components were removed by dialyzing the supernatant with distilled water using a 3.5 kDa dialysis membrane. Dialysis was performed by changing the initial dialysate within 1 hour and then changing the dialysate 3 times for 8 hours each. A protein other than brazzein remaining in the supernatant was isolated from the dialyzed sample using Amicon® Ultra-15 10k (Merck Millipore co., Ltd, Billerica, Mass., USA), and Amicon® Ultra-15 3k was again used to obtain purified and concentrated brazzein remaining in the supernatant portion.

Experimental Example 5. Protein Electrophoresis

The purity of brazzein was confirmed by the method of Schagger and von Jagow (1987). Since brazzein is a small protein with a size of 6.5 kDa, SDS-PAGE was performed by preparing a 16.5% gel in order to confirm the purity of brazzein by electrophoresis. The gel was prepared using a separating gel (2.18 ml of 40% acrylamide, 2.165 ml of 3 M Tris-HCl/SDS, 0.6 ml of D.W., 85 µl of 10% APS, and 4 µl of TEMED) and a stacking gel (0.335 ml of 30% acrylamide, 0.625 ml of 3 M Tris-HCl/SDS, 1.5 ml of D.W., 30 µl of 10%, and 2 µl of TEMED). 20 µl of the sample was injected per well, and subjected to a denaturation process by applying heat in a heat block at 95° C. for 3 minutes using a 5° Tricine loading buffer, and then the rest of the process was performed.

A Dokdo-Mark™ broad-range protein marker (EBM-1032, ELPIS, Daejeon, Korea), a triple color protein marker from Bio-FACT and a BLUelf pre-stained protein ladder (Gene DireX, Taiwan) were used as protein markers. Electrophoresis was performed at 50 V, and after electrophoresis, the gel was stained with Coomassie brilliant blue R-250, and the stained gel was decolorized using a destaining agent supplemented with 10% methanol and 10% acetic acid.

Experimental Example 6. Purification Table for Recombinant Brazzein 6-1 UV Quantification Since most proteins have an intrinsic extinction coefficient at 205 nm, purified brazzein was quantified by measuring the absorbance at 205 nm (Scopes, 1974).

The reference absorbance of the UV/Vis absorptiometer was measured and fixed in a solvent in which a brazzein sample was dissolved. The absorbance was measured by gradually diluting each protein sample until the absorbance value at 205 nm approached a range of 0.3 to 0.4 in order to minimize the stray effect. The average value was calculated by measuring the absorbance of the diluted protein solution at 205 nm and 280 nm three times. Then, the intrinsic molar extinction coefficient of each protein sample was determined using the equation: $\varepsilon_{205}^{1.0\ mg/ml}=27.0+120\ (A_{280}/A_{205})$ (Ide, Masuda, & Kitabatake, 2007).

The concentration of this protein was calculated by multiplying a value obtained using the equation of concentration (mg/mL)=$A205/\varepsilon205^{1\ mg/mL}$ by the dilution factor.

6-2 BCA Quantification

BCA quantification is one of the colorimetric assays that confirm the presence of proteins or peptides. When a compound having two peptide bonds is treated with a dilute copper sulfate solution in an alkaline solution, a copper ion reduction reaction ($Cu^{2+} \rightarrow Cu^{1+}$) occurs, thereby producing a violet or purple complex compound. In this case, since the amount of complex compound formed varies depending on the concentration of the protein, standard protein solutions having different concentrations are reacted with alkaline copper sulfate, and then a standard curve is drawn by measuring absorbance.

The absorbance was measured using a BCA protein assay kit (Pierce Chemical Co., Rockford, IL, USA), and bovine serum albumin (BSA) was used as a standard material. To measure BCA, a working reagent (WR) was prepared by mixing Reagent A and Reagent B at a ratio of 50:1. After 25 μl of the sample was put into a microplate well and 200 μl of the working reagent (WR) was mixed, the plate was wrapped with foil to block light and incubated at 37° C. for 30 minutes in a shaking incubator, and the plate was cooled at room temperature. Then, $OD_{562}$ was measured and quantified by substituting the value into the standard curve.

Experimental Example 7. Measurement of Brazzein Sweetness Activity by Ascending Test Method Since brazzein is a protein rather than a sugar, it is not possible to measure sweetness using a saccharimeter. Therefore, the activity was measured using a taste test that measures the activity of brazzein by allowing humans to directly taste brazzein.

First, brazzein was dissolved in distilled water such that the final concentration was 1.0 mg/mL, samples were prepared by varying the test concentration so as to be 30 to 0.05 ng/ml, a threshold value for feeling the sweetness for the first time was obtained by tasting the sweetness of the solution, and was shown as a relative activity with respect to wild-type brazzein. The specific activity measurement method was performed as follows.

A panel of a total of 20 males and 10 females trained in the sweetness test was configured. Prior to the activity measurement, the subjects were informed of the test date and time in advance to sample the taste in their best conditions, and were prohibited from drinking alcohol on the day before the test and eating food, smoking, and the like immediately before the test. The subjects trained in advance rinsed their mouths with prepared secondary distilled water and obtained the concentration at which the sweetness was first felt while sampling the taste of 500 μl of each sample according to the concentration of each type in the order of low concentration to high concentration. The subjects were allowed to rinse their mouths with secondary distilled water for 10 seconds before testing each sample. The resulting data was obtained by discarding suspicious values through the Q test, minimizing the standard deviation, and averaging. The evaluation table for measuring the sweetness activity of recombinant brazzein is shown in FIG. 3.

As a result of the sweetness test, it could be seen that the sweetness activity of the *S. cerevisiae* wild-type brazzein was about 2,260 (+5.9%)-fold higher than the same mass of sucrose, which is almost similar to the sweetness activity [2,309 (+6.8%)-fold] of the *K. lactis* wild-type brazzein.

EXAMPLES

Example 1. Selection of Expression Strain and Vector

In order to create an optimal expression system for the sweet protein brazzein, six types of expression systems were prepared by preparing two types of expression vectors according to Experimental Examples 1-1 to 1-3, and then transforming three types of *S. cerevisiae* strains. In order to reduce the influence of the cell density and phase of the strains on the expression of brazzein, a cell growth curve of each strain was drawn (FIG. 4). When all the INVSc1, Y2805, and BY4741 strains were cultured for 16 to 18 hours, the log phase was reached, $OD_{600}$ was measured by UV, and the main culture was performed by measuring $OD_{600}$ by UV to adjust the cell concentration to $OD_{600}=0.2$.

Figure 6:
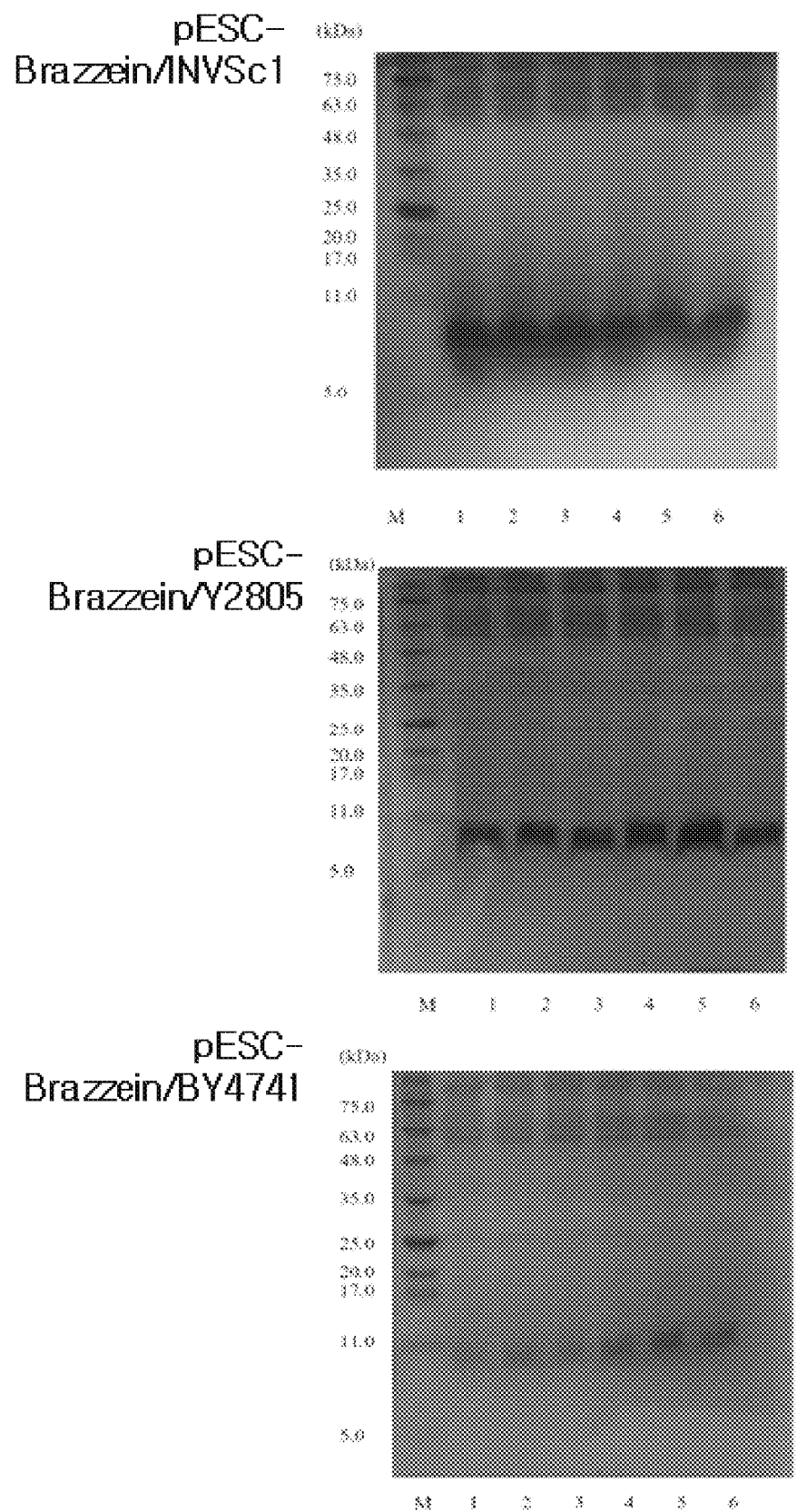
FIG. 6 is a result of comparing the expression levels of brazzein according to glucose concentration (w/w) %: galactose concentration (w/w) % relative to the total medium when INVSc1, Y2805, or BY4741 strain is transformed with a pESC-Brazzein vector, and then cultured by adding inducers (glucose and galactose) thereto. Column M, BlUelf prestained protein ladder; Column 1, 0:1; Column 2, 1:1; Column 3, 2:1; Column 4, 0:2; Column 5, 1:2; Column 6, 2:2.
Figure 7:
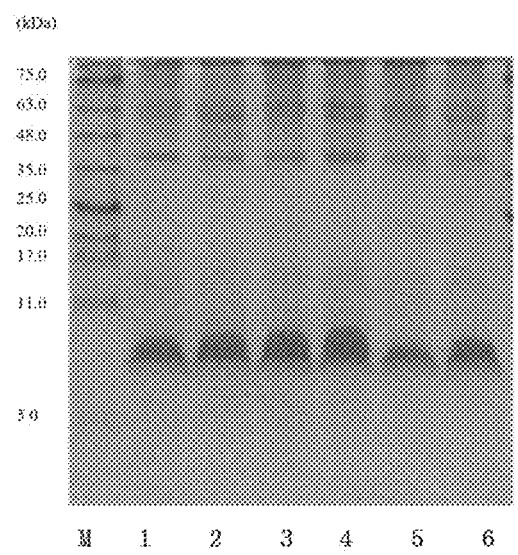
FIG. 7 is a result of comparing the expression levels of brazzein for each expression system: Column M, BlUelf prestained protein ladder; Column 1, pD1214-Brazzein/ INVSc1; Column 2, pESC-Brazzein/INVSc1; Column 3, pD1214-Brazzein/Y2805; Column 4, pESC-Brazzein/ Y2805; Column 5, pD1214-Brazzein/BY4741; Column 6, pESC-Brazzein/BY4741.
Figure 8:
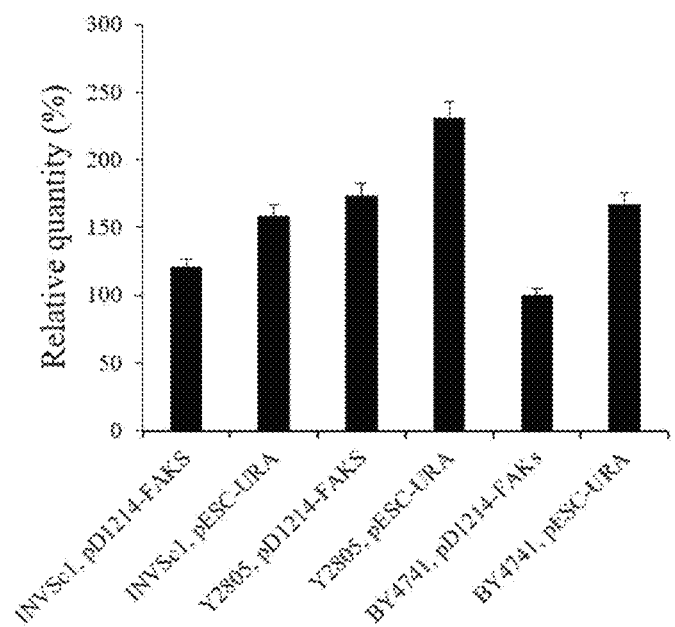
FIG. 8 illustrates a result of quantifying and comparing the expression levels of brazzein for each expression system.

Subsequently, the expression level of brazzein was compared according to Experimental Examples 1 to 7 in order to select an optimal expression system for expressing brazzein. In addition, the concentration of an inducer was changed in order to investigate the maximum expression level of brazzein, which is the target protein according to the expression vector. A strain transformed with a pD1214-FAKS vector was expressed by adding glucose (w/w) %:galactose (w/w) % at 1:0, 1:1, 1:2, 2:0, 2:1, or 2:2 (FIG. 5), and a strain transformed with a pESC-URA vector was expressed by adding glucose (w/w) %:galactose (w/w) % at 0:1, 1:1, 2:1, 0:2, 1:2, or 2:2, and then the amounts of brazzein produced were compared (FIG. 6). From the results, the concentration of an optimal inducer was set by confirming the concentration of an inducer in which brazzein was most expressed in each strain and vector, and subsequently, the expression levels of brazzein by each expression system when treated with the inducer at the optimal concentration were compared by SDS-PAGE. As a result, it could be seen that the brazzein expression level was the highest when glucose (w/w) %:galactose (w/w) %=1:2, and the expression level of recombinant brazzein was the highest in the pESC-Brazzein/Y2805 expression system (FIGS. 7 and 8). In contrast, it could also be seen that the expression system with the lowest expression level was pD1214-Brazzein/BY4741, and the expression level was the lowest, particularly, when glucose (w/w) %:galactose (w/w) %=1:0.

In general, a high copy number plasmid induces high expression (gene dosage effect), but when the copy number is very high or overexpression occurs, a metabolic imbalance in the host cell is caused to reduce the proliferation rate or growth rate of cells and cause plasmid instability to cause a reduction in the overall productivity of the recombinant protein. To solve these problems, the proliferation of cells and the expression of the gene are separately regulated by introducing an inducible promoter (Lim, Chung, Nam, & Chang, 1996). The GAL promoter, which is an inducible promoter used in the yeast S. cerevisiae, is transcriptionally suppressed in the presence of glucose, and is subjected to catabolite repression regulation by galactose after glucose depletion. Therefore, it is determined that the brazzein expression level is higher in the pESC-URA vector having the GAL promoter than in the pD1214-FAKS having the TEF Promoter.

Therefore, the pESC-Brazzein/Y2805 expression system was selected as an expression system optimized for expressing brazzein, and the optimal conditions and purification conditions for expressing brazzein by the pESC-Brazzein/Y2805 expression system were confirmed below.

Example 2. Optimal Conditions for Expressing Brazzein by pESC-Brazzein/Y2805 Expression System in Complex Medium In order to confirm the conditions optimized for expressing brazzein when the pESC-Brazzein/Y2805 expression system was cultured in a complex medium, the brazzein expression levels according to various conditions were compared according to Experimental Example 2.

2-1. Optimal Copy Number for Expressing Brazzein in Complex Medium

Figure 9:
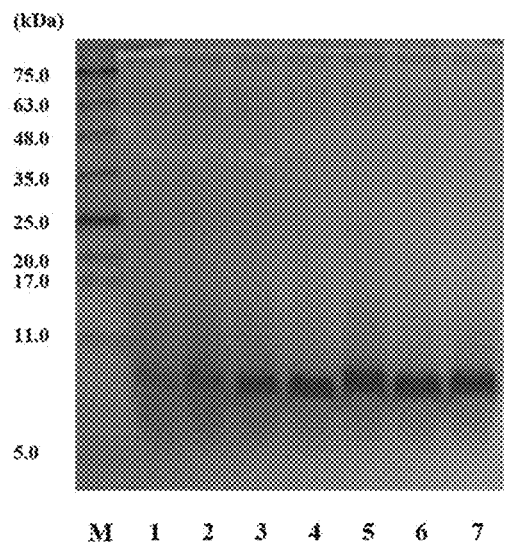
FIG. 9 is a result of comparing the expression levels of brazzein according to the copy number of a recombinant vector of a pESC-Brazzein/Y2805 expression system: Column M, BlUelf prestained protein ladder; Column 1, copy number=5; Column 2, copy number=10; Column 3, copy number=20; Column 4, copy number=30; Column 5, copy number=40; Column 6, copy number=50; Column 7, copy number=60.
Figure 10:
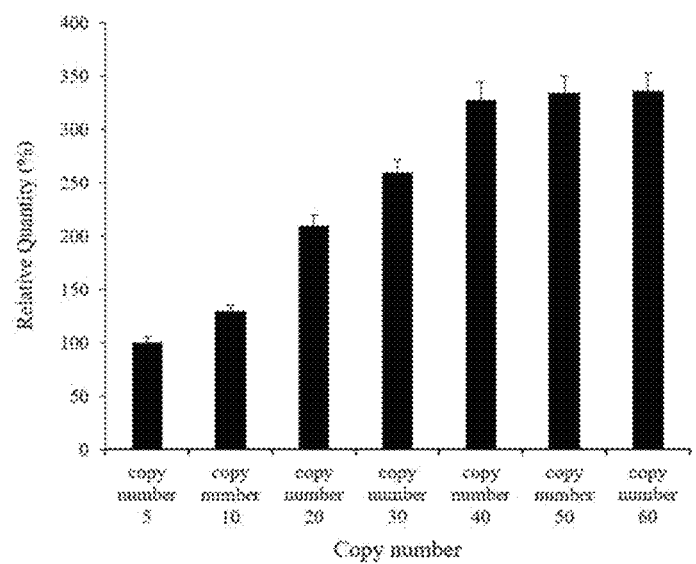
FIG. 10 illustrates a result of quantifying and comparing the expression levels of brazzein according to the copy number of a recombinant vector of a pESC-Brazzein/Y2805 expression system.

In order to understand the copy number in the strain of the transformed plasmid that allows brazzein to be expressed most appropriately, brazzein expression levels by copy number were compared. The copy number of the plasmid was measured by qRT-PCR according to Example 1-5, and the copy number was 5, 20, 30, 40, 50, or 60. As a result, as illustrated in FIG. 9, it was found that the expression level of brazzein differs according to the copy number of the expression vector inserted into the yeast S. cerevisiae. It was found that the expression level of brazzein was the highest when the copy number was 40 to 60, and the expression level was not significantly changed, particularly, from the copy number of 40 or more (FIG. 10).

2-2. Optimal Concentration of Pre-Culture Solution for Expressing Brazzein in Complex Medium Next, the optimal concentration of a pre-culture solution was confirmed by comparing the brazzein expression levels according to the concentration of the pre-culture to be inoculated according to Experimental Example 2-1. After colonies grown in a solid medium were collected, inoculated into a liquid medium, and pre-cultured for 16 to 18 hours, the pre-culture solution was inoculated into a mass-production expression medium prepared in advance, and cultured. In this case, the concentration of the pre-culture solution to be inoculated was adjusted to 1%, 2%, 3%, 4%, or 5% of the main culture solution, and the $OD_{600}$ of the main culture solution after inoculation was each 0.05, 0.1, 0.15, 0.2, or 0.25.

Figure 11:
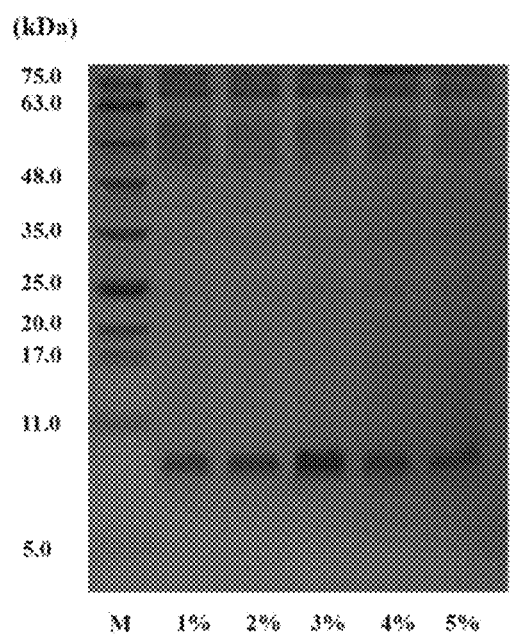
FIG. 11 is a result of comparing the expression levels of brazzein according to the inoculation concentration of a pre-culture solution in a pESC-Brazzein/Y2805 expression system.
Figure 12:
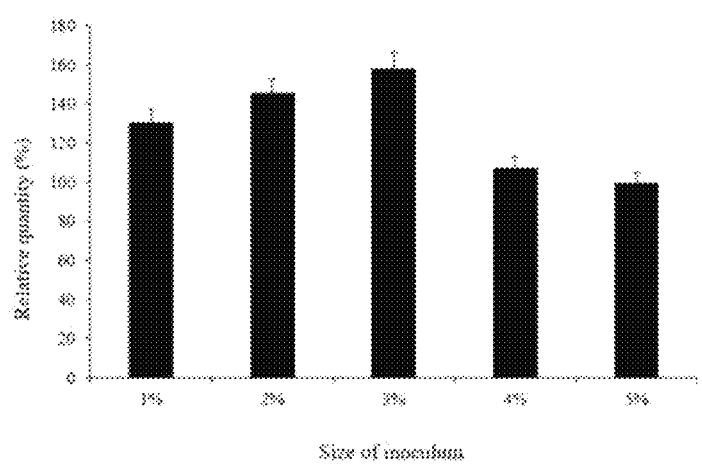
FIG. 12 is a result of quantifying and comparing the expression levels of brazzein according to the inoculation concentration of a pre-culture solution in a pESC-Brazzein/ Y2805 expression system.

As a result of comparing the brazzein expression pattern on Tris-Tricine gel by SDS-PAGE after culturing, the expression level of brazzein was the highest when the concentration of the pre-culture solution was 3% and the $OD_{600}$ of the main culture was 0.15, and was 158% higher than the expression level at the pre-culture solution concentration of 5% (FIGS. 11 and 12). When the $OD_{600}$ is 0.05 or 0.1, it seems that the number of cells capable of expressing brazzein is less than when the $OD_{600}$ is 0.15, and thus brazzein expression is low, and when the $OD_{600}$ is 0.2 or 0.25, it is thought that protein expression is low due to oxidative stress, and other problems with cell growth as the amount of cells increases, and it seems that an appropriate amount of cell density is required.

Therefore, it was confirmed that the optimal concentration of the pre-culture solution for inoculation was when the $OD_{600}$ was 0.15.

2-3. Optimal Initial pH for Expressing Brazzein in Complex Medium

Next, an optimal initial pH was selected by comparing the expression levels of brazzein according to the initial pH of the expression medium according to Experimental Example 2-2. The initial pH was adjusted to pH 4.5, 5.5, 6.0, or 6.5 for comparison.

Figure 13:
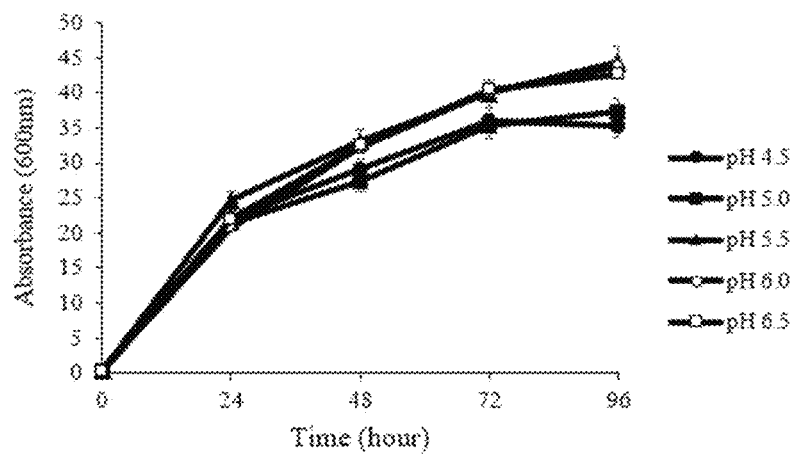
FIG. 13 illustrates a growth curve of a *Saccharomyces cerevisiae* strain according to the pH of a medium.
Figure 14:
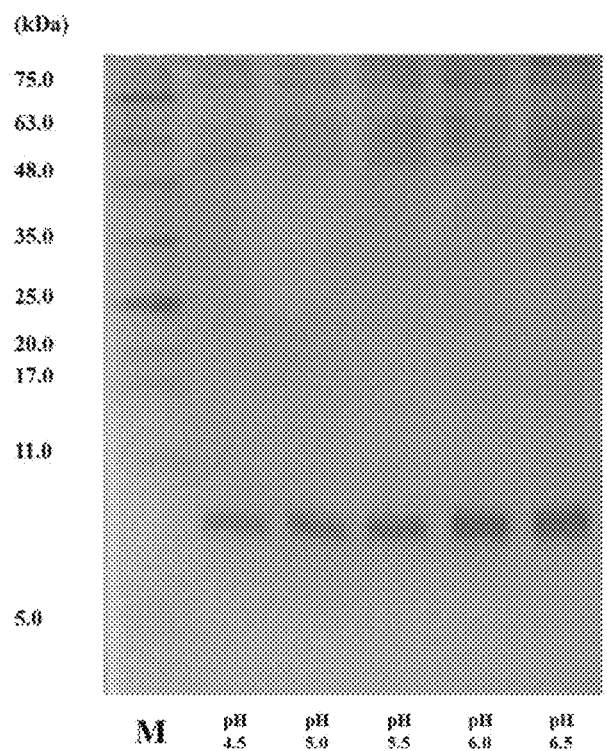
FIG. 14 is a result of comparing the expression levels of brazzein according to the pH of a medium in a pESC-Brazzein/Y2805 expression system.

As a result, it could be confirmed that there was no significant difference in the number of cells even when the pH of the expression medium was changed (FIG. 13), but there is a difference in the expression level of brazzein according to the initial pH when the expression levels of brazzein in the medium after culturing was completed were compared by SDS-PAGE (FIG. 14). Specifically, it could be confirmed that the expression level of brazzein was the highest when the initial pH was pH 6.0, and was about 180% higher than the expression level of brazzein when the initial pH was 4.5. Therefore, the optimal initial pH for expressing brazzein in the complex medium was selected to be pH 6.0.

2-4. Optimal Culture Temperature and Culture Time for Expressing Brazzein in Complex Medium Since intracellular energy metabolism, oxidative stress, protein folding, amino acid metabolism, RNA and ribosome biosynthesis, and the like are affected by the culture temperature of cells, optimal temperature conditions needed to be established such that the transformed cells according to the present invention could appropriately express recombinant brazzein. Therefore, the optimal culture temperature and time were confirmed by comparing the expression levels of brazzein according to the culture temperature and time according to Experimental Example 2-3. For the culture temperature, three temperature conditions of 23° C., 27° C., and 30° C. were compared, and the culture time was divided into 6, 12, 24, 48, 72, 96, and 120 hours for comparison.

Figure 15:
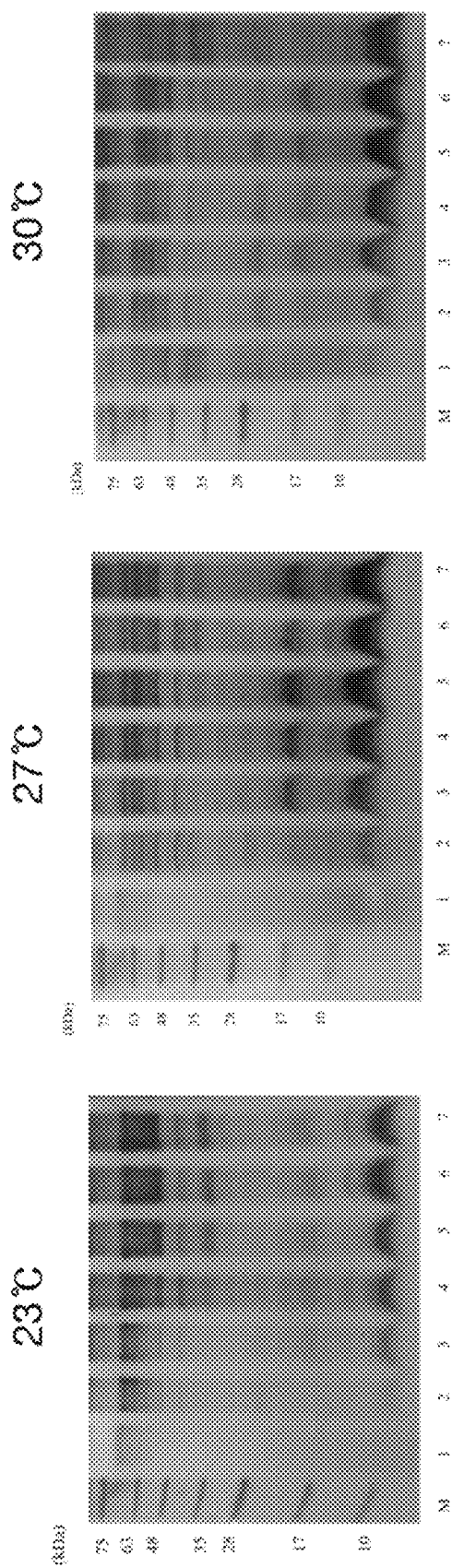
FIG. 15 is a result of comparing the expression levels of brazzein according to culture temperature and culture time in a pESC-Brazzein/Y2805 expression system. Column M, Triple color protein marker; Column 1, cultured for 6 hours; Column 2, cultured for 12 hours; Column 3, cultured for 24 hours; Column 4, cultured for 48 hours; Column 5, cultured for 72 hours; Column 6, cultured for 96 hours; Column 7, cultured for 120 hours.
Figure 16:
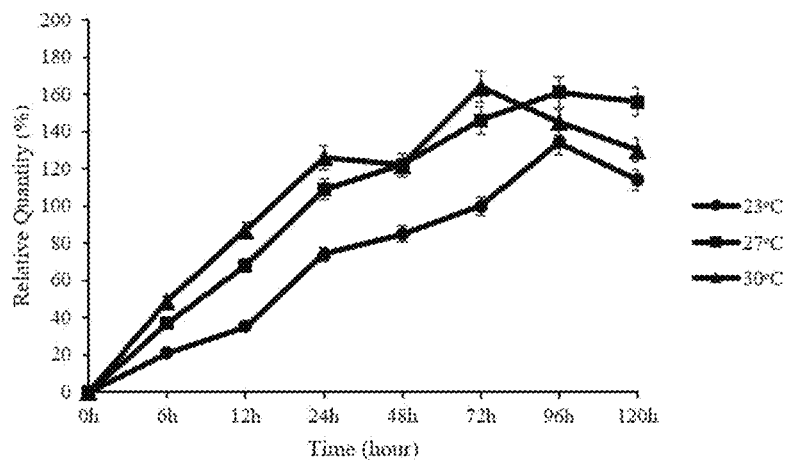
FIG. 16 is a result of comparing the relative expression levels of brazzein according to culture temperature and culture time in a pESC-Brazzein/Y2805 expression system.

As a result, the expression levels of brazzein were high during culture for 96 hours in the case of the culture temperature of 23° C. and 27° C., and the highest expression level of brazzein was exhibited during culture for 72 hours at 30° C. (FIG. 15). Collectively, the highest expression level of brazzein was exhibited during culture at a culture temperature of 30° C. for 72 hours (FIG. 16). The expression level of brazzein was not significantly changed even when the culture time exceeded 72 hours, which is presumed to be that the inducer was completely used from that time point on. Furthermore, it is considered that the culture after 72 hours may increase the expression of proteins other than brazzein, rather adversely affecting purification. Therefore, it was confirmed that the optimal culture temperature was 30° C., and the optimal culture time was 72 hours.

2-5. Optimal Inducer Concentration and Inducer Addition Timing for Expressing Brazzein in Complex Medium Finally, the optimal inducer concentration and inducer addition timing were confirmed by comparing the expression levels of brazzein according to the inducer addition timing according to Experimental Example 2-4. As described above, the optimal inducer concentration was confirmed in the process of selecting the expression system. For the concentration of glucose and galactose, the pD1214-FAKS vector was added such that glucose (w/w) %:galactose (w/w) %=1:0, 1:1, 1:2, 2:0, 2:1, or 2:2, and the pESC-URA vector was added such that glucose (w/w) %:galactose (w/w) %=0:1, 1:1, 2:1, 0:2, 1:2, or 2:2, and the expression levels of brazzein were compared by culturing strains. Further, after the inducer was added at the lag phase, log phase, or stationary phase, the expression levels of brazzein were compared.

As a result, as illustrated in FIG. 6, it was found that the expression level of the pESC-URA vector was the highest when glucose (w/w) %:galactose (w/w) % as inducers were added at 1:2. Therefore, it was confirmed that the optimal inducer concentration was glucose (w/w) %:galactose (w/w) %=1:2 in both the complex medium and the defined medium.

Figure 17:
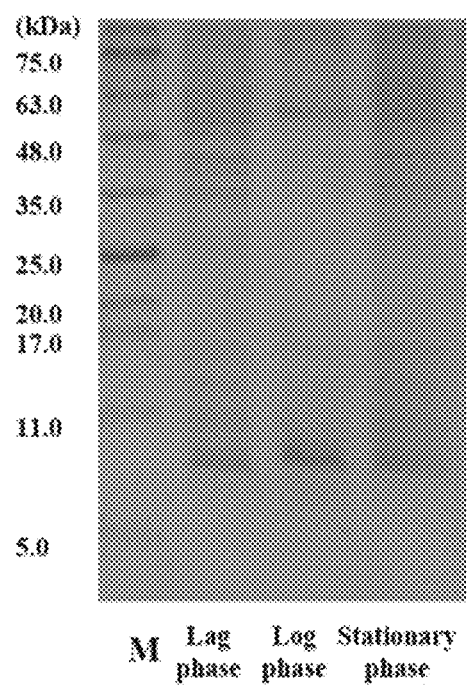
FIG. 17 is a result of comparing the expression levels of brazzein according to the time point when an inducer is added in a pESC-Brazzein/Y2805 expression system.
Figure 18:
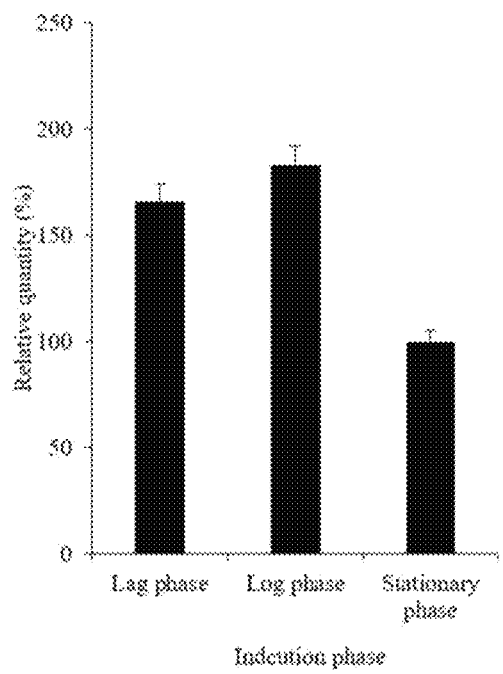
FIG. 18 is a result of comparing the relative expression levels of brazzein according to the time point when an inducer is added in a pESC-Brazzein/Y2805 expression system.

In addition, it was confirmed that brazzein was maximally expressed in the medium to which the inducer was added at the log phase (FIG. 17). Specifically, when the inducer was added at the log phase, the expression level of brazzein was about 78% higher than that when the inducer was added at the stationary phase (FIG. 18). The reason that the expression level of brazzein is higher when the inducer is added at the log phase or stationary phase than that when the inducer is added at the lag phase is thought to be because the lag phase is the time when cell growth and protein expression simultaneously occur, whereas the log phase or stationary phase is the time when the growth of cells is completed to some degree, and thus the inducer can completely be used only for protein expression.

Example 3. Optimal Conditions for Expressing Brazzein by pESC-Brazzein/Y2805 Expression System in Defined Medium In order to confirm the conditions optimized for expressing brazzein when the pESC-Brazzein/Y2805 expression system was cultured in a defined medium, the brazzein expression levels according to various conditions were compared according to Experimental Example 3. Brazzein in the defined medium was cultured under conditions of 30° C., a culture time of 72 hours, and inducer addition of glucose (w/w) %:galactose (w/w) %=1:2, which are optimal conditions confirmed in the complex medium culture, and an optimal culture composition was additionally confirmed.

3-1. Optimal C/N Molar Ratio for Expressing Brazzein in Defined Medium

Figure 19:
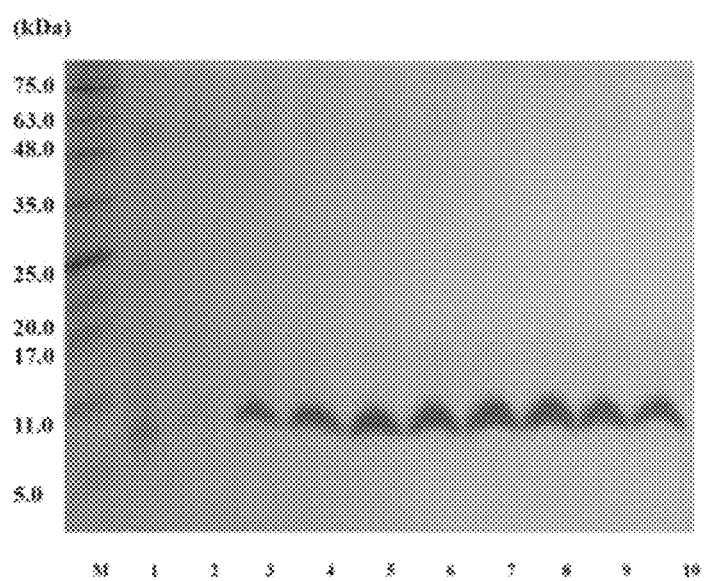
FIG. 19 is a result of comparing the expression levels of brazzein according to the C/N ratio of a defined medium when a pESC-Brazzein/Y2805 expression system is cultured in the defined medium (Columns 1 to 10, C/N molar ratio sequentially from the left=0.1, 0.3, 0.5, 0.75, 1, 2, 4, 6, 8, 10)
Figure 20:
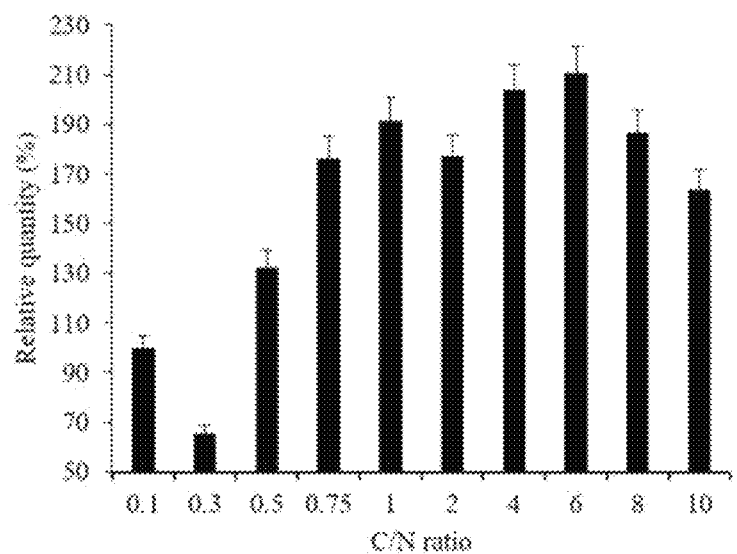
FIG. 20 is a result of comparing the relative expression levels of brazzein according to the C/N ratio of a defined medium when a pESC-Brazzein/Y2805 expression system is cultured in the defined medium.

An optimal C/N molar ratio was confirmed by comparing the expression levels of brazzein according to the molar ratio of carbon source (C)/nitrogen source (N) in the medium according to Experimental Example 3-1. Specifically, ten C/N molar ratios of 0.1, 0.3, 0.5, 0.75, 1, 2, 4, 6, 8, and 10 were compared. As a result, it could be confirmed that the expression level of brazzein was the highest when the C/N molar ratio was 6:1 (FIGS. 19 and 20).

3-2. Optimal pH for Expressing Brazzein in Defined Medium

Next, an optimal initial pH was confirmed by comparing the expression levels of brazzein according to the pH of the defined medium according to Experimental Example 3-2. Since purification in the complex medium is performed using a cation exchange resin, pH adjustment using a buffer solution is limited, but because purification in the defined medium is performed using an Amicon filter through which separation is performed according to the size of the molecule, a buffer solution can be used, and thus the pH was adjusted using an acetic acid or potassium phosphate buffer solution. Specifically, as described above, the initial pH was adjusted using acetic acid, or the pH was adjusted to be as constant as possible throughout the entire process using a potassium phosphate buffer solution.

The expression levels of brazzein were compared by establishing a total of five initial pHs of pH 4.5, 5.0, 5.5, 6.0, and 6.5 using acetic acid, and the expression levels of brazzein were compared by establishing a total six pHs of pH 5.0, 5.5, 6.0, 6.5, 7.0, and 8.0 using a potassium phosphate buffer solution.

Figure 21:
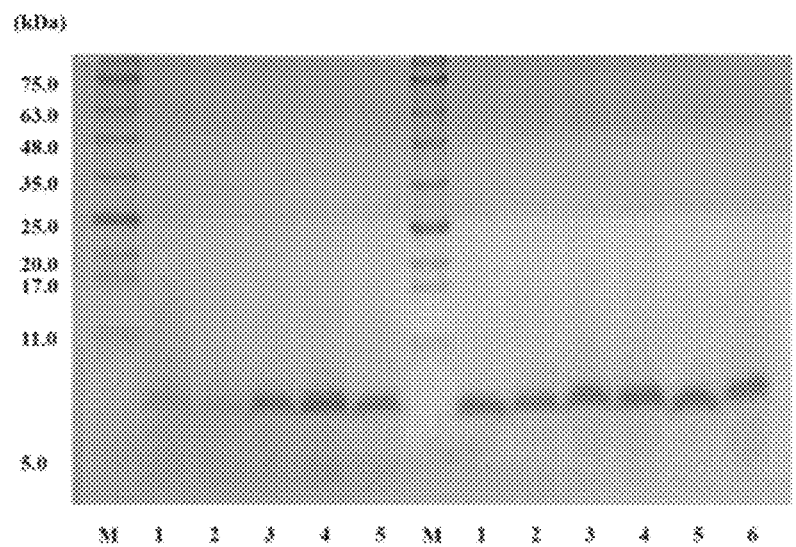
FIG. 21 is a result of comparing the expression levels of brazzein according to pH when a pESC-Brazzein/Y2805 expression system is cultured in the defined medium. Column M on the left side: BlUelf prestained protein ladder; Column 1 on the left side, pH 4.5; Column 2 on the left side, pH 5.0; Column 3 on the left side, pH 5.5; Column 4 on the left side, pH 6.0; Column 5 pH 6.5. Column M on the right side: BlUelf prestained protein ladder; Column 1 on the right side, pH 5.0; Column 2 on the right side, pH 5.5; Column 3 on the right side, pH 6.0; Column 4 on the right side, pH 6.5; Column 5 on the right side, pH 7.0; Column 6 on the right side, pH 8.0.
Figure 22:
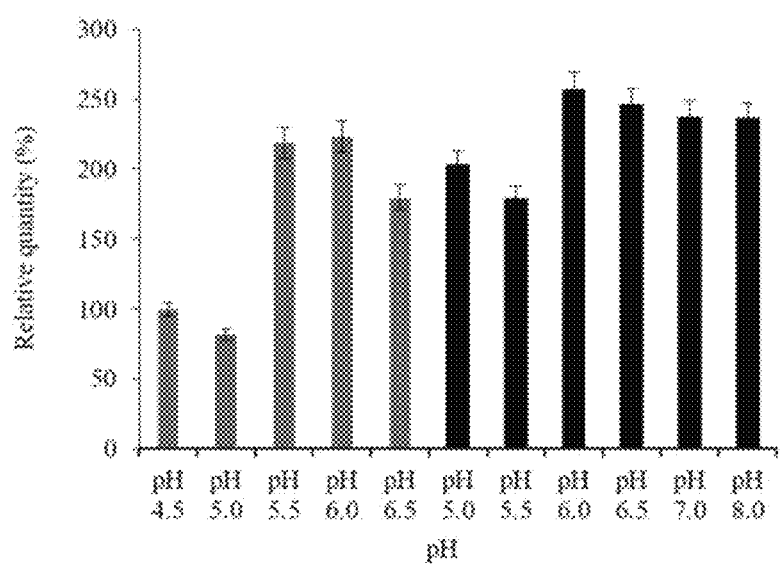
FIG. 22 is a result of comparing the relative expression levels of brazzein according to pH when a pESC-Brazzein/ Y2805 expression system is cultured in a defined medium.

As a result, in both cases of adjusting the pH using acetic acid or a potassium phosphate buffer solution, the expression level of brazzein was the highest when the pH was 6.0 (FIGS. 21 and 22). Furthermore, it could be confirmed that when the pH was maintained using a potassium phosphate buffer solution throughout the entire culture timing, the expression level of brazzein was higher as a whole than that when the pH during the initial culture was adjusted using acetic acid. Therefore, it was confirmed that it is optimal to maintain the pH at 6.0 using a potassium phosphate buffer solution in order to express brazzein in a defined medium.

3-3. Optimal Conditions for Expressing Brazzein in Defined Medium

Finally, in order to confirm optimal conditions for expressing brazzein in a defined medium, various culture conditions (C/N ratio, pH, trace metal, and vitamin) were combined, and then the expression levels of brazzein were compared. As described in Experimental Example 3-3, optimization conditions associated with defined media such as trace metals and vitamins were investigated with reference to the results of prior studies, and for expressing brazzein, the optimal trace metal concentration was 20 mg/L 100× trace metal, and the optimal vitamin concentration was 30 mg/mL 100×vitamin.

Figure 23A:
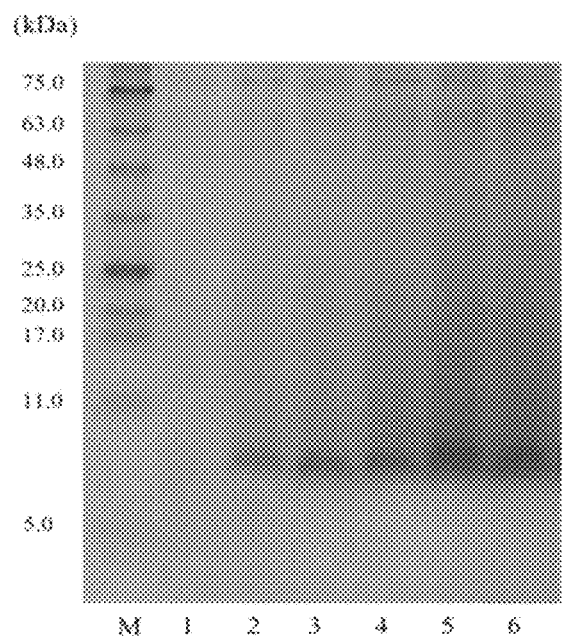
FIGS. 23A and 23B is a result of comparing the expression levels of brazzein by culturing a pESC-Brazzein/Y2805 expression system under various culture conditions. Column M: BLUelf prestained protein marker; Column 1: 0.1 C/N ratio; Column 2: optimized C/N ratio; Column 3: optimized C/N ratio+vitamin+trace metal; Column 4: optimized C/N ratio+vitamin+pH; Column 5: optimized C/N ratio+trace metal+pH; Column 6 optimized C/N ratio+vitamin+trace metal+pH.
Figure 23B:
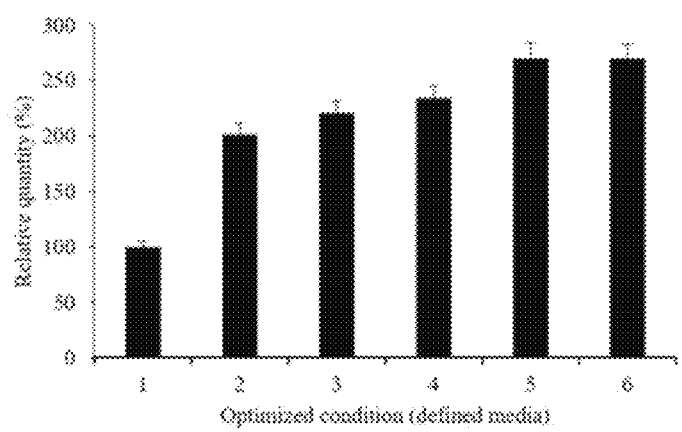

As a result, it could be confirmed that the brazzein expression level was the highest when the optimal C/N ratio (6:1) and pH (pH 6) confirmed in Examples 3-1 and 3-2 were used and the trace metal at the optimal concentration and/or the vitamin at the optimal concentration were/was added to the medium (FIGS. 23A and 23B).

Example 4. Purification Conditions for Recombinant Brazzein

After a transformed strain was cultured in a complex medium or defined medium under the optimal conditions selected in Examples 2 and 3, optimal conditions for purifying secreted and expressed brazzein was investigated according to Experimental Example 4.

4-1. Purification of Recombinant Brazzein in Complex Medium

Figure 24:
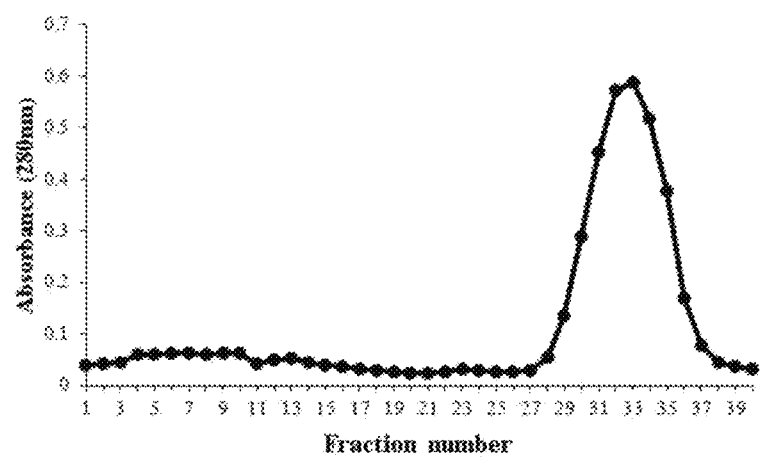
FIG. 24 illustrates elution patterns when brazzein is analyzed by CM Sepharose chromatography.
Figure 25:
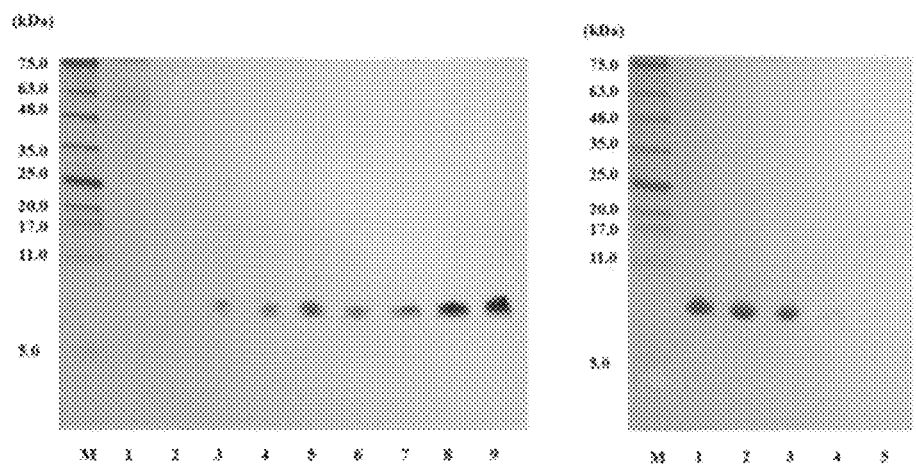
FIG. 25 illustrates a result of confirming the expression level of brazzein for each fraction after brazzein is eluted by CM Sepharose chromatography. Column M on the left side, BLUelf prestained protein marker; Column 1 on the left side. fraction 26; Column 2 on the left side, fraction 27; Column 3 on the left side, fraction 28; Column 4 on the left side, fraction 29; Column 5 on the left side, fraction 30; Column 6 on the left side, fraction 31; Column 7 on the left side, fraction 32; Column 8 on the left side, fraction 33; Column 9 on the left side, fraction 34. Column M on the right side, BLUelf prestained protein marker; Column 1 on the right side, fraction 35; Column 2 on the right side, fraction 36; Column 3 on the right side, fraction 37; Column 4 on the right side, fraction 38; Column 5 on the right side, fraction 39.

Recombinant brazzein expressed in the complex medium was purified according to Experimental Example 4-2. Specifically, secreted and expressed brazzein was purified from the medium using CM-Sepharose chromatography (cation exchange resin chromatography). Brazzein was purified from a supernatant from which bacteria had been removed by centrifuging the culture solution at 8,000 g for 30 minutes. After the pH of the supernatant was adjusted to pH 4.0 using acetic acid, a supernatant having a volume of about 6-fold the volume of CM beads was loaded. In this case, in order to reduce the loss of the expressed brazzein, that is, to increase the yield, the filtrate of the supernatant was repeatedly loaded onto the column twice. After loading, washing was performed with a washing buffer solution (50 mM NaOAc, 50 mM NaCl, pH 4) until there was no change in $OD_{280}$. That is, washing was performed using a solution having a volume of about 13-fold or more the column volume, and elution was fractionated by 1 ml using an elution buffer solution (50 mm NaOAc, 400 mm NaCl, pH 4). The $OD_{280}$ of the eluted fraction was measured, and fractions expected to have a protein were dialyzed three times with secondary distilled water and lyophilized. The purity of purified brazzein was confirmed by SDS-PAGE (FIGS. 24 and 25).

Meanwhile, as a result of performing an experiment at various concentrations in order to determine the NaCl concentration of the washing solution, the maximally pure brazzein was obtained when washed with a washing buffer solution containing 50 mM NaCl.

4-2. Purification of Recombinant Brazzein Expressed in Defined Medium

Figure 26:
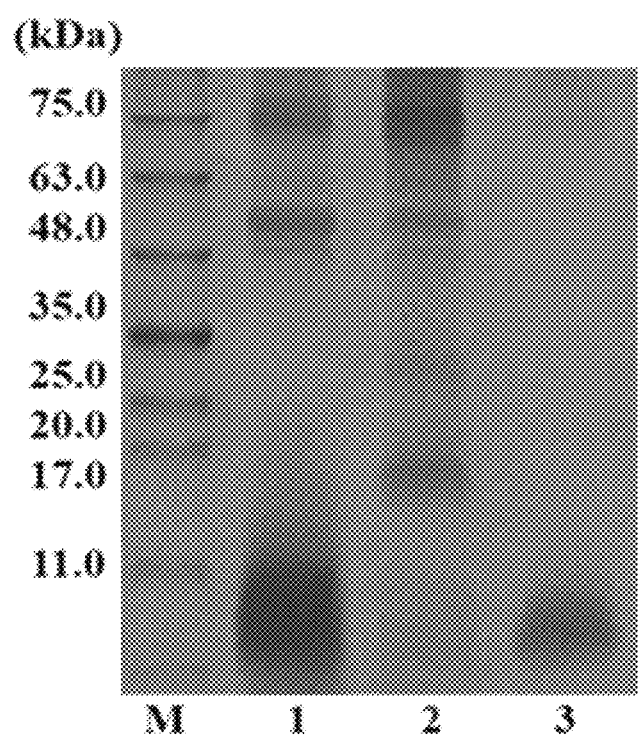
FIG. 26 illustrates a result of confirming the purity of brazzein purified after being expressed in a defined medium by SDS-PAGE.

Recombinant brazzein expressed in the defined medium was purified according to Experimental Example 4-3. Specifically, brazzein secreted and expressed in the defined medium was purified as follows. After cells and the supernatant were separated by centrifuging the medium for which culture was completed under conditions of 8,000 g, 30 minutes, and 4° C., the sample was dialyzed with distilled water using a 3.5 kDa cut off dialysis membrane. Distilled water was replaced every 8 hours for 24 hours. Brazzein was purified by centrifuging the sample for which dialysis was completed at 8,000 g for 20 minutes using Amicon® Ultra-15 10k (Merck Millipore co., Ltd, Billerica, Mass., USA). The purity of purified brazzein was confirmed by SDS-PAGE (FIG. 26).

4-3. Purification Table for Recombinant Brazzein (Confirmation of Brazzein Yield)

Finally, when the expression and purification conditions were optimized, the yield of brazzein was calculated by the BCA quantification according to Experimental Example 6 and a method of measuring absorbance at 205 nm, lyophilizing the sample, and then measuring the mass.

For the purity of recombinant brazzein produced under the optimized expression conditions, the expression level of brazzein was calculated by analyzing the density by SDS-PAGE. As a result, it could be confirmed that for the expression level of brazzein secreted and expressed in the complex medium, about 32% of the total proteins secreted and expressed corresponded to brazzein, and 290 mg of brazzein was secreted and expressed when 1 L was cultured (Table 5).

It was confirmed that about 44% of the total proteins secreted and expressed in the defined medium corresponded to brazzein, and thus about 270 mg of brazzein was secreted and expressed (Table 6), and accordingly, it could be seen that for the secreted and expressed amount, a larger amount of brazzein was expressed in the complex medium than in the defined medium.

However, it was found that the amount of proteins other than brazzein secreted and expressed in the defined medium was small, and thus, the purification yield was better during the purification process. The complex medium and the defined medium showed a purification efficiency of 36% and 43%, respectively, and 103 mg and 114 mg of pure brazzein were obtained from the complex medium and the defined medium, respectively (Tables 5 and 6). Therefore, it is determined that more purified brazzein can be obtained from the defined medium having a lower production unit price than the complex medium, and an expression system using the defined medium is an efficient production system.

TABLE 5

Purification table of brazzein secreted and expressed in complex medium analyzed by BCA quantification

| Steps | Total protein amount (mg) | Yield (%) | Brazzein purity (%) |
| --- | --- | --- | --- |
| Crude extract | 898 | 100 | 32 |
| CM-Sepharose chromatography | 103 | 36 | 100 |

(1 L of culture medium was analyzed)

TABLE 6

Purification table of brazzein secreted and expressed in complex medium analyzed by BCA quantification

| Steps | Total protein amount (mg) | Yield (%) | Brazzein purity (%) |
| --- | --- | --- | --- |
| Crude extract | 603 | 100 | 44 |
| Amicon ® ultra-15 10k crude | 114 | 43 | 100 |

(1 L of culture medium was analyzed)

The present inventors confirmed that when a brazzein expression recombinant vector for high expression of brazzein in *Saccharomyces cerevisiae* was prepared and a *S. cerevisiae* strain Y2805 was transformed with the recombinant vector, the expression level of brazzein was particularly high, thereby completing an optimal expression system for mass-producing brazzein. Further, when the brazzein expression system is cultured under the optimal culture conditions according to the present invention, the amount of brazzein produced is further increased, the purification process is simple, and costs are reduced. Therefore, it is expected that the brazzein expression system according to the present invention can be widely used for mass-producing and commercializing brazzein, which is a sweet protein.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described Examples are illustrative only in all aspects and are not restrictive.

What is claimed is:

1. A method for mass-producing brazzein, the method comprising:
   (1) transforming a *Saccharomyces cerevisiae* strain with a recombinant vector for expressing brazzein in *Saccharomyces cerevisiae*;
   (2) culturing the strain transformed in Step (1);
   (3) obtaining a culture of the transformed strain cultured in Step (2); and
   (4) purifying brazzein from the culture of Step (3),
   wherein the recombinant vector comprises a pESC-URA vector into which a brazzein encoding gene comprising the nucleotide sequence of SEQ ID NO:2; and a gene encoding an α-mating factor of *Saccharomyces cerevisiae* consisting of the amino acid sequence of SEQ ID NO:6 are inserted, and
   wherein the *Saccharomyces cerevisiae* strain is Y2805.

2. The method of claim 1, wherein the culturing in Step (2) satisfies one or more of the following conditions:
   (a) the copy number of the recombinant vector for expressing brazzein introduced into the *Saccharomyces cerevisiae* strain is 5 to 60;
   (b) the culturing is performed in a complex medium or a defined medium;
   (c) the culturing is performed at a pH of 4.5 to 6.5;
   (d) the culturing is performed at 20° C. to 35° C.; or
   (e) the culturing is performed for 6 to 120 hours.

3. The method of claim 2, wherein when the culturing in Step (2) is performed in a defined medium, the culturing in Step (2) further satisfies one or more of the following conditions:
   (a) the molar ratio (M/M) of a carbon source (C)/a nitrogen source (N) in the defined medium is 0.1 to 10;
   (b) the culturing is performed at a pH of 5 to 8, and the pH is adjusted with acetic acid or a buffer solution;
   (c) the defined medium further comprises a trace metal at a concentration of 1 to 4 (w/w) %; or
   (d) the defined medium further comprises a vitamin at a concentration of 1 to 4 (w/w) %.

4. The method of claim 1, wherein the culturing step in Step (2) comprises: culturing a transformed strain by streaking the transformed strain on a solid medium; preparing a pre-culture solution by collecting colonies formed on the solid medium and pre-culturing the colonies in a liquid medium; and culturing the resulting solution by inoculating the pre-culture solution into a main culture solution, wherein the inoculating concentration of the pre-culture solution is 1 to 5 (v/v) % of the main culture solution, wherein the $OD_{600}$ of the main culture solution into which the pre-culture solution is inoculated is 0.05 to 0.25.

5. The method of claim 1, wherein the culturing step in Step (2) comprises adding an inducer in order to induce the transformed strain to express brazzein, wherein the inducer is selected from glucose, galactose, and a combination thereof, wherein the inducer is added at a concentration of 1 to 2 (w/w) % of the total medium.

6. The method of claim 5, wherein the adding of the inducer satisfies one or more of the following conditions:
   (a) a ratio of glucose/galactose is 0.1 to 2; or
   (b) the inducer is added at a log phase or stationary phase.

7. The method of claim 1, wherein the purifying step in Step (4) is purifying brazzein by ultrafiltration.

* * * * *

SEQUENCE LISTING

<160> NUMBER OF SEQ ID NOS: 19

<210> SEQ ID NO 1
<211> LENGTH: 159

```
<212> TYPE: DNA
<213> ORGANISM: Artificial Sequence
<220> FEATURE:
<223> OTHER INFORMATION: DNA sequence of Brazzein

<400> SEQUENCE: 1
gacaagtgca agaaggtcta cgagaactac cccgtgtcca actgtcaact ggctaatcag    60
tgcaactacg attgcaagct cgacaagcac gctcgctccg gcgaatgctt ctacgatgag   120
aagcgcaacc tgcagtgcat ttgcgactac tgcgagtac                          159

<210> SEQ ID NO 2
<211> LENGTH: 159
<212> TYPE: DNA
<213> ORGANISM: Artificial Sequence
<220> FEATURE:
<223> OTHER INFORMATION: Optimized DNA sequence of Brazzein

<400> SEQUENCE: 2
gacaagtgca gaaaagtata cgagaattat ccggtgtcaa agtgtcagtt agcaaatcag    60
tgtaattatg actgcaagtt ggataaacga gcacgttccg gagactgttt ttatgacaag   120
aagaggaatt tacaatgcat atgcgactat tgtgagtat                          159

<210> SEQ ID NO 3
<211> LENGTH: 53
<212> TYPE: PRT
<213> ORGANISM: Artificial Sequence
<220> FEATURE:
<223> OTHER INFORMATION: Amino acid sequence of Brazzein

<400> SEQUENCE: 3

Asp Lys Cys Lys Lys Val Tyr Glu Asn Tyr Pro Val Ser Lys Cys Gln
 1               5                  10                  15

Leu Ala Asn Gln Cys Asn Tyr Asp Cys Lys Leu Asp Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 4
<211> LENGTH: 255
<212> TYPE: DNA
<213> ORGANISM: Artificial Sequence
<220> FEATURE:
<223> OTHER INFORMATION: DNA sequence of alpha-mating factor

<400> SEQUENCE: 4
atgaaattct ctactatatt agccgcatct actgctttaa tttccgttgt tatggctgct    60
ccagtttcta ccgaaactga catcgacgat cttccaatat cggttccaga agaagccttg   120
attggattca ttgacttaac cggggatgaa gtttccttgt tgcctgttaa taacggaacc   180
cacactggta ttctattctt aaacaccacc atcgctgaag ctgctttcgc tgacaaggat   240
gatctcgaga aaaga                                                   255

<210> SEQ ID NO 5
<211> LENGTH: 255
<212> TYPE: DNA
<213> ORGANISM: Artificial Sequence
<220> FEATURE:
<223> OTHER INFORMATION: Optimized DNA sequence of alpha-mating factor
```

```
<400> SEQUENCE: 5
atgaagttct ctactatttt ggctgcttct actgctttga tttctgttgt tatggctgct    60
ccagtttcta ctgaaactga tattgatgat ttgccaattt ctgttccaga agaagccttg   120
attggtttta ttgatttgac tggtgacgaa gtttctttgt tgccagttaa caacggtact   180
catactggta ttttgttctt gaacactact attgctgaag ctgctttcgc tgataaggat   240
gatttggaaa agaga                                                    255

<210> SEQ ID NO 6
<211> LENGTH: 85
<212> TYPE: PRT
<213> ORGANISM: Artificial Sequence
<220> FEATURE:
<223> OTHER INFORMATION: Amino acid sequence of alpha-mating factor

<400> SEQUENCE: 6

Met Lys Phe Ser Thr Ile Leu Ala Ala Ser Thr Ala Leu Ile Ser Val
1               5                   10                  15

Val Met Ala Ala Pro Val Ser Thr Glu Thr Asp Ile Asp Asp Leu Pro
                20                  25                  30

Ile Ser Val Pro Glu Glu Ala Leu Ile Gly Phe Ile Asp Leu Thr Gly
            35                  40                  45

Asp Glu Val Ser Leu Leu Pro Val Asn Asn Gly Thr His Thr Gly Ile
        50                  55                  60

Leu Phe Leu Asn Thr Thr Ile Ala Glu Ala Ala Phe Ala Asp Lys Asp
65                  70                  75                  80

Asp Leu Glu Lys Arg
                85

<210> SEQ ID NO 7
<211> LENGTH: 469
<212> TYPE: DNA
<213> ORGANISM: Artificial Sequence
<220> FEATURE:
<223> OTHER INFORMATION: DNA sequence of insert (BamHI, T7 promoter,
      alpha-mating factor, Brazzein, HindIII)

<400> SEQUENCE: 7
ggatccgtaa tacgactcac tatagggccc gggcgtcgac atgaagttct ctactatttt    60
ggctgcttct actgctttga tttctgttgt tatggctgct ccagtttcta ctgaaactga   120
tattgatgat ttgccaattt ctgttccaga agaagccttg attggtttta ttgatttgac   180
tggtgacgaa gtttctttgt tgccagttaa caacggtact catactggta ttttgttctt   240
gaacactact attgctgaag ctgctttcgc tgataaggat gatttggaaa agagagataa   300
gtgtaagaag gttacgaaa attacccagt ttctaagtgt caattggcta accaatgtaa   360
ttacgattgt aagttggata agcatgctag atctggtgaa tgttttttacg atgaaaagag   420 aaacttgcaa tgtatttgtg attactgtga atactaatga taaaagctt                469

<210> SEQ ID NO 8
<211> LENGTH: 6631
<212> TYPE: DNA
<213> ORGANISM: Artificial Sequence
<220> FEATURE:
<223> OTHER INFORMATION: DNA sequence of pESC-URA vector

<400> SEQUENCE: 8
tcgcgcgttt cggtgatgac ggtgaaaacc tctgacacat gcagctcccg gagacggtca    60
```

```
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accataccac agcttttcaa ttcaattcat cattttttt ttattctttt ttttgatttc     240
ggtttctttg aaatttttt gattcggtaa tctccgaaca gaaggaagaa cgaaggaagg     300
agcacagact tagattggta tatatacgca tatgtagtgt tgaagaaaca tgaaattgcc    360
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa tttttactc ttcgaagaca gaaaatttgc tgacattggt aatacagtca    720
aattgcagta ctctgcgggt gtatacgaaa tagcagaatg ggcagacatt acgaatgcac    780
acggtgtggt gggcccaggt attgttagcg gtttgaagca ggcggcagaa gaagtaacaa    840
aggaacctag aggcctttg atgttagcag aattgtcatg caagggctcc ctatctactg     900
gagaatatac taagggtact gttgacattg cgaagagcga caaagatttt gttatcggct    960
ttattgctca agagacatg ggtggaagag atgaaggtta cgattggttg attatgacac     1020
ccggtgtggg tttagatgac aagggagacg cattgggtca acagtataga accgtggatg    1080
atgtggtctc tacaggatct gacattatta ttgttggaag aggactattt gcaaagggaa    1140
gggatgctaa ggtagagggt gaacgttaca gaaaagcagg ctgggaagca tatttgagaa    1200
gatgcggcca gcaaaactaa aaaactgtat tataagtaaa tgcatgtata ctaaactcac    1260
aaattagagc ttcaatttaa ttatatcagt tattaccta tgcggtgtga aataccgcac      1320
agatgcgtaa ggagaaaata ccgcatcagg aaattgtaaa cgttaatatt tgttaaaat     1380 tcgcgttaaa ttttttgttaa atcagctcat tttttaacca ataggccgaa atcggcaaaa    1440
tcccttataa atcaaaagaa tagaccgaga tagggttgag tgttgttcca gtttggaaca    1500
agagtccact attaaagaac gtggactcca acgtcaaagg cgaaaaaacc gtctatcagg    1560
gcgatggccc actacgtgaa ccatcaccct aatcaagttt tttggggtcg aggtgccgta    1620
aagcactaaa tcggaacccct aaagggagcc cccgatttag agcttgacgg ggaaagccgg    1680
cgaacgtggc gagaaaggaa gggaagaaag cgaaaggagc gggcgctagg gcgctggcaa    1740
gtgtagcggt cacgctgcgc gtaaccacca cacccgccgc gcttaatgcg ccgctacagg    1800
gcgcgtccat tcgccattca ggctgcgcaa ctgttgggaa gggcgatcgg tgcgggcctc    1860
ttcgctatta cgccagctga attggagcga cctcatgcta tacctgagaa agcaacctga    1920
cctacaggaa agagttactc aagaataaga atttcgtttt aaaacctaa gagtcacttt     1980 aaaatttgta tacacttatt tttttataaa cttatttaat aataaaaatc ataaatcata    2040
agaaattcgc ttatttagaa gtgtcaacaa cgtatctacc aacgatttga cccttttcca    2100
tcttttcgta aatttctggc aaggtagaca agccgacaac cttgattgga gacttgacca    2160
aacctctggc gaagaattgt taattaagag ctcagatctt atcgtcgtca tccttgtaat    2220
ccatcgatac tagtgcggcc gcccttttagt gagggttgaa ttcgaatttt caaaaattct    2280
tacttttttt ttggatggac gcaaagaagt ttaataatca tattcatgg cattaccacc     2340 atatacatat ccatatacat atccatatct aatcttactt atatgttgtg gaaatgtaaa    2400
gagccccatt atcttagcct aaaaaaacct tctctttgga actttcagta atacgcttaa    2460
```

```
ctgctcattg ctatattgaa gtacggatta gaagccgccg agcgggtgac agccctccga    2520
aggaagactc tcctccgtgc gtcctcgtct tcaccggtcg cgttcctgaa acgcagatgt    2580
gcctcgcgcc gcactgctcc gaacaataaa gattctacaa tactagcttt tatggttatg    2640
aagaggaaaa attggcagta acctggcccc acaaaccttc aaatgaacga atcaaattaa    2700
caaccatagg atgataatgc gattagtttt ttagccttat ttctggggta attaatcagc    2760
gaagcgatga tttttgatct attaacagat atataaatgc aaaaactgca taaccacttt    2820
aactaatact ttcaacattt tcggtttgta ttacttctta ttcaaatgta ataaagtat    2880
caacaaaaaa ttgttaatat acctctatac tttaacgtca aggagaaaaa accccggatc    2940
cgtaatacga ctcactatag ggcccgggcg tcgacatgga acagaagttg atttccgaag    3000
aagacctcga gtaagcttgg taccgcggct agctaagatc cgctctaacc gaaaaggaag    3060
gagttagaca acctgaagtc taggtcccta tttattttt tatagttatg ttagtattaa    3120
gaacgttatt tatatttcaa attttctttt tttttctgta cagacgcgtg tacgcatgta    3180
acattatact gaaaaccttg cttgagaagg ttttgggacg ctcgaagatc cagctgcatt    3240
aatgaatcgg ccaacgcgcg gggagaggcg gtttgcgtat tgggcgctct tccgcttcct    3300
cgctcactga ctcgctgcgc tcggtcgttc ggctgcggcg agcggtatca gctcactcaa    3360
aggcggtaat acggttatcc acagaatcag gggataacgc aggaaagaac atgtgagcaa    3420
aaggccagca aaaggccagg aaccgtaaaa aggccgcgtt gctggcgttt ttccataggc    3480
tccgcccccc tgacgagcat cacaaaaatc gacgctcaag tcagaggtgg cgaaacccga    3540
caggactata aagataccag gcgtttcccc ctggaagctc cctcgtgcgc tctcctgttc    3600
cgaccctgcc gcttaccgga tacctgtccg ccttctccc ttcgggaagc gtggcgcttt    3660
ctcatagctc acgctgtagg tatctcagtt cggtgtaggt cgttcgctcc aagctgggct    3720
gtgtgcacga accccccgtt cagcccgacc gctgcgcctt atccggtaac tatcgtcttg    3780
agtccaaccc ggtaagacac gacttatcgc cactggcagc agccactggt aacaggatta    3840
gcagagcgag gtatgtaggc ggtgctacag agttcttgaa gtggtggcct aactacggct    3900
acactagaag gacagtattt ggtatctgcg ctctgctgaa gccagttacc ttcggaaaaa    3960
gagttggtag ctcttgatcc ggcaaacaaa ccaccgctgg tagcggtggt ttttttgttt    4020
gcaagcagca gattacgcgc agaaaaaaag gatctcaaga agatcctttg atcttttcta    4080
cggggtctga cgctcagtgg aacgaaaact cacgttaagg attttggtc atgagattat    4140
caaaaaggat cttcacctag atccttttaa attaaaaatg aagttttaaa tcaatctaaa    4200
gtatatatga gtaaacttgg tctgacagtt accaatgctt aatcagtgag gcacctatct    4260
cagcgatctg tctatttcgt tcatccatag ttgcctgact ccccgtcgtg tagataacta    4320
cgatacggga gggcttacca tctggcccca gtgctgcaat gataccgcga cccacgct    4380
caccggctcc agatttatca gcaataaacc agccagccgg aagggccgag cgcagaagtg    4440
gtcctgcaac tttatccgcc tccatccagt ctattaattg ttgccgggaa gctagagtaa    4500
gtagttcgcc agttaatagt ttgcgcaacg ttgttgccat tgctacaggc atcgtggtgt    4560
cacgctcgtc gtttggtatg gcttcattca gctccggttc ccaacgatca aggcgagtta    4620
catgatcccc catgttgtgc aaaaaagcgg ttagctcctt cggtcctccg atcgttgtca    4680
gaagtaagtt ggccgcagtg ttatcactca tggttatggc agcactgcat aattctctta    4740
ctgtcatgcc atccgtaaga tgcttttctg tgactggtga gtactcaacc aagtcattct    4800
```

| | |
|---|---|
| gagaatagtg tatgcggcga ccgagttgct cttgcccggc gtcaatacgg gataataccg | 4860 |
| cgccacatag cagaacttta aaagtgctca tcattggaaa acgttcttcg gggcgaaaac | 4920 |
| tctcaaggat cttaccgctg ttgagatcca gttcgatgta acccactcgt gcacccaact | 4980 |
| gatcttcagc atcttttact ttcaccagcg tttctgggtg agcaaaaaca ggaaggcaaa | 5040 |
| atgccgcaaa aaagggaata agggcgacac ggaaatgttg aatactcata ctcttccttt | 5100 |
| ttcaatatta ttgaagcatt tatcagggtt attgtctcat gagcggatac atatttgaat | 5160 |
| gtatttagaa aaataaacaa ataggggttc cgcgcacatt tccccgaaaa gtgccacctg | 5220 |
| aacgaagcat ctgtgcttca ttttgtagaa caaaaatgca acgcgagagc gctaattttt | 5280 |
| caaacaaaga atctgagctg catttttaca gaacagaaat gcaacgcgaa agcgctattt | 5340 |
| taccaacgaa gaatctgtgc ttcattttg taaaacaaaa atgcaacgcg agagcgctaa | 5400 |
| ttttcaaac aaagaatctg agctgcattt ttacagaaca gaaatgcaac gcgagagcgc | 5460 |
| tattttacca acaagaatc tatacttctt ttttgttcta caaaaatgca tcccgagagc | 5520 |
| gctatttttc taacaaagca tcttagatta ctttttttct cctttgtgcg ctctataatg | 5580 |
| cagtctcttg ataactttt gcactgtagg tccgttaagg ttagaagaag gctactttgg | 5640 |
| tgtctatttt ctcttccata aaaaaagcct gactccactt cccgcgttta ctgattacta | 5700 |
| gcgaagctgc gggtgcattt tttcaagata aaggcatccc cgattatatt ctataccgat | 5760 |
| gtggattgcg catactttgt gaacagaaag tgatagcgtt gatgattctt cattggtcag | 5820 |
| aaaattatga acggtttctt ctattttgtc tctatatact acgtatagga aatgtttaca | 5880 |
| ttttcgtatt gttttcgatt cactctatga atagttctta ctacaatttt tttgtctaaa | 5940 |
| gagtaatact agagataaac ataaaaaatg tagaggtcga gtttagatgc aagttcaagg | 6000 |
| agcgaaaggt ggatgggtag gttatatagg gatatagcac agagatatat agcaaagaga | 6060 |
| tacttttgag caatgtttgt ggaagcggta ttcgcaatat tttagtagct cgttacagtc | 6120 |
| cggtgcgttt ttggtttttt gaaagtgcgt cttcagagcg cttttggttt tcaaaagcgc | 6180 |
| tctgaagttc ctatactttc tagagaatag gaacttcgga ataggaactt caaagcgttt | 6240 |
| ccgaaaacga gcgcttccga aaatgcaacg cgagctgcgc acatacagct cactgttcac | 6300 |
| gtcgcaccta tatctgcgtg ttgcctgtat atatatatac atgagaagaa cggcatagtg | 6360 |
| cgtgtttatg cttaaatgcg tacttatatg cgtctattta tgtaggatga aaggtagtct | 6420 |
| agtacctcct gtgatattat cccattccat gcggggtatc gtatgcttcc ttcagcacta | 6480 |
| cccttagct gttctatatg ctgccactcc tcaattggat tagtctcatc cttcaatgct | 6540 |
| atcatttcct ttgatattgg atcatactaa gaaaccatta ttatcatgac attaacctat | 6600 |
| aaaaatagc gtatcacgag gccctttcgt c | 6631 |

<210> SEQ ID NO 9
<211> LENGTH: 5321
<212> TYPE: DNA
<213> ORGANISM: Artificial Sequence
<220> FEATURE:
<223> OTHER INFORMATION: DNA sequence of pD1214-FAKS

<400> SEQUENCE: 9

| | |
|---|---|
| tcagaattgg ttaattggtt gtaacactga cccctatttg tttatttttc taaatacatt | 60 |
| caaatatgta tccgctcatg agacaataac cctgataaat gttcaataat attgaaaaag | 120 |
| gaagaatatg agtattcaac atttccgtgt cgcccttatt cccttttttg cggcattttg | 180 |
| ccttcctgtt tttgctcacc cagaaacgct ggtgaaagta aaagatgctg aagatcagtt | 240 |

```
gggtgcacga gtgggttaca tcgaactgga tctcaacagc ggtaagatcc ttgagagttt     300
tcgccccgaa gaacgttttc caatgatgag cacttttaaa gttctgctat gtggcgcggt     360
attatcccgt attgacgccg ggcaagagca actcggtcgc cgcatacact attctcagaa     420
tgacttggtt gagtactcac cagtcacaga aaagcatctt acggatggca tgacagtaag     480
agaattatgc agtgctgcca taaccatgag tgataacact gcggccaact tacttctgac     540
aacgatcgga ggaccgaagg agctaaccgc ttttttgcac aacatggggg atcatgtaac     600
tcgccttgat cgttgggaac cggagctgaa tgaagccata ccaaacgacg agcgtgacac     660
cacgatgcct gtagcgatgg caacaacgtt gcgcaaacta ttaactggcg aactacttac     720
tctagcttcc cggcaacaat taatagactg gatggaggcg gataaagttg caggaccact     780
tctgcgctcg gccctccgg ctggctggtt tattgctgat aaatccggag ccggtgagcg     840
tggttctcgc ggtatcatcg cagcgctggg gccagatggt aagccctccc gtatcgtagt     900
tatctacacg acggggagtc aggcaactat ggatgaacga atagacaga tcgctgagat     960
aggtgcctca ctgattaagc attggtaact catgaccaaa atcccttaac gtgagttacg    1020
cgcgcgtcgt tcactgagcg tcagacccg tagaaaagat caaaggatct tcttgagatc    1080
cttttttct gcgcgtaatc tgctgcttgc aaacaaaaaa accaccgcta ccagcggtgg    1140
tttgtttgcc ggatcaagag ctaccaactc ttttccgaa ggtaactggt tcagcagagc    1200
gcagatacca aatactgttc ttctagtgta gccgtagtta gcccaccact tcaagaactc    1260
tgtagcaccg cctacatacc tcgctctgct aatcctgtta ccagtggctg ctgccagtgg    1320
cgataagtcg tgtcttaccg ggttggactc aagacgatag ttaccggata aggcgcagcg    1380
gtcgggctga acggggggtt cgtgcacaca gcccagcttg gagcgaacga cctacaccga    1440
actgagatac ctacagcgtg agctatgaga aagcgccacg cttcccgaag ggagaaaggc    1500
ggacaggtat ccggtaagcg gcagggtcgg aacaggagag cgcacgaggg agcttccagg    1560
gggaaacgcc tggtatcttt atagtcctgt cgggtttcgc cacctctgac ttgagcgtga    1620
ttttttgtgat gctcgtcagg ggcggagc ctatggaaaa acgccagcaa cgcggccttt    1680
tacggttcct ggccttttgc tggcctttg ctcacatgtt ctttcctgcg ttatcccctg    1740
attctgtgga taaccgtatt accgcctttg agtgagctga taccgctcgg ggtcgtgcag    1800
gtatagcttc aaaatgtttc tactcctttt ttactcttcc agattttctc ggactccgcg    1860
catcgccgta ccacttcaaa acacccaagc acagcatact aaatttcccc tctttcttcc    1920
tctagggtgt cgttaattac ccgtactaaa ggtttggaaa agaaaaagt gaccgcctcg    1980
tttcttttc ttcgtcgaaa aaggcaataa aaattttat cacgtttctt tttcttgaaa    2040
atttttttt ttgattttt tctctttcga tgacctccca ttgatattta agttaataaa    2100
cggacttcaa tttctcaagt ttcagtttca tttttcttgt tctattacaa cttttttac    2160
ttcttgtcat tagaaagaaa gcatagcaat ctaattaagt ttaaatgaga ttcccatcta    2220
ttttcaccgc tgtcttgttc gctgcctcct ctgcattggc tgcccctgtt aacactacca    2280
ctgaagacga gactgctcaa attccagctg aagcagttat cggttactct gaccttgagg    2340
gtgatttcga cgtcgctgtt ttgcctttct ctaactccac taacaacggt tgttgttca    2400
ttaacaccac tatcgcttcc attgctgcta aggaagaggg tgtctctctc gagaaaagag    2460
aggccgaagc tatgagggca tccaggtaac agtctcgagt ggttgaatca tgtaattagt    2520
tatgtcacgc ttacattcac gccctccccc cacatccgct ctaaccgaaa aggaaggagt    2580
```

-continued

```
tagacaacct gaagtctagg tccctattta ttttttttata gttatgttag tattaagaac    2640
gttatttata tttcaaattt ttctttttt  tctgtacaga cgcgtgtacg catgtaacat    2700
tatactgaaa accttgttga aaggttttg  ggacgctcga aggctttaat ttgcggcccc    2760
tcacctgcac gcaaaaagct tttcaattca attcatcatt ttttttttat tcttttttt    2820
gatttcggtt tctttgaaat tttttgatt  cggtaatctc cgaacagaag gaagaacgaa    2880
ggaaggagca cagacttaga ttggtatata tacgcatata tagtgttgaa gaaacatgaa    2940
attgcccagt attttaaccc aactgcacag aacaaaaacc agcaggaaac gaagataaat    3000
catgtcgaaa gctacatata aggaacgtgc tgctactcat cctagtcctg ttgctgccaa    3060
gctatttaat atcatgcacg aaaagcaaac aaacttgtgt gcttcattgg atgttgtacc    3120
accaaggaat tactggagtt agttgaagca ttaggtccca aaatttgttt actaaaaaca    3180
catgtggata tcttgactga ttttttccatg gagggcacag ttaagccgct aaaggcatta    3240
tccgccaagt acaatttttt actcttcgaa gatagaaaat ttgctgacat tggtaataca    3300
gtcaaattgc agtacccaga atagcagaat gggcagacat tacgaatgca cacggtgtgg    3360
tgggcccagg tattgttagc ggtttgaagc aggcggcaga agaagtaaca aaggaaccta    3420
gaggcctttt gatgttagca gaattgtcat gcaagggctc cctatctact ggagaatata    3480
ctaagggtac tgttgacatt gcgaaaagcg acaaagattt tgttatcggc tttattgctc    3540
aaagagacat gggtggaaga gatgaaggtt acgattggtt gattatgaca cccggtgtgg    3600
gtttagatga caagggagat gcattgggtc aacagtatag aaccgtggat gatgttgtct    3660
ctacaggatc tgcatattat attgttggaa gaggactatt tgcaaaggga agggatgcta    3720
aggtagaggg tgaacgttac agaaaagcag gctgggaagc atatttgaga agatgcggca    3780
gcaaaactaa aaaactgtat tataagtaaa tgcatgtata ctaaactcac aaattagagc    3840
ttcaatttaa ttatatcagt tattacccac gctatgatcc aatatcaaag gaaatgatag    3900
cattgaagga tgagactaat ccaattgagg agtggcagca tatagaacag ctaaagggta    3960
gtgctgaagg aagcatacga tacccccgcat ggaatgggat aatatcacag gaggtactag    4020
actacctttc atcctacata aatagacgca tataagtacg catttaagca taaacacgca    4080
ctatgccgtt cttctcatgt atatatatat acaggcaaca cgcagatata ggtgcgacgt    4140
gaacagtgag ctgtatgtgc gcagctcgcg ttgcattttc ggaagcgctc gttttcggaa    4200
acgctttgaa gttcctattc cgaagttcct attctctaga aagtatagga acttcagagc    4260
gcttttgaaa accaaaagcg ctctgaagtc gcactttcaa aaaaccaaaa acgcaccgga    4320
ctgtaacgag ctactaaaat attggaatac cgcttccaca acattgctc  aaaagtatct    4380
ctttgctata tatctctgtg ctatatccct atataaccta cccatccacc tttcgctcct    4440
tgaacttgca tctaaactcg acctctacat ttttatgtt  tatctctagt attactcttt    4500
agacaaaaaa attgtagtaa gaactattca tagagtgaat cgaaaacaat acgaaaatgt    4560
aaacatttcc tatacgtagt atatagagac aaaatagaag aaaccgttca taattttctg    4620
accaatgaag aatcatcaac gctatcactt tctgttcaca agtatgcgc  aatccacatc    4680
ggtatagaat ataatcgggg atgccttttat cttgaaaaaa tgcacccgca gcttcgctag    4740
taatcagtaa acgcgggaag tggagtcagg cttttttttat ggaagagaaa atagacacca    4800
aagtagcctt cttctaacct taacggacct acagtgcaaa aagttatcaa gagactgcat    4860
tatagagcgc acaaggaga  aaaaagtaa  tctaagatgc tttgttagaa aaatagcgct    4920
ctcgggatgc attttttgtag aacaaaaaag aagtatagat tctttgttgg taaaatagcg    4980
```

```
ctctcgcgtt gcatttctgt tctgtaaaaa tgcagctcag attctttgtt tgaaaaatta    5040
gcgctctcgc gttgcatttt tgttttacaa aaatgaagca cagattcttc gttggtaaaa    5100
tagcgctttc gcgttgcatt tctgttctgt aaaaatgcag ctcagattct tgtttgaaa     5160 aattagcgct ctcgcgttgc attttgttc tacaaaatga agcacagatg cttcgttcag    5220
gtggcacttt cggggaaat gtgcgcggaa cccctatttg tttatttttc taaatacatt    5280
caaatatgta tccgctcatg agacaataac cctgatattg g                      5321
```

<210> SEQ ID NO 10
<211> LENGTH: 7017
<212> TYPE: DNA
<213> ORGANISM: Artificial Sequence
<220> FEATURE:
<223> OTHER INFORMATION: DNA sequence of recombinant pESC-Brazzein vector

<400> SEQUENCE: 10

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accataccac agcttttcaa ttcaattcat cattttttt ttattctttt ttttgatttc     240
ggtttctttg aaattttttt gattcggtaa tctccgaaca aaggaagaa cgaaggaagg     300 agcacagact tagattggta tatatacgca tatgtagtgt tgaagaaaca tgaaattgcc     360
cagtattctt aacccaactg cacagaacaa aaacctgcag gaaacgaaga taaatcatgt     420
cgaaagctac atataaggaa cgtgctgcta ctcatcctag tcctgttgct gccaagctat     480
ttaatatcat gcacgaaaag caaacaaact tgtgtgcttc attggatgtt cgtaccacca     540
aggaattact ggagttagtt gaagcattag gtcccaaaat ttgtttacta aaaacacatg     600
tggatatctt gactgatttt tccatggagg gcacagttaa ccgctaaag gcattatccg     660 ccaagtacaa ttttttactc ttcgaagaca gaaaatttgc tgacattggt aatacagtca     720
aattgcagta ctctgcgggt gtatacagaa tagcagaatg gcagacatt acgaatgcac     780 acggtgtggt gggcccaggt attgttagcg gtttgaagca ggcggcagaa gaagtaacaa     840
aggaacctag aggcctttg atgttagcag aattgtcatg caagggctcc ctatctactg     900
gagaatatac taagggtact gttgacattg cgaagagcga caaagatttt gttatcggct     960
ttattgctca aagagacatg ggtggaagag atgaaggtta cgattggttg attatgacac    1020
ccggtgtggg tttagatgac aagggagacg cattgggtca acagtataga accgtggatg    1080
atgtggtctc tacaggatct gacattatta ttgttggaag aggactattt gcaaagggaa    1140
gggatgctaa ggtagagggt gaacgttaca gaaaagcagg ctgggaagca tatttgagaa    1200
gatgcggcca gcaaaactaa aaaactgtat tataagtaaa tgcatgtata ctaaactcac    1260
aaattagagc ttcaatttaa ttatatcagt tattacccta tgcggtgtga ataccgcac    1320 agatgcgtaa ggagaaaata ccgcatcagg aaattgtaaa cgttaatatt tgttaaaat    1380 tcgcgttaaa ttttgtta atcagctcat tttttaacca ataggccgaa atcggcaaaa    1440
tcccttataa atcaaaagaa tagaccgaga tagggttgag tgttgttcca gtttggaaca    1500
agagtccact attaaagaac gtggactcca acgtcaaagg gcgaaaaacc gtctatcagg    1560
gcgatggccc actacgtgaa ccatcaccct aatcaagttt ttggggtcg aggtgccgta    1620 aagcactaaa tcggaaccct aaagggagcc ccgatttag agcttgacgg ggaaagccgg    1680
```

```
cgaacgtggc gagaaaggaa gggaagaaag cgaaaggagc gggcgctagg gcgctggcaa    1740
gtgtagcggt cacgctgcgc gtaaccacca cacccgccgc gcttaatgcg ccgctacagg    1800
gcgcgtccat tcgccattca ggctgcgcaa ctgttgggaa gggcgatcgg tgcgggcctc    1860
ttcgctatta cgccagctga attggagcga cctcatgcta tacctgagaa agcaacctga    1920
cctacaggaa agagttactc aagaataaga attttcgttt taaaacctaa gagtcacttt    1980
aaaatttgta tacacttatt ttttttataa cttatttaat aataaaaatc ataaatcata    2040
agaaattcgc ttatttagaa gtgtcaacaa cgtatctacc aacgatttga ccctttccca    2100
tcttttcgta aatttctggc aaggtagaca agccgacaac cttgattgga gacttgacca    2160
aacctctggc gaagaattgt taattaagag ctcagatctt atcgtcgtca tccttgtaat    2220
ccatcgatac tagtgcggcc gcccttttagt gagggttgaa ttcgaatttt caaaaattct    2280
tacttttttt ttggatggac gcaaagaagt ttaataatca tattacatgg cattaccacc    2340
atatacatat ccatatacat atccatatct aatcttactt atatgttgtg gaaatgtaaa    2400 gagcccccatt atcttagcct aaaaaaacct tctctttgga actttcagta atacgcttaa    2460
ctgctcattg ctatattgaa gtacggatta gaagccgccg agcgggtgac agccctccga    2520
aggaagactc tcctccgtgc gtcctcgtct tcaccggtcg cgttcctgaa acgcagatgt    2580
gcctcgcgcc gcactgctcc gaacaataaa gattctacaa tactagcttt tatggttatg    2640
aagaggaaaa attggcagta acctggcccc acaaaccttc aaatgaacga atcaaattaa    2700
caaccatagg atgataatgc gattagtttt ttagccttat ttctggggta attaatcagc    2760
gaagcgatga ttttgatct attaacagat atataaatgc aaaaactgca taaccacttt    2820
aactaatact ttcaacattt tcggtttgta ttacttctta ttcaaatgta ataaaagtat    2880
caacaaaaaa ttgttaatat acctctatac tttaacgtca aggagaaaaa accccggatc    2940
cgtaatacga ctcactatag ggcccgggcg tcgacatgaa gttctctact attttggctg    3000
cttctactgc tttgatttct gttgttatgg ctgctccagt ttctactgaa actgatattg    3060
atgatttgcc aatttctgtt ccagaagaag ccttgattgg ttttattgat ttgactggtg    3120
acgaagtttc tttgttgcca gttaacaacg gtactcatac tggtattttg ttcttgaaca    3180
ctactattgc tgaagctgct ttcgctgata aggatgattt ggaaagagag gataagtgta    3240
agaaggttta cgaaaattac ccagtttcta gtgtcaatt ggctaaccaa tgtaattacg    3300
attgtaagtt ggataagcat gctagatctg gtgaatgttt ttacgatgaa aagagaaact    3360
tgcaatgtat ttgtgattac tgtgaatact aatgataaaa gcttggtacc gcggctagct    3420
aagatccgct ctaaccgaaa aggaaggagt tagacaacct gaagtctagg tccctattta    3480
tttttttata gttatgttag tattaagaac gttatttata tttcaaattt ttcttttttt    3540
tctgtacaga cgcgtgtacg catgtaacat tatactgaaa accttgcttg agaaggtttt    3600
gggacgctcg aagatccagc tgcattaatg aatcggccaa cgcgcgggga gaggcggttt    3660
gcgtattggg cgctcttccg cttcctcgct cactgactcg ctgcgctcgg tcgttcggct    3720
gcggcgagcg gtatcagctc actcaaaggc ggtaatacgg ttatccacag aatcagggga    3780
taacgcagga aagaacatgt gagcaaaagg ccagcaaaag gccaggaacc gtaaaaaggc    3840
cgcgttgctg gcgttttttcc ataggctccg ccccccctgac gagcatcaca aaaatcgacg    3900
ctcaagtcag aggtggcgaa acccgacagg actataaaga taccaggcgt ttccccctgg    3960
aagctccctc gtgcgctctc ctgttccgac cctgccgctt accggatacc tgtccgcctt    4020
```

```
tctcccttcg ggaagcgtgg cgctttctca tagctcacgc tgtaggtatc tcagttcggt    4080
gtaggtcgtt cgctccaagc tgggctgtgt gcacgaaccc cccgttcagc ccgaccgctg    4140
cgccttatcc ggtaactatc gtcttgagtc caacccggta agacacgact tatcgccact    4200
ggcagcagcc actggtaaca ggattagcag agcgaggtat gtaggcggtg ctacagagtt    4260
cttgaagtgg tggcctaact acggctacac tagaaggaca gtatttggta tctgcgctct    4320
gctgaagcca gttaccttcg gaaaaagagt tggtagctct tgatccggca aacaaaccac    4380
cgctggtagc ggtggttttt tgtttgcaa gcagcagatt acgcgcagaa aaaaggatc    4440
tcaagaagat cctttgatct tttctacggg gtctgacgct cagtggaacg aaaactcacg    4500
ttaagggatt ttggtcatga gattatcaaa aaggatcttc acctagatcc ttttaaatta    4560
aaaatgaagt tttaaatcaa tctaaagtat atatgagtaa acttggtctg acagttacca    4620
atgcttaatc agtgaggcac ctatctcagc gatctgtcta tttcgttcat ccatagttgc    4680
ctgactcccc gtcgtgtaga taactacgat acgggagggc ttaccatctg gccccagtgc    4740
tgcaatgata ccgcgagacc cacgctcacc ggctccagat ttatcagcaa taaaccagcc    4800
agccggaagg gccgagcgca gaagtggtcc tgcaacttta tccgcctcca tccagtctat    4860
taattgttgc cgggaagcta gagtaagtag ttcgccagtt aatagtttgc gcaacgttgt    4920
tgccattgct acaggcatcg tggtgtcacg ctcgtcgttt ggtatggctt cattcagctc    4980
cggttcccaa cgatcaaggc gagttacatg atccccatg ttgtgcaaaa aagcggttag    5040
ctccttcggt cctccgatcg ttgtcagaag taagttggcc gcagtgttat cactcatggt    5100
tatggcagca ctgcataatt ctcttactgt catgccatcc gtaagatgct tttctgtgac    5160
tggtgagtac tcaaccaagt cattctgaga atagtgtatg cggcgaccga gttgctcttg    5220
cccggcgtca atacgggata ataccgcgcc acatagcaga actttaaaag tgctcatcat    5280
tggaaaacgt tcttcggggc gaaaactctc aaggatctta ccgctgttga tccagttc    5340
gatgtaaccc actcgtgcac ccaactgatc ttcagcatct tttactttca ccagcgtttc    5400
tgggtgagca aaaacaggaa ggcaaaatgc cgcaaaaaag gaataagggc gacacggaa    5460
atgttgaata ctcatactct tccttttca atattattga agcatttatc agggttattg    5520
tctcatgagc ggatacatat ttgaatgtat ttagaaaaat aaacaaatag gggttccgcg    5580
cacatttccc cgaaaagtgc cacctgaacg aagcatctgt gcttcatttt gtagaacaaa    5640
aatgcaacgc gagagcgcta ttttttcaaa caaagaatct gagctgcatt tttacagaac    5700
agaaatgcaa cgcgaaagcg ctattttacc aacgaagaat ctgtgcttca tttttgtaaa    5760
acaaaaatgc aacgcgagag cgctaatttt tcaaacaaag aatctgagct gcatttttac    5820
agaacagaaa tgcaacgcga gagcgctatt taccaacaa agaatctata cttcttttt    5880
gttctacaaa aatgcatccc gagagcgcta ttttctaac aaagcatctt agattacttt    5940
ttttctcctt tgtgcgctct ataatgcagt ctcttgataa cttttgcac tgtaggtccg    6000
ttaaggttag aagaaggcta ctttggtgtc tattttctct tccataaaaa aagcctgact    6060
ccacttcccg cgtttactga ttactagcga agctgcgggt gcattttttc aagataaagg    6120
catccccgat tatattctat accgatgtgg attgcgcata ctttgtgaac agaaagtgat    6180
agcgttgatg attcttcatt ggtcagaaaa ttatgaacgg tttcttctat tttgtctcta    6240
tatactacgt ataggaaatg tttacatttt cgtattgttt tcgattcact ctatgaatag    6300
ttcttactac aatttttttg tctaaagagt aatactagag ataaacataa aaaatgtaga    6360
ggtcgagttt agatgcaagt tcaaggagcg aaaggtggat gggtaggtta tatagggata    6420
```

```
tagcacagag atatatagca aagagatact tttgagcaat gtttgtggaa gcggtattcg    6480
caatatttta gtagctcgtt acagtccggt gcgttttttgg ttttttgaaa gtgcgtcttc   6540
agagcgcttt tggttttcaa aagcgctctg aagttcctat actttctaga gaataggaac   6600
ttcggaatag gaacttcaaa gcgtttccga aaacgagcgc ttccgaaaat gcaacgcgag   6660
ctgcgcacat acagctcact gttcacgtcg cacctatatc tgcgtgttgc ctgtatatat   6720
atatacatga agaacggc atagtgcgtg tttatgctta aatgcgtact tatatgcgtc    6780
tatttatgta ggatgaaagg tagtctagta cctcctgtga tattatccca ttccatgcgg   6840
ggtatcgtat gcttccttca gcactaccct ttagctgttc tatatgctgc cactcctcaa   6900
ttggattagt ctcatccttc aatgctatca tttcctttga tattggatca tactaagaaa   6960
ccattattat catgacatta acctataaaa ataggcgtat cacgaggccc tttcgtc     7017

<210> SEQ ID NO 11
<211> LENGTH: 5468
<212> TYPE: DNA
<213> ORGANISM: Artificial Sequence
<220> FEATURE:
<223> OTHER INFORMATION: DNA sequence of recombinant pD1214-Brazzein
      vector

<400> SEQUENCE: 11
tcagaattgg ttaattggtt gtaacactga cccctatttg tttattttc taaatacatt      60 caaatatgta tccgctcatg agacaataac cctgataaat gttcaataat attgaaaaag    120
gaagaatatg agtattcaac atttccgtgt cgcccttatt cccttttttg cggcattttg    180
ccttcctgtt tttgctcacc cagaaacgct ggtgaaagta aaagatgctg aagatcagtt    240
gggtgcacga gtgggttaca tcgaactgga tctcaacagc ggtaagatcc ttgagagttt    300
tcgccccgaa gaacgttttc caatgatgag cacttttaaa gttctgctat gtggcgcggt    360
attatcccgt attgacgccg ggcaagagca actcggtcgc cgcatacact attctcagaa    420
tgacttggtt gagtactcac cagtcacaga aaagcatctt acggatggca tgacagtaag    480
agaattatgc agtgctgcca taaccatgag tgataacact gcggccaact tacttctgac    540
aacgatcgga ggaccgaagg agctaaccgc ttttttgcac aacatggggg atcatgtaac    600
tcgccttgat cgttgggaac cggagctgaa tgaagccata ccaaacgacg agcgtgacac    660
cacgatgcct gtagcgatgg caacaacgtt gcgcaaacta ttaactggcg aactacttac    720
tctagcttcc cggcaacaat taatagactg gatggaggcg gataaagttg caggaccact    780
tctgcgctcg gcccttccgg ctggctggtt tattgctgat aaatccggag ccggtgagcg    840
tggttctcgc ggtatcatcg cagcgctggg gccagatggt aagccctccc gtatcgtagt    900
tatctacacg acggggagtc aggcaactat ggatgaacga aatagacaga tcgctgagat    960
aggtgcctca ctgattaagc attggtaact catgaccaaa atcccttaac gtgagttacg   1020
cgcgcgtcgt tcactgagcg tcagaccccg tagaaaagat caaaggatct tcttgagatc   1080 cttttttct gcgcgtaatc tgctgcttgc aaacaaaaaa accaccgcta ccagcggtgg    1140
tttgtttgcc ggatcaagag ctaccaactc ttttccgaa ggtaactggt tcagcagagc    1200
gcagatacca aatactgttc ttctagtgta gccgtagtta gcccaccact tcaagaactc   1260
tgtagcaccg cctacatacc tcgctctgct aatcctgtta ccagtggctg ctgccagtgg   1320
cgataagtcg tgtcttaccg ggttggactc aagacgatag ttaccggata aggcgcagcg   1380
gtcgggctga acggggggtt cgtgcacaca gcccagcttg gagcgaacga cctacaccga   1440
```

```
actgagatac ctacagcgtg agctatgaga aagcgccacg cttcccgaag ggagaaaggc    1500
ggacaggtat ccggtaagcg gcagggtcgg aacaggagag cgcacgaggg agcttccagg    1560
gggaaacgcc tggtatcttt atagtcctgt cgggtttcgc cacctctgac ttgagcgtga    1620
tttttgtgat gctcgtcagg ggggcggagc ctatggaaaa acgccagcaa cgcggctttt    1680
tacggttcct ggccttttgc tggccttttg ctcacatgtt ctttcctgcg ttatcccctg    1740
attctgtgga taaccgtatt accgcctttg agtgagctga taccgctcgg ggtcgtgcag    1800
gtatagcttc aaaatgtttc tactcctttt ttactcttcc agattttctc ggactccgcg    1860
catcgccgta ccacttcaaa acacccaagc acagcatact aaatttcccc tctttcttcc    1920
tctagggtgt cgttaattac ccgtactaaa ggtttggaaa agaaaaaagt gaccgcctcg    1980 tttcttttc ttcgtcgaaa aaggcaataa aaattttat cacgtttctt tttcttgaaa     2040
attttttttt ttgattttt tctctttcga tgacctccca ttgatattta agttaataaa     2100
cggacttcaa tttctcaagt ttcagtttca tttttcttgt tctattacaa ctttttttac    2160
ttcttgtcat tagaaagaaa gcatagcaat ctaattaagt ttaaatgaga ttcccatcta    2220
ttttcaccgc tgtcttgttc gctgcctcct ctgcattggc tgcccctgtt aacactacca    2280
ctgaagacga gactgctcaa attccagctg aagcagttat cggttactct gaccttgagg    2340
gtgatttcga cgtcgctgtt ttgccttct ctaactccac taacaacggt tgttgttca    2400 ttaacaccac tatcgcttcc attgctgcta aggaagaggg tgtctctctc gagaaaagag    2460
ataagtgtaa gaaggtttac gaaaattacc cagtttctaa gtgtcaattg gctaaccaat    2520
gtaattacga ttgtaagttg gataagcatg ctagatctgg tgaatgtttt tacgatgaaa    2580
agagaaactt gcaatgtatt tgtgattact gtgaatacta atgataatcc aggtaacagt    2640
ctcgagtggt tgaatcatgt aattagttat gtcacgctta cattcacgcc ctcccccac     2700 atccgctcta accgaaaagg aaggagttag acaacctgaa gtctaggtcc ctatttattt    2760
ttttatagtt atgttagtat taagaacgtt atttatattt caaattttc ttttttttct     2820 gtacagacgc gtgtacgcat gtaacattat actgaaaacc ttgttgagaa ggttttggga    2880
cgctcgaagg ctttaatttg cggcccctca cctgcacgca aaaagctttt caattcaatt    2940 catcatttt ttttattct ttttttgat ttcggtttct ttgaaatttt tttgattcgg       3000
taatctccga acagaaggaa gaacgaagga aggagcacag acttagattg gtatatatac    3060
gcatatatag tgttgaagaa acatgaaatt gcccagtatt ttaacccaac tgcacagaac    3120
aaaaaccagc aggaaacgaa gataaatcat gtcgaaagct acatataagg aacgtgctgc    3180
tactcatcct agtcctgttg ctgccaagct atttaatatc atgcacgaaa agcaaacaaa    3240
cttgtgtgct tcattggatg ttgtaccacc aaggaattac tggagttagt tgaagcatta    3300
ggtcccaaaa tttgtttact aaaaacacat gtggatatct tgactgattt tccatggag    3360 ggcacagtta agccgctaaa ggcattatcc gccaagtaca atttttact cttcgaagat    3420 agaaaatttg ctgacattgg taatacagtc aaattgcagt acccagaata gcagaatggg    3480
cagacattac gaatgcacac ggtgtggtgg gcccaggtat tgttagcggt ttgaagcagg    3540
cggcagaaga agtaacaaag gaacctagag gcctttttgat gttagcagaa ttgtcatgca    3600
agggctccct atctactgga gaatatacta agggtactgt tgacattgcg aaaagcgaca    3660
aagattttgt tatcggcttt attgctcaaa gagacatggg tggaagagat gaaggttacg    3720
attggttgat tatgacaccc ggtgtgggtt tagatgacaa gggagatgca ttgggtcaac    3780
```

```
agtatagaac cgtggatgat gttgtctcta caggatctga cattattatt gttggaagag    3840
gactatttgc aaagggaagg gatgctaagg tagagggtga acgttacaga aaagcaggct    3900
gggaagcata tttgagaaga tgcggcagca aaactaaaaa actgtattat aagtaaatgc    3960
atgtatacta aactcacaaa ttagagcttc aatttaatta tatcagttat tacccacgct    4020
atgatccaat atcaaaggaa atgatagcat tgaaggatga gactaatcca attgaggagt    4080
ggcagcatat agaacagcta aagggtagtg ctgaaggaag catacgatac cccgcatgga    4140
atgggataat atcacaggag gtactagact acctttcatc ctacataaat agacgcatat    4200
aagtacgcat ttaagcataa acacgcacta tgccgttctt ctcatgtata tatatataca    4260
ggcaacacgc agatataggt gcgacgtgaa cagtgagctg tatgtgcgca gctcgcgttg    4320
cattttcgga agcgctcgtt ttcggaaacg ctttgaagtt cctattccga agttcctatt    4380
ctctagaaag tataggaact tcagagcgct tttgaaaacc aaaagcgctc tgaagtcgca    4440 cttttcaaaaa accaaaaacg caccggacta taacgagcta ctaaaatatt ggaataccgc    4500
ttccacaaac attgctcaaa agtatctctt tgctatatat ctctgtgcta tatccctata    4560
taacctaccc atccaccttt cgctccttga acttgcatct aaactcgacc tctacatttt    4620
ttatgtttat ctctagtatt actctttaga caaaaaaatt gtagtaagaa ctattcatag    4680
agtgaatcga aaacaatacg aaaatgtaaa catttcctat acgtagtata tagagacaaa    4740 ataagaagaaa ccgttcataa ttttctgacc aatgaagaat catcaacgct atcactttct    4800
gttcacaaag tatgcgcaat ccacatcggt atagaatata atcggggatg cctttatctt    4860
gaaaaaatgc acccgcagct tcgctagtaa tcagtaaacg cgggaagtgg agtcaggctt    4920
tttttatgga agagaaaata gacaccaaag tagccttctt ctaaccttaa cggacctaca    4980
gtgcaaaaag ttatcaagag actgcattat agagcgcaca aaggagaaaa aaagtaatct    5040
aagatgcttt gttagaaaaa tagcgctctc gggatgcatt tttgtagaac aaaaaagaag    5100
tatagattct ttgttggtaa aatagcgctc tcgcgttgca tttctgttct gtaaaaatgc    5160
agctcagatt ctttgtttga aaaattagcg ctctcgcgtt gcattttgt tttacaaaaa    5220 tgaagcacag attcttcgtt ggtaaaatag cgctttcgcg ttgcatttct gttctgtaaa    5280
aatgcagctc agattctttg tttgaaaaat tagcgctctc gcgttgcatt tttgttctac    5340
aaaatgaagc acagatgctt cgttcaggtg gcacttttcg gggaaatgtg cgcggaaccc    5400
ctatttgttt attttttctaa atacattcaa atatgtatcc gctcatgaga caataaccct    5460
gatattgg                                                             5468

<210> SEQ ID NO 12
<211> LENGTH: 159
<212> TYPE: DNA
<213> ORGANISM: Artificial Sequence
<220> FEATURE:
<223> OTHER INFORMATION: Wild-type_Brazzein_nucleic acid

<400> SEQUENCE: 12
gataagtgta agaaggttta cgaaaattac ccagtttcta agtgtcaatt ggctaaccaa      60
tgtaattacg attgtaagtt ggataagcat gctagatctg gtgaatgttt ttacgatgaa     120
aagagaaact tgcaatgtat ttgtgattac tgtgaatac                            159

<210> SEQ ID NO 13
<211> LENGTH: 53
<212> TYPE: PRT
<213> ORGANISM: Artificial Sequence
```

```
<220> FEATURE:
<223> OTHER INFORMATION: Wild-type_Brazzein_amino acid

<400> SEQUENCE: 13

Asp Lys Cys Lys Lys Val Tyr Glu Asn Tyr Pro Val Ser Lys Cys Gln
1               5                   10                  15

Leu Ala Asn Gln Cys Asn Tyr Asp Cys Lys Leu Asp Lys His Ala Arg
            20                  25                  30

Ser Gly Glu Cys Phe Tyr Asp Glu Lys Arg Asn Leu Gln Cys Ile Cys
        35                  40                  45

Asp Tyr Cys Glu Tyr
    50

<210> SEQ ID NO 14
<211> LENGTH: 159
<212> TYPE: DNA
<213> ORGANISM: Artificial Sequence
<220> FEATURE:
<223> OTHER INFORMATION: Brazzein variant (H31R_E36D_E41A_K5R)_nucleic
      acid

<400> SEQUENCE: 14
gataagtgta agaaggttta cgaaaattac ccagtttcta agtgtcaatt ggctaaccaa     60
tgtaattacg attgtaagtt ggataagcat gctagatctg gtgaatgttt ttacgatgaa    120
aagagaaact tgcaatgtat ttgtgattac tgtgaatac                           159

<210> SEQ ID NO 15
<211> LENGTH: 53
<212> TYPE: PRT
<213> ORGANISM: Artificial Sequence
<220> FEATURE:
<223> OTHER INFORMATION: Brazzein variant (H31R_E36D_E41A_K5R)_amino
      acid

<400> SEQUENCE: 15

Asp Lys Cys Arg Lys Val Tyr Glu Asn Tyr Pro Val Ser Lys Cys Gln
1               5                   10                  15

Leu Ala Asn Gln Cys Asn Tyr Asp Cys Lys Leu Asp Lys Arg Ala Arg
            20                  25                  30

Ser Gly Asp Cys Phe Tyr Asp Lys Lys Arg Asn Leu Gln Cys Ile Cys
        35                  40                  45

Asp Tyr Cys Glu Tyr
    50

<210> SEQ ID NO 16
<211> LENGTH: 22
<212> TYPE: DNA
<213> ORGANISM: Artificial Sequence
<220> FEATURE:
<223> OTHER INFORMATION: ScACT1 Forward Primer

<400> SEQUENCE: 16
attgccgaaa gaatgcaaaa gg                                              22

<210> SEQ ID NO 17
<211> LENGTH: 22
<212> TYPE: DNA
<213> ORGANISM: Artificial Sequence
<220> FEATURE:
<223> OTHER INFORMATION: ScACT1 Reverse Primer

<400> SEQUENCE: 17
```

-continued

| | |
|---|---|
| gaaccaccaa tccagacgga gt | 22 |

<210> SEQ ID NO 18
<211> LENGTH: 22
<212> TYPE: DNA
<213> ORGANISM: Artificial Sequence
<220> FEATURE:
<223> OTHER INFORMATION: ScURA3 Forward Primer

<400> SEQUENCE: 18

| | |
|---|---|
| tccacccatg tctctttgag ca | 22 |

<210> SEQ ID NO 19
<211> LENGTH: 22
<212> TYPE: DNA
<213> ORGANISM: Artificial Sequence
<220> FEATURE:
<223> OTHER INFORMATION: ScURA3 Reverse Primer

<400> SEQUENCE: 19

| | |
|---|---|
| agaattgtca tgcaagggct cc | 22 |